US009259484B2

(12) United States Patent
Zangemeister-Wittke et al.

(10) Patent No.: US 9,259,484 B2
(45) Date of Patent: *Feb. 16, 2016

(54) METHODS FOR TREATING CANCER USING AN IMMUNOTOXIN

(71) Applicant: University of Zurich, Zurich (CH)

(72) Inventors: Uwe Zangemeister-Wittke, Embrach (CH); Claudio Di Paolo, Zurich (CH); Dominique Christine Tschudi, Zurich (CH); Nicholas Ronald Glover, Oakville (CA); Dimitri Peter Fitsialos, Toronto (CA)

(73) Assignee: UNIVERSITY OF ZURICH, Zurich (CH)

(*) Notice: Subject to any disclaimer, the term of this patent is extended or adjusted under 35 U.S.C. 154(b) by 0 days.

This patent is subject to a terminal disclaimer.

(21) Appl. No.: 14/014,105

(22) Filed: Aug. 29, 2013

(65) Prior Publication Data

US 2014/0178417 A1 Jun. 26, 2014

Related U.S. Application Data

(63) Continuation of application No. 12/698,434, filed on Feb. 2, 2010, now Pat. No. 8,545,840, which is a continuation of application No. 10/554,788, filed as application No. PCT/CA2004/000637 on Apr. 30, 2004, now abandoned.

(60) Provisional application No. 60/466,608, filed on Apr. 30, 2003.

(51) Int. Cl.

| A61K 39/395 | (2006.01) |
|---|---|
| A61K 47/48 | (2006.01) |
| C07K 14/21 | (2006.01) |
| C07K 14/34 | (2006.01) |
| C07K 16/30 | (2006.01) |
| A61K 45/06 | (2006.01) |
| A61K 39/00 | (2006.01) |

(52) U.S. Cl.
CPC ............ *A61K 47/48484* (2013.01); *A61K 45/06* (2013.01); *A61K 47/48607* (2013.01); *C07K 14/21* (2013.01); *C07K 14/34* (2013.01); *C07K 16/30* (2013.01); *A61K 2039/505* (2013.01); *C07K 2317/21* (2013.01); *C07K 2317/24* (2013.01); *C07K 2317/622* (2013.01); *C07K 2319/30* (2013.01)

(58) Field of Classification Search
None
See application file for complete search history.

(56) References Cited

U.S. PATENT DOCUMENTS

| 5,690,928 A | 11/1997 | Heimbrook et al. | |
|---|---|---|---|
| 2002/0146846 A1* | 10/2002 | Pluckthun et al. | 436/518 |
| 2002/0193570 A1 | 12/2002 | Gillies et al. | |

FOREIGN PATENT DOCUMENTS

| WO | WO 00/61635 | 10/2000 |
|---|---|---|
| WO | WO 00/69914 | 11/2000 |
| WO | WO 03/033654 | 4/2003 |

OTHER PUBLICATIONS

Chaubal et al. (Anticancer Research, vol. 19(3B) p. 2237-42, 1999).*
Zorzos et al. (Eur Urol., vol. 28, pp. 251-254, 1995).*
Winter et al. (American Journal of Pathology, vol. 163, No. 6, Dec. 2003).*
Oelschlaeger et al. (Appl. Microbiol. Biotechnol. vol. 61, pp. 123-132, published online Jan. 28, 2003).*
Apantaku et al., Breast cancer diagnosis and screening, *Am Fam Physician*, (Aug. 1, 2000), 62(3):596-602, 605-606.
Azemar et al., Recombinant antibody toxins specific for ErbB2 and EGF receptor inhibit the in vitro growth of human head and neck cancer cells and cause rapid tumor regression in vivo, *Int J Cancer*, (Apr. 15, 2000), 86(2):269-275.
Balzar et al., The biology of the 17-1A antigen (Ep-CAM), *J Mol Med.*, (Oct. 1999), 77(10):699-712.
Battelli et al., Toxicity of ribosome-inactivating proteins-containing immunotoxins to a human bladder carcinoma cell *Int J Cancer*, (Feb. 8, 1996), 65(4):485-490.
Casset et al., A peptide mimetic of an anti-CD4 monoclonal antibody by rational design, *Biochem Biophys Res Commun.*, (Jul. 18, 2003), 307(1):198-205.
Chaubal et al., Ep-CAM—a marker for the detection of disseminated tumor cells in patients suffering from SCCHN, *Anticancer Research*, (May 1999), 19(3B):2237-2242.
Chen et al., Selection and analysis of an optimized anti-VEGF antibody: crystal structure of an affinity-matured fab in comples with antigen, *J Mol Biol.*, (Nov. 5, 1999), 293(4):865-881.
De Pascalis et al., Grafting of abbreviated: complementarity-determining regions containing specificity-determining residues essential for ligand contact to engineer a less immunogenic humanized monoclonal antibody, *J. Immunol.*, (Sep. 15, 2002), 169(6):3076-3084.
Di Paolo et al., A recombinant immunotoxin derived from a humanized epithelial cell adhession molecule-specific single-chain antibody fragment has potent and selective antitumor activity, *Clin Cancer Res.*, (Jul. 2003), 9(7):2837-2848.

(Continued)

*Primary Examiner* — Laura B Goddard
*Assistant Examiner* — Meera Natarajan
(74) *Attorney, Agent, or Firm* — Cooley LLP

(57) ABSTRACT

The present invention relates to methods for preventing or treating head and neck squamous cell cancer and bladder cancer using an immunotoxin comprising (a) a ligand that binds to a protein on the cancer cell attached to; (b) a toxin that is cytotoxic to the cancer cell. In a specific embodiment, the invention is directed to the prevention or treatment of head and neck squamous cell cancer or bladder cancer using Vb4-845, which is a recombinant immunotoxin comprising a humanized, MOC31-derived, single-chain antibody fragment that is fused to a truncated form of *Pseudomonas* exotoxin A. Also encompassed by the invention are combination therapy methods, including the use of reduced dosages of chemotherapeutic agents, for the prevention or treatment of cancer. Also encompassed by the invention are formulations and methods for direct administration of the recombinant immunotoxin to the carcinoma, for the prevention or treatment of cancer.

18 Claims, 11 Drawing Sheets

(56) References Cited

OTHER PUBLICATIONS

Holm et al., Functional mapping and single chain construction of the anti-cytokeratin 8 monoclonal antibody TS1, *Mol Immunol.*, (Feb. 2007), 44(6): 1075-1084. Epub Sep. 20, 2006.
Kreitman, Immunotoxins in cancer therapy, *Curr Opin Immunol.*, (Oct. 1999), 11(5):570-578.
Kubetzko et al., Engineering of an EGP-2 (Ep-CAM) specific antibody-immunotoxin for targeted therapy of solid tumors, *Swiss Cancer Bulletin*, (2000), 20(4):182-187.
Lemaistre et al., An immunotoxin cytotoxic for breast cancer cells in vitro, *Cancer Res.*, (Feb. 1, 1987),47(3):730-734.
MacCallum et al., Antibody-antigen interactions: contact analysis and binding site topgraphy, *J Mol Biol.*, (Oct. 11, 1996), 262(5):732-745.
McLaughlin et al, The epithelial glycoprotein 2 (EGP-2) promoter-driven epithelial-specific expression of EGP-2 in transgenic mice: a new model to study carcinoma-directed immunotherapy, *Cancer Res.*, (May 15, 2001), 61(10):4105-4111.
Martin et al., Genetic and hormonal risk factors in breast cancer, *J Natl Cancer Inst.*, (Jul. 19, 2000), 92(14):1126-1135.
Mueller et al., Expresion of tissue factor by melanoma cells promotes efficient hematogenous metastasis, *Proc Natl Acad Sci USA*, (Dec. 15, 1992), 89(24):11832-11836.
Rudikoff et al., Single amino acid substitution altering antigen-binding specificity, *Proc Natl Acad Sci USA*, (Mar. 1982), 79(6):1979-1983.
Starling et al., In vivo efficacy of monoclonal antibody-drug conjugates of three different subisotypes which bind the human tumor-associated antigen defined by the KS1/4 monoclonal antibody, *Cancer Immunol Immunother.*, (1989), 28(3):171-178.
Strome et al., Interleukin 4 Receptor-directed Cytotoxin Therapy for Human Head and Neck Squamous Cell Carcinoma in Animal Models, *Clin Cancer Res.*, (Jan. 2002), 8(1):281-286.
Syrigos et al., Use of monoclonal antibodies for the diagnosis and treatment of bladder cancer, *Hybridoma*. (Jun. 1999), 18(3):219-224.
Thiesen et al., Selective killing of human bladder cancer cells by combined treatment with A and B chain ricin antibody conjugates, *Cancer Res.*, (Jan. 15, 1987), 47(2):419-423.
Vajdos et al., Comprehensive functional maps of antigen-binding site of an anti-ErbB2 antibody obtained with shotgun scanning mutagenesis, *J Mol Biol.*, (Jul. 5, 2002), 320(2):415-428.
Velders et al., The impact of antigen density and antibody affinity on antibody-dependent cellular cytotoxicity: relevance for immunotherapy of carcinomas, *Br J Cancer.*, (Aug. 1998), 78(4):478-483.
Wawrzynczak et al., Pharmacokinetics in the rat of a panel of immunotoxins made with abrin A chain, ricin A chain, gelonin, and momordin, *Cancer Res.*, (Dec. 1, 1990), 50(23):7519-7526.
Willuda et al., High thermal stability is essential for tumor targeting of antibody fragments: engineering of a humanized anti-epithelial glycoprotein-2 (epithelial cell adhesion molecule) single-chain Fv fragment, *Cancer Res.*, (Nov. 15, 1999), 59(22):5758-5767.
Winter et al., The epithelial cell adhesion molecule (Ep-CAM) as a morphoregulatory molecule is a tool in surgical pathology, *American Journal of Pathology*, (Dec. 2003), 163(6):2139-2148.
Wu et al., Humanization of murine monoclonal antibody by simultaneous optimization of framework and CDR residues, *J Mol Biol.*, (Nov. 19, 1999), 294(1):151-162.
Zimmermann et al., A novel immunotoxin recognising the epithelial glycoprotein-2 has potent antitumoural activity on chemotherapy-resistant lung cancer, *Cancer Immunol Immunother.*, (Mar. 1997), 44(1):1-9.
Zorzos et al., Espression of a cell surface antigent recognized by the monoclonal antibody AUA1 in bladder carcinoma: an immunohistochemical study, *Eur Urol.*, (1995), 28(3):251-254.

\* cited by examiner

FIGURE 3A

<u>GAA TTC</u> CTG CAG GTC TAT GGA ACG ATA AAT GCC CAT GAA AAT TCT ATT TCA AGG AGA
EcoRI |------------------------------ Ara B Promoter ------------------------------

CAG TCA TA ATG AAA TAC CTA TTG CCT ACG GCA GCC GCT GGA TTG TTA TTA CTC GCT GCC
----------------| M   K   Y   L   L   P   T   A   A   A   G   L   L   L   L   A   A
                |_____ Pel B Leader _____

CAA CCA GCG ATG GCG CAC CAT CAT CAC CAT CAC GAT ATC CAG ATG ACC CAG TCC CCG
 Q   P   A   M   A   H   H   H   H   H   H   D   I   Q   M   T   Q   S   P
_____|       His₆         |-------------- V_L Start
                 1            5                          10

TCC TCC CTG AGT GCT TCT GTT GGT GAC CGT GTT ACC ATC ACC TGC CGT TCC ACC AAA
 S   S   L   S   A   S   V   G   D   R   V   T   I   T   C   R   S   T   K
                                                                 |
   15              20              25                            30

TCC CTC CTG CAC TCC AAC GGT ATC ACC TAC CTT TAT TGG TAT CAA CAG AAA CCG GGT
 S   L   L   H   S   N   G   I   T   Y   L   Y   W   Y   Q   Q   K   P   G
 ─────────── CDR 1 (L) ───────────|
      35              40              45              50

AAA GCT CCG AAA CTT CTG ATC TAC CAG ATG TCC AAC CTG GCT TCC GGT GTT CCG TCT
 K   A   P   K   L   L   I   Y   Q   M   S   N   L   A   S   G   V   P   S
                         |────── CDR 2 (L) ──────|
      55              60              65              70

CGT TTC TCC AGT TCT GGT TCT GGT ACC GAC TTC ACC CTG ACC ATC TCT TCT CTG CAG
 R   F   S   S   S   G   S   G   T   D   F   T   L   T   I   S   S   L   Q
      75              80              85              90

CCG GAA GAC TTC GCT ACC TAC TAC TGC GCT CAG AAC CTG GAA ATC CCG CGT ACC TTC
 P   E   D   F   A   T   Y   Y   C   A   Q   N   L   E   I   P   R   T   F
                                     |────────── CDR 3 (L) ──────────
      95             100             105

GGT CAG GGT ACC AAA GTT GAA CTT AAG CGC GCT ACC CCG TCT CAC AAC TCC CAC CAG
 G   Q   G   T   K   V   E   L   K   R   A   T   P   S   H   N   S   H   Q
                    V_L End ----------|
     110             115             120             125

GTT CCA TCC GCA GGC GGT CCG ACT GCT AAC TCT GGA ACT AGT GGA TCC GAA GTA CAG
 V   P   S   A   G   G   P   T   A   N   S   G   T   S   G   S   E   V   Q
 ──────────────────────── Linker ────────────────────────| V_H Start ─
     130             135             140             145

CTG GTT CAG TCC GGC CCG GGT CTT GTT CAA CCG GGT GGT TCC GTT CGT ATC TCT TGC
 L   V   Q   S   G   P   G   L   V   Q   P   G   G   S   V   R   I   S   C
     150             155             160             165

FIGURE 3B

```
GCT GCT TCT GGT TAC ACG TTC ACC AAC TAC GGC ATG AAC TGG GTC AAA CAG GCT CCG
 A   A   S   G   Y   T   F   T   N   Y   G   M   N   W   V   K   Q   A   P
                         |—— CDR 1 (H) ——|
        170             175             180                 185

GGT AAA GGC CTG GAA TGG ATG GGC TGG ATC AAC ACC TAC ACC GGT GAA TCC ACC TAC
 G   K   G   L   E   W   M   G   W   I   N   T   Y   T   G   E   S   T   Y
                             |————————————— CDR 2 (H) —————————
        190                 195             200

GCT GAC TCC TTC AAA GGT CGC TTC ACT TTC TCC CTC GAC ACA AGT GCT AGT GCT GCA
 A   D   S   F   K   G   R   F   T   F   S   L   D   T   S   A   S   A   A
——————————————————|
205             210             215             220

TAC CTC CAA ATC AAC TCG CTG CGT GCA GAG GAT ACA GCA GTC TAT TAC TGC GCC CGT
 Y   L   Q   I   N   S   L   R   A   E   D   T   A   V   Y   Y   C   A   R
        225             230             235             240

TTC GCT ATC AAA GGT GAC TAC TGG GGT CAA GGC ACG CTG CTG ACC GTT TCC TCG GAA
 F   A   I   K   G   D   Y   W   G   Q   G   T   L   L   T   V   S   S   E
|———— CDR 3 (H) ————|                                                   |——
        245             250             255             260

TTT GGT GGC GCG CCG GAG TTC CCG AAA CCG TCC ACC CCG CCG GGT TCT TCT GGT TTA
 F   G   G   A   P   E   F   P   K   P   S   T   P   P   G   S   S   G   L
————————————————————————— Linker ————————————————————————————————|
        265             270             275             280

GAG GGC GGC AGC CTG GCC GCG CTG ACC GCG CAC CAG GCC TGC CAC CTG CCG CTG GAG
 E   G   G   S   L   A   A   L   T   A   H   Q   A   C   H   L   P   L   E
|—————————————— ETA₂₅₂₋₆₀₈ Start
        285             290             295

ACT TTC ACC CGT CAT CGC CAG CCG CGC GGC TGG GAA CAA CTG GAG CAG TGC GGC TAT
 T   F   T   R   H   R   Q   P   R   G   W   E   Q   L   E   Q   C   G   Y
300             305             310             315

CCG GTG CAG CGG CTG GTC GCC CTC TAC CTG GCG GCG CGA CTG TCA TGG AAC CAG GTC
 P   V   Q   R   L   V   A   L   Y   L   A   A   R   L   S   W   N   Q   V
        320             325             330             335

GAC CAG GTG ATC CGC AAC GCC CTG GCC AGC CCC GGC AGC GGC GGC GAC CTG GGC GAA
 D   Q   V   I   R   N   A   L   A   S   P   G   S   G   G   D   L   G   E
        340             345             350             355
```

FIGURE 3C

```
GCG ATC CGC GAG CAG CCG GAG CAG GCC CGT CTG GCC CTG ACC CTG GCC GCC GCC GAG
 A   I   R   E   Q   P   E   Q   A   R   L   A   L   T   L   A   A   A   E
         360             365             370             375

AGC GAG CGC TTC GTC CGG CAG GGC ACC GGC AAC GAC GAG GCC GGC GCG GCC AGC GCC
 S   E   R   F   V   R   Q   G   T   G   N   D   E   A   G   A   A   S   A
         380             385             390

GAC GTG GTG AGC CTG ACC TGC CCG GTC GCC GCC GGT GAA TGC GCG GGC CCG GCG GAC
 D   V   V   S   L   T   C   P   V   A   A   G   E   C   A   G   P   A   D
395             400             405             410

AGC GGC GAC GCC CTG CTG GAG CGC AAC TAT CCC ACT GGC GCG GAG TTC CTC GGC GAC
 S   G   D   A   L   L   E   R   N   Y   P   T   G   A   E   F   L   G   D
     415             420             425             430

GGT GGC GAC GTC AGC TTC AGC ACC CGC GGC ACG CAG AAC TGG ACG GTG GAG CGG CTG
 G   G   D   V   S   F   S   T   R   G   T   Q   N   W   T   V   E   R   L
         435             440             445             450

CTC CAG GCG CAC CGC CAA CTG GAG GAG CGC GGC TAT GTG TTC GTC GGC TAC CAC GGC
 L   Q   A   H   R   Q   L   E   E   R   G   Y   V   F   V   G   Y   H   G
         455             460             465             470

ACC TTC CTC GAA GCG GCG CAA AGC ATC GTC TTC GGC GGG GTG CGC GCG CGC AGC CAG
 T   F   L   E   A   A   Q   S   I   V   F   G   G   V   R   A   R   S   Q
             475             480             485

GAT CTC GAC GCG ATC TGG CGC GGT TTC TAT ATC GCC GGC GAT CCG GCG CTG GCC TAC
 D   L   D   A   I   W   R   G   F   Y   I   A   G   D   P   A   L   A   Y
490             495             500             505

GGC TAC GCC CAG GAC CAG GAA CCC GAC GCG CGC GGC CGG ATC CGC AAC GGT GCC CTG
 G   Y   A   Q   D   Q   E   P   D   A   R   G   R   I   R   N   G   A   L
     510             515             520             525

CTG CGG GTC TAT GTG CCG CGC TCC AGC CTG CCG GGC TTC TAC CGC ACC GGC CTG ACC
 L   R   V   Y   V   P   R   S   S   L   P   G   F   Y   R   T   G   L   T
         530             535             540             545

CTG GCC GCG CCG GAG GCG GCG GGC GAG GTC GAA CGG CTG ATC GGC CAT CCG CTG CCG
 L   A   A   P   E   A   A   G   E   V   E   R   L   I   G   H   P   L   P
         550             555             560             565
```

FIGURE 3D

```
CTG CGC CTG GAC GCC ATC ACC GGC CCC GAG GAG GAA GGC GGG CGC CTG GAG ACC ATT
 L   R   L   D   A   I   T   G   P   E   E   E   G   G   R   L   E   T   I
            570                 575                 580

CTC GGC TGG CCG CTG GCC GAG CGC ACC GTG GTG ATT CCC TCG GCG ATC CCC ACC GAC
 L   G   W   P   L   A   E   R   T   V   V   I   P   S   A   I   P   T   D
585                 590                 595                 600

CCG CGC AAC GTC GGT GGC GAC CTC GAC CCG TCC AGC ATC CCC GAC AAG GAA CAG GCG
 P   R   N   V   G   G   D   L   D   P   S   S   I   P   D   K   E   Q   A
    605                 610                 615                 620

ATC AGC GCC CTG CCG GAC TAC GCC AGC CAG CCC GGC AAA CCG CCG CAT CAC CAC CAT
 I   S   A   L   P   D   Y   A   S   Q   P   G   K   P   P   H   H   H   H
                                    ETA 252-608 End ----------|        His6
         625                 630                 635                 640

CAC CAT AAA GAC GAA CTG TAG TGA CTC GAG
 H   H   K   D   E   L   .   .   L   E
                                  XhoI
         645                 651
```

METHODS FOR TREATING CANCER USING AN IMMUNOTOXIN

RELATED APPLICATIONS

This continuation application claims the benefit of and priority to U.S. patent application Ser. No. 12/698,434 filed Feb. 2, 2010, which is a continuation of U.S. application Ser. No. 10/554,788 filed Nov. 13, 2006, which is a national phase of PCT/CA2004/000637 filed Apr. 30, 2004, which claims the benefit of U.S. Provisional Patent Application Ser. No. 60/466,608 filed Apr. 30, 2003.

FIELD OF THE INVENTION

The present invention is directed to methods for the prevention or treatment of cancer by administering to patients having cancer, or at risk of having cancer, an immunotoxin which binds to an antigen selectively expressed on the surface of cancer cells.

BACKGROUND OF THE INVENTION

Recently, immunotherapy has emerged as a potentially effective new approach to combat cancer, Murine and humanized/chimeric antibodies, and their respective antibody fragments, directed against tumor-associated antigens ("TAAs") have been used for diagnosis and therapy of certain human cancers.[5-13] Unconjugated, toxin-conjugated, and radiolabeled forms of these antibodies have been used in such therapies.

One tumor associated antigen of interest for immunotherapy is Ep-CAM (for Epithelial Cell Adhesion Molecule, which also known as 17-1A, KSA, EGP-2 and GA733-2). Ep-CAM is a transmembrane protein that is highly expressed in many solid tumors, including carcinomas of the lung, breast, ovary, colorectum, and squamous cell carcinoma of the head and neck, but weakly expressed in most normal epithelial tissues. The role of Ep-CAM in cancer formation remains unclear; however, its expression correlates with the rate of cellular proliferation. Ep-CAM-specific antibodies have been used to image and detect primary tumors and metastases in patients with small cell lung cancer and non-small cell lung cancer. Among anti-Ep-CAM MAbs, PANOREX®, which is a murine monoclonal antibody also known as edrecolomab, had been approved for the treatment of colon cancer in Germany, and is in clinical trials in the United States.[14-15] Of note, however, PANOREX® treatment has been associated with undesirable side effects, including abdominal cramps, nausea, transient diarrhea and cutaneous urticarial lesions.[39, 41, 51] Clinical trials with other Ep-CAM-targeted antibodies have been less successful; antibody 30 BIS-1 was associated with peripheral vasoconstriction, dyspnea and fever, and antibody 3622W94 was associated with acute necrotizing pancreatitis.[39-41, 57] The search for an effective, low-toxicity, anti-Ep-CAM antibody continues: a fully humanized anti-Ep-CAM antibody, MT201, purported to act via Antibody-Dependent Cellular Cytotoxicity ("ADCC"), has been reported.[58] A humanized, stabilized, single-chain, anti-Ep-CAM antibody, 4D5MOC-B, which is derived from murine monoclonal antibody MOC31, has also been developed, and is described in International Patent Application No. PCT/EP00/03176, Publication No. WO 00/61635, filed Apr. 10, 2000 and published Oct. 19, 2000, and in Willuda et al.[59] These publications do not disclose the use of the humanized antibody in the treatment of head and neck squamous cell carcinoma (HNSCC) or bladder cancer.

As stated above, one of the cancers associated with increased expression of Ep-CAM is squamous cell carcinoma of the head and neck ("HNSCC"). Ep-CAM expression correlates with the progression of squamous cell carcinoma of the head and neck in humans. HNSCC is presently the sixth most common cancer in the world. HNSCC is a disease that causes significant morbidity, especially with respect to speech and swallowing functions. Surgery, radiation therapy, chemotherapy, or combinations of these are generally available as treatment options.

Despite all attempts to cure patients afflicted with HNSCC, recurrence remains the most common cause of failure (in 40%-50% of patients) after head and neck cancer therapy. Salvage therapy consists of the same treatment options as for first line therapy. However, palliative surgery is often difficult and disfiguring. Furthermore, radiation therapy is rarely feasible or beneficial, and chemotherapy does not substantially improve survival rates in HNSCC patients. Prognosis for these patients remains poor, such that the median survival after recurrence is only approximately six months.

Due to the poor prognosis for HNSCC patients, the impact of the disease on quality of life, and the limited treatment options, there is considerable interest in, and a compelling need for, the development of new tumor-specific therapies, particularly directed to HNSCC.

Bladder cancer is the 7th most common cancer worldwide that results in an estimated 260,000 new cases each year. In Europe, this disease is the cause of death for approximately 50,000 people each year. Carcinomas in the bladder tissue occur almost entirely within the transitional epithelium, the surface layer of tissue that lines the bladder, as transitional cell carcinomas. At initial diagnosis, 70 to 90% of patients with bladder cancers have superficial disease which involves carcinomas in the superficial urothelial layer that are noninvasive and exhibit papillary (finger-like projections) tumors. Current treatment includes the intravesicular delivery of chemotherapy and immunotherapy with the bacille Calmette-*Guerin* (BCG) vaccine that involves the additional risk of systemic infection with the tuberculosis bacterium. Despite this aggressive treatment regime, 70% of these superficial papillary tumors will recur over a prolonged clinical course, causing significant morbidity; approximately 4 to 8% will progress to invasive carcinomas.

In response to this medical need, there is considerable need in the development of new, tumor-specific therapies. One novel approach is targeted therapy using an immunotoxin: an antibody conjugated with a toxin. The antibody binds specifically to tumor cells to deliver the toxin for efficient tumor cell-killing.

SUMMARY OF THE INVENTION

The present invention relates to novel methods for treating head and neck squamous cell carcinoma and bladder cancer by administering, to a patient in need of such treatment, an effective amount of a recombinant immunotoxin that specifically binds to (and therefore is "targeted to") a protein on the surface of the cancer cells. Where desired, the immunotoxin may be co-administered, concurrently administered, and/or sequentially administered with one or more other anti-cancer agents, and/or in conjunction with radiation or surgery.

The invention also relates to methods for preventing, preventing recurrence, or reducing the rate of recurrence, of a cancer, comprising directly administering an effective amount of an immunotoxin to a site of suspected occurrence or recurrence.

The invention also relates to methods for reducing the risk of post-surgical complications comprising administering directly to the surgical site an effective amount of an immunotoxin before, during, and/or after surgery for cancer.

The invention also relates to methods for sensitizing a tumor or cancer to another cancer therapeutic comprising administering an effective amount of an immunotoxin. The other cancer therapeutic may be administered prior to, overlapping with, concurrently, and/or after administration of the immunotoxin.

The immunotoxin used in the therapeutic methods of the invention comprises (a) a ligand that binds to a protein on the cancer cell attached to; (b) a toxin that is cytotoxic to the cancer cell. The cancer cell binding portion (a) may be linked to the toxin portion (b) by, for example, chemical linking or genetic linking.

In particular, non-limiting embodiments, the ligand binds Ep-CAM. In a specific, non-limiting embodiment, the ligand is an antibody or antibody fragment.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE FIGURES

The invention will now be described in relation to the drawings in which:

FIGS. 3A-D and SEQ ID NOS:1 and 2 show the DNA and Amino Acid Sequences of VB4-845. The nucleotide and polypeptide sequences can be divided into domains including: the signal sequence for periplasmic expression, histidine tags, CDR 1, 2 and 3 domains, VL domain, VH domain, linkers, ETA domains II, Ib, III, and an ER retention signal KDEL.

DEFINITIONS

Figure 1:
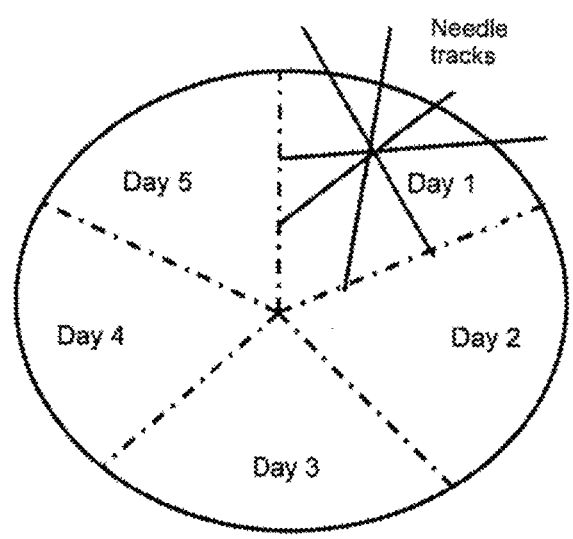
FIG. 1 is a schematic showing a template for the intratumoral administration of immunotoxin and/or other cancer therapeutic to a tumor mass FIG. 2. (A) Map of VB4-845. The map depicts the organization of the immunotoxin's linked 4D5MOCB scFv and ETA252-608 portions, as well as the various domains, including the histidine tags, PelB signal, linker regions, the Vl and Vh regions, ETA regions II, Ib, and III, and the ER retention signal. (B) Predictive Three-Dimensional Model of 4D5MOCB-ETA. The structure of the scFv (VL and VH), ETA252-608 (domains II, Ib, and III), the linking peptide, and both histidine tags are shown.

As used herein, the term "animal" includes all members of the animal kingdom, including humans. The animal is preferably a human with HNSCC or bladder cancer.

As used herein, the phrase "cancer therapeutic" refers to compounds or treatments that are effective in treating or preventing cancer including, without limitation, chemical agents, other immunotherapeutics, cancer vaccines, anti-angiogenic compounds, certain cytokines, certain hormones, gene therapy, radiotherapy, surgery, and dietary therapy.

As used herein, the phrase "effective amount" means an amount effective, at dosages and for periods of time necessary to achieve the desired result. Effective amounts of an immunotoxin may vary according to factors such as the disease state, age, sex, weight of the animal. Dosage regima may be adjusted to provide the optimum therapeutic response. For example, several divided doses may be administered daily or the dose may be proportionally reduced as indicated by the exigencies of the therapeutic situation.

As used herein, the phrase "humanized antibody or antibody fragment" means that the antibody or fragment comprises human framework regions. The humanization of antibodies from non-human species has been well described in the literature. See for example EP-B1 0 239400 and Carter& Merchant 1997 (Curr Opin Biotechnol 8,449-454, 1997).

As used herein, the phrase "the immunotoxin is administered directly to the cancer site" refers to direct or substantially direct introduction including, without limitation, single or multiple injections of the immunotoxin directly into the tumor or peritumorally, continuous or discontinuous perfusion into the tumor or peritumorally, introduction of a reservoir into the tumor or peritumorally, introduction of a slow-release apparatus into the tumor or peritumorally, introduction of a slow-release formulation into the tumor or peritumorally, direct application onto the tumor, direct injection into an artery that substantially directly feeds the area of the tumor, direct injection into a lymphatic vessel that substantially drains into the area of the tumor, direct or substantially direct introduction in a substantially enclosed cavity (e.g., pleural cavity) or lumen (e.g., intravesicular). "Peritumoral" is a term that describes a region, within about 10 cm, preferably within 5 cm, more preferably within 1 cm, of what is regarded as the tumor boundary, such as, but not limited to, a palpable tumor border. "Direct administration" in the context of prevention of occurrence or prevention of recurrence is defined as administration directly into a site at risk for development or recurrence of a cancer.

As used herein, the phrase "ligand that binds to a protein on the cancer cell" includes any molecule that can selectively target the immunotoxin to the cancer cell by binding to a protein on the cancer cells. The targeted protein on the cancer cell is preferably a tumor associated antigen that is expressed at higher levels on the cancer cell as compared to normal cells.

As used herein, the term "MOC-31 antibody" means the murine anti-Ep-CAM or anti-EGP-2 antibody that is known in the art and is available from commercial sources such as BioGenex, cat no. MU316-UC, Zymed Laboratories Inc., cat. No. 18-0270 or United States Biological, cat no. M4165.

As used herein, the term "4D5MOC-A" means the humanized scFv MOC31 antibody that was grafted onto the artificial human consensus framework of scFv 4D5 as described in WO 00/61635 which is incorporated herein by reference.

As used herein, the term "4D5MOC-B" means a stable variant of 4D5MOC-A that was prepared as described in WO 00/61635 which is incorporated herein by reference.

As used herein, the term "VB4-845" means an immunotoxin that comprises a) the scFv humanized antibody 4D5MOC-B that is fused to b) a truncated form of *Pseudomonas* exotoxin A that consists of amino acids 252-608.

As used herein, the phrase "pharmaceutically acceptable" refers to general clinical use and/or approval by a regulatory agency of the Federal or state government, listing in the United States Pharmacopoeia, or general acceptance by those skilled in the relevant art.

As used herein, "physiologic conditions" for antibody binding reflect but do not necessarily exactly duplicate the conditions in which an Ep-CAM-binding polypeptide would encounter an Ep-CAM molecule in vivo. Binding under physiologic conditions should be reasonably predictive that binding in vivo will occur.

As used herein, the phrase "preventing cancer" refers to prevention of cancer occurrence. In certain instances, the preventative treatment reduces the recurrence of the cancer. In other instances, preventative treatment decreases the risk of a patient from developing a cancer, or inhibits progression of a pre-cancerous state (e.g. acolon polyp) to actual malignancy.

As used herein, the phrase "reduced dose" refers to a dose that is below the normally administered and/or recommended dose. The normally administered dose of a cancer therapeutic can be found in reference materials well known in the art such as, for example, the latest edition of the Physician's Desk Reference.

As used herein, the phrase "treating cancer" refers to inhibition of cancer cell replication, inhibition of cancer spread (metastasis), inhibition of tumor growth, reduction of cancer cell number or tumor growth, decrease in the malignant grade of a cancer (e.g., increased differentiation), or improved cancer-related symptoms.

As used herein, the term "variant" refers to any pharmaceutically acceptable derivative, analogue, or fragment of an immunotoxin, an antibody or antibody fragment, a toxin (e.g., *Pseudomonas* toxin), or cancer therapeutic described herein, A variant also encompasses one or more components of a multimer, multimers comprising an individual component, multimers comprising multiples of an individual component (e.g., multimers of a reference molecule), a chemical breakdown product, and a biological breakdown product. In particular, non-limiting embodiments, an immunotoxin may be a "variant" relative to a reference immunotoxin by virtue of alteration(s) in the Ep-CAM-binding portion and/or the toxin portion of the reference immunotoxin. For example, a variant immunotoxin may contain multimers of the antibody portion and/or the toxin portion. A variant of the toxin portion of the molecule retains toxicity of at least 10 percent and preferably at least 30 percent in a standard assay used to measure toxicity of a preparation of the reference toxin.

A variant immunotoxin having a variation of the Ep-CAM-binding portion of the reference immunotoxin competes with the binding of an anti-Ep-CAM reference antibody, under physiologic conditions, by at least 10 percent and preferably at least 30 percent (and see infra). Competition by 10 percent means that, in an assay where a saturating concentration of anti-Ep-CAM reference antibody is bound to Ep-CAM, 10 percent of these bound reference antibodies is displaced when an equilibrium is reached with an equivalent concentration of the variant anti-Ep-CAM immunotoxin being tested. As a non-limiting example, competition between antibodies, or between an antibody and an immunotoxin, is measured by (1) binding labeled anti-Ep-CAM reference antibody to Ep-CAM on the surface of cells, or to an Ep-CAM-coated solid substrate, such that virtually all Ep-CAM sites are bound by the antibody; (2) contacting these antibody-antigen complexes with unlabeled test anti-Ep-CAM antibody or unlabeled test immunotoxin; and (3) measuring the amount of labeled antibody displaced from Ep-CAM binding sites, wherein the amount of freed, labeled antibody indicates the amount of competition that has occurred.

DETAILED DESCRIPTION OF THE INVENTION

The inventors have shown that an immunotoxin comprising a humanized antibody fragment that binds to the extracellular domain of human Ep-CAM linked to *Pseudomonas* exotoxin A is effective in treating both head and neck squamous cell carcinoma (HNSCC) and bladder cancer. In particular, the inventors have shown that an immunotoxin comprising a single-chain Fv recombinant stabilized and humanized antibody fragment to Ep-CAM that has been fused to a truncated form of *Pseudomonas* Exotoxin A (ETA) which lacks the cell binding domain is cytotoxic against both HNSCC and bladder cancer cells. This immunotoxin binds to Ep-CAM expressed on the cancer cells. Once bound, the immunotoxin is internalized and the *Pseudomonas* Exotoxin A blocks the protein synthesis, therein leading to cell death. Importantly, since most normal mucosal cells and fibroblasts do not widely express Ep-CAM, and therefore cannot internalize the immunotoxin, they are protected from the killing effect of the exotoxin.

Accordingly, in one embodiment, the present invention provides a method for treating or preventing head and neck squamous cell carcinoma comprising administering to an animal in need of such treatment an effective amount of an immunotoxin comprising: (a) a ligand that binds to a protein on the cancer cell attached to; (b) a toxin that is cytotoxic to the cancer cells. The present invention also provides a use of an effective amount of an immunotoxin comprising: (a) a ligand that binds to a protein on the cancer cell attached to; (b) a toxin that is cytotoxic to the cancer cells to treat or prevent head and neck squamous cell carcinoma. The present invention further provides a use of an effective amount of an immunotoxin comprising: (a) a ligand that binds to a protein on the cancer cell attached to; (b) a toxin that is cytotoxic to the cancer cells in the manufacture of a medicament to treat or prevent head and neck squamous cell carcinoma.

In another embodiment, the present invention provides a method for treating or preventing bladder cancer comprising administering to an animal in need of such treatment an effective amount of an immunotoxin comprising: (a) a ligand that binds to a protein on the cancer cell attached to; (b) a toxin that is cytotoxic to the cancer cells. The present invention also provides a use of an effective amount of an immunotoxin comprising: (a) a ligand that binds to a protein on the cancer cell attached to; (b) a toxin that is cytotoxic to the cancer cells to treat or prevent bladder cancer. The present invention further provides a use of an effective amount of an immunotoxin comprising: (a) a ligand that binds to a protein on the cancer cell attached to; (b) a toxin that is cytotoxic to the cancer cells in the manufacture of a medicament to treat or prevent bladder cancer.

The ligand that binds to a protein on the cancer cell can be any molecule that can selectively target the immunotoxin to the cancer cells. In one embodiment, the ligand binds to a tumor associated antigen. Examples of proteins that are expressed on HNSCC cells include IL-4 receptor, the EGF-receptor, the HER21 neu surface protein and Ep-CAM. Examples of proteins that are expressed on bladder cancer cells include EGF-receptor, gp54 and Ep-CAM, In a specific embodiment, the ligand binds to Ep-CAM.

In a preferred embodiment, the ligand is an antibody or antibody fragment. Antibody fragments that may be used include Fab[1], Fab', F(ab')$_2$, scFv and dsFv fragments from recombinant sources and/or produced in transgenic animals. The antibody or fragment may be from any species including mice, rats, rabbits, hamsters and humans. Chimeric antibody derivatives, i.e., antibody molecules that combine a non-human animal variable region and a human constant region are also contemplated within the scope of the invention. Chimeric antibody molecules can include, for example, humanized antibodies which comprise the antigen binding domain from an antibody of a mouse, rat, or other species, with human constant regions. Conventional methods may be used to make chimeric antibodies. (See, for example, Morrison et al., Proc. Natl. Acad. Sci. U.S.A. 81, 6851 (1985); Takeda et al., Nature 314, 452 (1985), Cabilly et al., U.S. Pat. No. 4,816,567; Boss et al., U.S. Pat. No. 4,816,397; Tanaguchi et al., European Patent Publication EP171496; European Patent Publication 0173494, United Kingdom patent GB 2177096B). The preparation of humanized antibodies is described in EP-B 10 239400. Humanized antibodies can also be commercially produced (Scotgen Limited, 2 Holly Road, Twickenham, Middlesex, Great Britain.). It is expected that chimeric antibodies would be less immunogenic in a human subject than the corresponding non-chimeric antibody. The humanized antibodies can be further stabilized for example as described in WO 00/61635.

Specific antibodies, or antibody fragments, reactive proteins on HNSCC or bladder cancer cells may also be generated by screening expression libraries encoding immunoglobulin genes, or portions thereof, expressed in bacteria with peptides produced from the nucleic acid molecules encoding the proteins. For example, complete Fab fragments, VH regions and FV regions can be expressed in bacteria using phage expression libraries (See for example Ward et al., Nature 341, 544-546: (1989); Huse et al., Science 246, 1275-1281 (1989); and McCafferty et al. Nature 348, 552-554 (1990)). Alternatively, a SCID-hu mouse, for example the model developed by Genpharm, can be used to produce antibodies or fragments thereof.

The ligand portion of the immunotoxin may be immunoglobulin derived, i.e., can be traced to a starting molecule that is an immunoglobulin (or antibody). For example, the ligand may be produced by modification of an immunoglobulin scaffold using standard techniques known in the art. In another, non-limiting example, immunoglobulin domains (e.g., variable heavy and/or light chains) may be linked to a non-immunoglobulin scaffold. Further, the ligand may be developed by, without limitation, chemical reaction or genetic design. Accordingly, in a non-limiting example, an immunotoxin may comprise (1) an immunoglobulin-derived polypeptide (e.g., an antibody selected from an antibody library), or variant thereof, that specifically binds to HNSCC or bladder cancer cells, and (2) a toxin or variant thereof. Such immunoglobulin polypeptide ligands can be re-designed to affect their binding characteristics to a target a tumor associated molecule, or to improve their physical characteristics, for example.

The ligand portion of the immunotoxin need not be immunoglobulin based. Accordingly, an immunotoxin may comprise (1) a non-immunoglobulin polypeptide (e.g., Affibody®), or variant thereof, that specifically binds to HNSCC or bladder cancer cells, and (2) a toxin or variant thereof. Such non-immunoglobulin polypeptide ligands can be designed to bind to a target tumor associated molecule. Moreover, non-immunoglobulin polypeptide ligands can be engineered to a desired affinity or avidity, and can be designed to tolerate a variety of physical conditions, including extreme pH ranges and relatively high temperature.

Indeed, for use in a pharmaceutical composition, the design of a non-immunoglobulin polypeptide with a relatively long half-life at physiological conditions (e.g., 37° C. in the presence of peptidases) can be advantageous. Furthermore, such molecules, or variants thereof, may demonstrate good solubility, small size, proper folding and can be expressed in readily available, low-cost bacterial systems, and thus manufactured in commercially reasonable quantities. The ability to design a non-immunoglobulin polypeptide is within the skill of the ordinary artisan. See, e.g., U.S. Pat. Nos. 5,831,012 and 6,534,628 for techniques generally adaptable to design, manufacture, and select desired binding partners.

Examples of epitope-binding polypeptides include, without limitation, ligands comprising a fibronectin type III domain (see, e.g., International Publication Nos. WO 01/64942, WO 00/34784, WO 02/32925). Protein A-based affinity libraries have also been used to identify epitope-binding polypeptides (see, e.g., U.S. Pat. Nos. 5,831,012 and 6,534,628) and such libraries may be useful in accordance with the present invention to select polypeptides that selectively bind to HNSCC or bladder cancer cells.

Other types of binding molecules are known in the art including, without limitation, binding molecules based on assembly of repeat protein domains (see, e.g., Forrer et al., 2003, "A novel strategy to design binding molecules harnessing the modular nature of repeat proteins." FEBS Lett. 539: 2-6; Kohl et al., 2003, "Designed to be stable: crystal structure of a consensus ankyrin repeat protein." Proc Natl Acad Sci USA. 100:1700-1705). Libraries of randomly assembled repeat domains may be useful in accordance with the present invention to select ligands that selectively bind to HNSCC or bladder cancer cells.

Several non-immunoglobulin based, epitope-binding polypeptides and methods for making and using such polypeptides are known in the art (see, e.g., Eklund et al., 2002, "Anti-idiotype protein domains selected from Protein A-based affibody libraries." Prot, Struct. Funct. Gen. 48:454-462; Gunneriusson et al., 1999, "Affinity maturation of a Taq DNA polymerase specific affibody by helix shuffling." Prot. Eng. 12:873-878; Hansson et al., 1999, "An in vitro selected binding protein (affibody) shows conformation-dependent recognition of the respiratory syncytial virus (RSV) G protein." Immunotechnol. 4: 237-252; Henning et al., 2002, "Genetic modification of adenovirus 5 tropism by a novel class of ligands based on a three-helix bundle scaffold derived from staphylococcal protein A." Human Gene Therapy 13:1427-1439; Högbom et al., 2003, "Structural basis for recognition by an in vitro evolved affibody. Proc Natl Acad Sci USA. 100(6):3191-3196; Nord et al., 1997, "Binding proteins selected from combinatorial libraries of an-helical bacterial receptor domain." Nature Biotechnol. 15:772-777; Nord et al., 2000, "Ligands selected from combinatorial libraries of protein A for use in affinity capture of apolipoprotein A-1M and Taq DNA polymerase." J. Biotechnol. 80:45-54; Nord et al., 1995, "A combinatorial library of an alpha-helical bacterial receptor domain." Prot. Eng. 8:601-608; Nord et al., 2001, "Recombinant human factor VIII-specific affinity ligands selected from phage-displayed combinatorial libraries of protein A." Eur. J. Biochem. 268:1-10;

Nygren et al., 1997, "Scaffolds for engineering novel binding sites in proteins." Curr. Opin. Struct. Biol. 7:463-469; Rönnmark et al., 2002, "Human immunoglobin A (IgA)-specific ligands from combinatorial engineering of protein A." Eur. J. Bioehem. 269:2647-2655; Rönnmark et al., 2002, "Construction and characterization of affibody-Fc chimeras produced in *Escherichia coli*." J, Immunol. Meth. 261:199-211; Wahlberg et al., 2003, "An affibody in complex with a target protein: structure and coupled folding." Proc Natl Acad Sci USA. 100(6):3185-3190; Gotz et al., 2002, "Ultrafast electron transfer in the complex between fluorescein and a cognate engineered lipocalin protein, a so-called anticalin." Biochemistry. 41:4156-4164; Skerra, 2001, "Anticalins: a new class of engineered ligand-binding proteins with antibody-like properties." J. Biotechnol. 2001 74:257-275; Skerra, 2000, "Lipocalins as a scaffold." Biochim Biophys Acta. 1482:337-350; Skerra et al., 2000, "Engineered protein scaffolds for molecular recognition." J Mol. Recognit. 13:167-187; Schlehuber et al., 2000, "A novel type of receptor protein, based on the lipocalin scaffold, with specificity for digoxigenin." J Mol. Biol. 297:1105-1120; Beste et al., 1999, "Small antibody-like proteins with prescribed ligand specificities derived from the lipocalin fold." Proc Natl Acad Sci USA. 96:1898-1903; PCT International Publication No. WO97/45538 entitled "Novel Synthetic Protein Structural Templates For The Generation, Screening And Evolution Of Functional Molecular Surfaces" (relating to production of libraries of peptide sequences in the framework of a structural template derived from Pleckstrin-Homology (PH) domains)).

Cancers that may be treated according to the invention include, without limitation, any type of HNSCC or bladder cancer provided that the affected cells exhibit increased expression of a protein that can be targeted at the cell surface. Tumors or tumor cells may be evaluated to determine their susceptibility to the treatment methods of the invention by, for example, obtaining a sample of tumor tissue or cells and determining the ability of the sample to bind to the ligand portion of the immunotoxin. In one embodiment, the protein on the cancer cells is Ep-CAM. Cell-surface expression of Ep-CAM may be induced, or elevated, by an agent that increases steady-state levels of cell-surface Ep-CAM in pre-cancerous or cancerous tissue.

Accordingly, the present invention includes diagnostic methods and kits that can be used prior to the therapeutic method of the invention in order to determine whether or not the HNSCC or bladder cancer expresses levels of the protein that is bound by the ligand in the immunotoxin. Therefore, in a further embodiment, the present invention includes a method for treating or preventing head and neck squamous cell carcinoma or bladder cancer comprising:

(1) testing a tumor sample from a patient for the expression of a protein suspected of being associated with the head and neck squamous cell carcinoma or bladder cancer; and (2) if the protein is expressed at greater levels in the tumor sample as compared to a control, administering to the patient an effective amount of immunotoxin comprising:
   (a) a ligand that binds to the protein on the cancer cell attached to;
   (b) a toxin that is cytotoxic to the cancer cell.

The present invention further includes a kit for diagnosing head and neck squamous cell carcinoma or bladder cancer comprising a ligand that binds to a protein on the cancer cell and instructions for the use thereof to diagnose the cancer.

In preferred non-limiting embodiments, the cancer is amenable to treatment by direct administration of the immunotoxin. For example, a target tumor mass may be close to the surface of the skin. In another example, a diseased tissue may be encapsulated by a cyst, or is found in a substantially enclosed cavity including, without limitation, a lumen (e.g., bladder). (Further details on direct administration are provided later in the disclosure.)

In other embodiments, the cancer is amenable to treatment by intravenous administration of the immunotoxin.

The invention also provides methods for reducing the risk of post-surgical complications comprising administering an effective amount of an immunotoxin before, during, or after surgery, and in specific non-limiting embodiments, surgery to treat cancer.

The invention also provides methods for preventing occurrence, preventing or delaying recurrence, or reducing the rate of recurrence of HNSCC or bladder cancer comprising directly administering to a patient in need thereof an effective amount of an immunotoxin.

The invention also provides methods for sensitizing a tumor or cancer to one or more other cancer therapeutics comprising administering an immunotoxin of the invention. In a nonlimiting embodiment, the other cancer therapeutic comprises another Ep-CAM-targeted immunotoxin. In another nonlimiting embodiment, the other cancer therapeutic comprises radiation. The other cancer therapeutic may be administered prior to, overlapping with, concurrently, and/or after administration of the immunotoxin. When administered concurrently, the immunotoxin and other cancer therapeutic may be administered in a single formulation or in separate formulations, and if separately, then optionally, by different modes of administration. Accordingly, the combination of one or more immunotoxins and one or more other cancer therapeutics may synergistically act to combat the tumor or cancer.

Where an immunotoxin of the invention is administered in addition to one or more other therapeutic agents, these other cancer therapeutics may include, without limitation, 2,2', 2"trichlorotriethylamme, 6-azauridine, 6-diazo-5-oxo-L-norleucine, 6-mercaptopurine, aceglarone, aclacinomycinsa actinomycin, altretamine, aminoglutethimide, aminoglutethimide, amsacrine, anastrozole, ancitabine, angiogenin antisense oligonucleotide, anthramycin, azacitidine, azaserine, aziridine, batimastar, bcl-2 antisense oligonucleotide, benzodepa, bicalutamide, bisantrene, bleomycin, buserelin, busulfan, cactinomycin, calusterone, carboplatin, carboquone, carmofur, carmustine, carubicin, carzinophilin, chlorambucil, chloraphazine, chlormadinone acetate, chlorozotocin, chromomycins, cisplatin, cladribine, cyclophosphamide, cytarabine, dacarbazine, dactinomycin, daunorubicin, defosfamide, demecolcine, denopterin, diaziquone, docetaxel, doxifluridine, doxorubicin, droloxifene, dromostanolone, edatrexate, eflomithine, elliptinium acetate, emitefur, enocitabune, epirubicin, epitiostanol, estramustine, etoglucid, etoposide, fadrozole, fenretinide, floxuridine, fludarabine, fluorouracil, flutamide, folinic acid, formestane, fosfestrol, fotemustine, gallium nitrate, gemcitabine, goserelin, hexestrol, hydroxyurea, idarubicin, ifosfamide, improsulfan, interferon-alpha, interferon-beta, interferon-gamma, interleukin-2, L-asparaginase, lentinan, letrozole, leuprolide, lomustine, lonidamine, mannomustine, mechlorethamine, mechlorethamine oxide hydrochloride, medroxyprogesterone, megestrol acetate, melengestrol, melphalan, menogaril, mepitiostane, methotrexate, meturedepa, miboplatin, miltefosine, mitobronitol, mitoguazone, mitolactol, mitomycins, mitotane, mitoxantrone, mopidamol, mycophenolic acid, nilutamide, nimustine, nitracine, nogalamycin, novembichin, ollvomycins, oxaliplatin, paclitaxel, pentostain, peplomycin, perfosfamide, phenamet, phenesterine, pipobroman, piposulfan, pirarubicin, piritrexim, plicamycln, podophyllinic acid 2-ethyl-hydrazide, polyestradiol phosphate, porfimer sodium, porfiromycin, prednimustine, procabazine, propagermanium, PSK, pteropterin, puromycin, ranimustine, razoxane, roquinimex, sizofican, sobuzoxane, spirogermanium, streptonigrin, streptozocin, tamoxifen, tegafur, temozolomide, teniposlde, tenuzonic acid, testolacone, thiamiprine, thioguanine, Tomudex, topotecan, toremifene, triaziquone, triethylenemelamine, triethylenephosphoramide, triethylenethiophosphoramide, trilostane, trimetrexate, triptorelin, trofosfamide, trontecan, tubercidin, ubenimex, uracil mustard, uredepa, urethan, vinblastine, vincristine, zinostatin, and zorubicin, cytosine arabinoside, gemtuzumab, thioepa, cyclothosphamide, antimetabolites (e.g., methotrexate, 6-mercaptopurine, 6-thioguanine, cytarabine, 5-fluorouracil, fludarabine, gemcitabine, dacarbazine, temozoamide), hexamethylmelamine, LYSODREN, nucleoside analogues, plant alkaloids (e.g., Taxol, paclitaxel, camptothecin, topotecan, irinotecan (CAMPTOSAR, CPT-11), vincristine, vinca alkyloids such as vinblastine.) podophyllotoxin, epipodophyllotoxin, VP-16 (etoposide), cytochalasin B, gramicidin D, ethidium bromide, emetine, anthracyclines (e.g., daunorubicin), doxorubicin liposomal, dihydroxyanthracindione, mithramycin, actinomycin D, aldesleukin, allutamine, biaomycin, capecitabine, carboplain, chlorabusin, cyclarabine, daclinomycin, floxuridhe, lauprolide acetate, levamisole, lomusline, mercaptopurino, mesna, mitolanc, pegaspergase, pentoslatin, picamycin, riuxlmab, campath-1, straplozocin, tretinoin, VEGF antisense oligonucleotide, vindesine, and vinorelbine. Compositions comprising one or more cancer therapeutics (e.g., FLAG, CHOP) are also contemplated by the present invention. FLAG comprises fludarabine, cytosine arabinoside (Ara-C) and G-CSF. CHOP comprises cyclophosphamide, vincristine, doxorubicin, and prednisone. For a full listing of cancer therapeutics known in the art, see, e.g., the latest editions of The Merck Index and the Physician's Desk Reference. Likewise, the immunotoxin of the invention may be used in conjunction with radiation therapy or other known cancer therapeutic modalities.

Pharmaceutical compositions for combination therapy may also include, without limitation, antibiotics (e.g., dactinomycin, bleomycin, mithramycin, anthramycin), asparaginase, *Bacillus* and *Guerin*, diphtheria toxin, procaine, tetracaine, lidocaine, propranolol, anti-mitotic agents, abrin, ricinA, *Pseudomonas* exotoxin, nerve growth factor, platelet derived growth factor, tissue plasminogen activator, antihistaminic agents, anti-nausea agents, etc.

Indeed, direct administration of an effective amount of an immunotoxin to a patient in need of such treatment may result in reduced doses of another cancer therapeutic having clinically significant efficacy. Such efficacy of the reduced dose of the other cancer therapeutic may not be observed absent administration with an immunotoxin. Accordingly, the present invention provides methods for treating a tumor or cancer comprising administering a reduced dose of one or more other cancer therapeutics.

Moreover, combination therapy comprising an immunotoxin to a patient in need of such treatment may permit relatively short treatment times when compared to the duration or number of cycles of standard treatment regimens. Accordingly, the present invention provides methods for treating a tumor or cancer comprising administering one or more other cancer therapeutics for relatively short duration and/or in fewer treatment cycles.

Thus, in accordance with the present invention, combination therapies comprising an immunotoxin and another cancer therapeutic may reduce toxicity (i.e., side effects) of the overall cancer treatment. For example, reduced toxicity, when compared to a monotherapy or another combination therapy, may be observed when delivering a reduced dose of immunotoxin and/or other cancer therapeutic, and/or when reducing the duration of a cycle (i.e., the period of a single administration or the period of a series of such administrations), and/or when reducing the number of cycles.

In a preferred embodiment, the invention provides methods for treating and/or ameliorating the clinical condition of patients suffering from HNSCC. Accordingly, the invention provides methods for (i) decreasing the HNSCC tumor size, growth rate, invasiveness, malignancy grade, and/or risk of recurrence, (ii) prolonging the disease-free interval following treatment, and/or (iii) improving breathing, swallowing, and/or speech function in a patient with HNSCC, comprising administering to the patient an effective amount of an immunotoxin. Clinical improvement may be subjectively or objectively determined, for example by evaluating the ability of a subject to breathe with less difficulty, the ability of the subject to swallow liquids versus solids, the degree of obstruction, the quality or volume of speech, and other indices known to the clinical arts.

In another preferred embodiment, the invention provides methods for treating and/or ameliorating the clinical condition of patients suffering from superficial transitional cell carcinoma of the bladder. Accordingly, the invention provides methods for (i) decreasing the bladder carcinoma tumor size, growth rate, invasiveness, malignancy grade, and/or risk of recurrence, (ii) prolonging the disease-free interval following other treatment, and/or (iii) curing the disease in a patient with transitional cell carcinoma of the bladder, comprising administering to the patient an effective amount of an immunotoxin. Clinical improvement may be determined, for example by cytological evaluation, cytoscopy or biopsy in a manner known to the clinical arts.

As mentioned previously, an immunotoxin of the invention comprises: (a) a ligand that binds to a protein on the cancer cell attached to; (b) a toxin that is cytotoxic to the cancer cell. The ligand may be "attached" to the target by any means by which the ligand can be associated with, or linked to, the toxin. For example, the ligand may be attached to the toxin by chemical or recombinant means. Chemical means for preparing fusions or conjugates are known in the art and can be used to prepare the immunotoxin. The method used to conjugate the ligand and toxin must be capable of joining the ligand with the toxin without interfering with the ability of the ligand to bind to the target molecule on the cancer cell.

In one embodiment, the ligand and toxin are both proteins and can be conjugated using techniques well known in the art. There are several hundred crosslinkers available that can conjugate two proteins. (See for example "Chemistry of Protein Conjugation and Crosslinking". 1991, Shans Wong, CRC Press, Ann Arbor). The crosslinker is generally chosen based on the reactive functional groups available or inserted on the ligand or toxin. In addition, if there are no reactive groups a photoactivatible crosslinker can be used. In certain instances, it may be desirable to include a spacer between the ligand and the toxin. Crosslinking agents known to the art include the homobifunctional agents: glutaraldehyde, dimethyladipimidate and Bis(diazobenzidine) and the heterobifunctional agents: m Maleimidobenzoyl-N-Hydroxysuccinimide and Sulfo-m Maleimidobenzoyl-N-Hydroxysuccinimide.

A ligand protein-toxin protein fusion may also be prepared using recombinant DNA techniques. In such a case a DNA sequence encoding the ligand is fused to a DNA sequence encoding the toxin, resulting in a chimeric DNA molecule. The chimeric DNA sequence is transfected into a host cell that expresses the ligand-toxin fusion protein. The fusion protein can be recovered from the cell culture and purified using techniques known in the art.

Preferably, the ligand binds to Ep-CAM, In one embodiment, the immunotoxin comprises (a) an antibody or antibody fragment that binds to Ep-CAM on the cancer cell attached to; (b) a toxin that is cytotoxic to the cancer cells. (This immunotoxin is sometimes referred to as "Ep-CAM-targeted immunotoxin" herein.) In a specific embodiment, the immunotoxin comprises (a) a humanized antibody or antibody fragment that binds to the extracellular domain of human Ep-CAM and comprises complementarity determining region (CDR) sequences derived from a MOC-31 antibody attached to; (b) a toxin that is cytotoxic to the cancer cells. CDR sequences from the 4D5MOC-B antibody are shown in SEQ ID NOS:4-9.

Suitable Ep-CAM-targeted immunotoxins according to the invention include, without limitation, VB4-845 and variants thereof, other immunotoxins that comprise the MOC31 variable region or variants thereof, as well as immunotoxins that comprise other single or double chain immunoglobulins that selectively bind Ep-CAM, or variants thereof.

In one embodiment, the Ep-CAM-binding portion comprises a complete immunoglobulin molecule. In another embodiment, the Ep-CAM-binding portion is a dimer of Fab, Fab', scFv, single-domain antibody fragments, or disulfide-stabilized Fv fragments. In another embodiment, the Ep-CAM-binding portion comprises a variable heavy chain, variable light chain, Fab, Fab', scFv, single-domain antibody fragment, or disulfide-stabilized Fv fragment. Portions of the Ep-CAM-binding molecule may be derived from one or more species, preferably comprising portions derived from the human species, and most preferably are completely human or humanized. Regions designed to facilitate purification or for conjugation to toxin may also be included in or added to the Ep-CAM-binding portion.

In a specific, non-limiting embodiment, the immunotoxin comprises VB4-845 as shown in SEQ ID NO:2, In other non-limiting embodiments, the immunotoxin comprises a variant of VB4-845. A VB4-845 variant binds to the same Ep-CAM epitope or to a substantially similar Ep-CAM epitope that is bound by VB4-845, and the variant may competitively inhibit VB4-845 binding to Ep-CAM, under physiologic conditions, by at least 10%, 15%, 20%, 25%, 30%, 35%, 40%, 45%, 50%, 55%, 60%, 65%, 70%, 75%, 80%, 85%, 90%, or 95%. A VB4-845 variant may comprise the same *Pseudomonas* exotoxin A fragment as VB4-845, or may comprise a different portion of the same exotoxin or a different toxin.

In another non-limiting embodiment, the immunotoxin comprises an Ep-CAM-binding portion comprising the variable region of MOC31, or a variant thereof. In yet another embodiment, the immunotoxin comprises an Ep-CAM-binding portion comprising 4D5MOCB, or a variant thereof. Binding of any of these immunotoxins to Ep-CAM may be reduced by at least 10%, 15%, 20%, 25%, 30%, 35%, 40%, 45%, 50%, 55%, 60%, 65%, 70%, 75%, 80%, 85%, 90%, or 95% by competition with the reference MOC31 or 4D5MOCB antibody under physiologic conditions. The affinity of VB4-845 is $K_D=1.6\times10^{-8}$, using indirect flow cytometry on live cells. Lineweaver-Burke analysis (data Notebook: 0935, page 50) was performed using method of Benedict et al (1997). J. Immunol. Methods, 201:223-231. The affinity of MOC31B, as described in Willuda et al (Cancer Research 59, 5758-5767, 1999) is $K_D=3.9\times10^{-9}$, measured using RIA and Biacore as described in methods. Consequently, the present invention includes immunotoxins having a dissociation constant ($K_D$) of less than $2.0\times10^{-8}$.

Alternatively, the immunotoxin comprises an Ep-CAM-binding portion other than those discussed in the preceding paragraphs, but which selectively binds to Ep-CAM. In a preferred embodiment, the binding affinity of said Ep-CAM-binding portion is at least four orders of magnitude, preferably at least three orders of magnitude, more preferably less than two orders of magnitude of the binding affinity of VB4-845, PANOREX®, or MT-201 as measured by standard laboratory techniques. In non-limiting embodiments, the Ep-CAM-binding portion may competitively block the binding of a known anti-Ep-CAM antibody, such as, but not limited to, PANOREX® or MT201, to Ep-CAM, under physiologic conditions, by at least 0.1%, 1%, 10%, 15%, 20%, 25%, 30%, 35%, 40%, 45%, 50%, 55%, 60%, 65%, 70%, 75%, 80%, 85%, 90%, or 95%.

The skilled artisan would appreciate that specificity determining residues can be identified. The term "specificity determining residue," also known as "SDR," refers to a residue that forms part of the paratope of an antibody, particularly CDR residues, the individual substitution of which by alanine, independently of any other mutations, diminishes the affinity of the antibody for the epitope by at least 10 fold, preferably by at least 100 fold, more preferably by at least 1000 fold. This loss in affinity underscores that residue's importance in the ability of the antibody to bind the epitope. See, e.g., Tamura et al., 2000, "Structural correlates of an anticarcinoma antibody: identification of specificity-determining residues (SDRs) and development of a minimally immunogenic antibody variant by retention of SDRs only," J. Immunol. 164(3):1432-1441.

The effect of single or multiple mutations on binding activity, particularly on binding affinity, may be evaluated contemporaneously to assess the importance of a particular series of amino acids on the binding interaction (e.g., the contribution of the light or heavy chain CDR2 to binding). Effects of an amino acid mutation may also be evaluated sequentially to assess the contribution of a single amino acid when assessed individually. Such evaluations can be performed, for example, by in vitro saturation scanning (see, e.g., U.S. Pat. No. 6,180,341; Hilton et al., 1996, "Saturation mutagenesis of the WSXWS motif of the erythropoietin receptor," J Biol. Chem. 271:4699-4708) and site-directed mutagenesis (see, e.g., Cunningham and Wells, 1989, "High-resolution epitope mapping of hGH-receptor interactions by alanine-scanning mutagenesis," Science 244:1081-1085; Bass et al., 1991, "A systematic mutational analysis of hormone-binding determinants in the human growth hormone receptor," Proc Natl Acad. Sci. USA 88:4498-4502). In the alanine-scanning mutagenesis technique, single alanine mutations are introduced at multiple residues in the molecule, and the resultant mutant molecules are tested for biological activity to identify amino acid residues that are critical to the activity of the molecule.

Sites of ligand-receptor or other biological interaction can also be identified by physical analysis of structure as determined by, for example, nuclear magnetic resonance, crystallography, electron diffraction, or photoaffinity labeling, in conjunction with mutation of putative contact site amino acids (see, e.g., de Vos et al, 1992, "Human growth hormone and extracellular domain of its receptor: crystal structure of the complex," Science 255:306-312; Smith et al., 1992, "Human interleukin 4. The solution structure of a four-helix bundle protein," J Mol. Biol. 224:899-904; Wlodaver et al., 1992, "Crystal structure of human recombinant interleukin-4 at 2.25 A resolution," FEBS Lett. 309:59-64. Additionally, the importance of particular individual amino acids, or series of amino acids, may be evaluated by comparison with the amino acid sequence of related polypeptides or analogous binding sites.

Furthermore, the skilled artisan would appreciate that increased avidity may compensate for lower binding affinity. The avidity of an immunotoxin for Ep-CAM is an measure of the strength of the Ep-CAM-binding portion's binding of Ep-CAM, which has multiple binding sites. The functional binding strength between Ep-CAM and the Ep-CAM-binding portion represents the sum strength of all the affinity bonds, and thus an individual component may bind with relatively low affinity, but a multimer of such components may demonstrate potent biological effect. In fact, the multiple interactions between Ep-CAM-binding sites and Ep-CAM epitopes may demonstrate much greater than additive biological effect, i.e., the advantage of multivalence can be many orders of magnitude with respect to the equilibrium constant.

In one non-limiting embodiment, the Ep-CAM-binding portion has a structure substantially similar to that of 4D5MOCB. The substantially similar structure can be characterized by reference to epitope maps that reflect the binding points of the immunotoxin's Ep-CAM-binding portion to an Ep-CAM molecule.

Likewise, a variety of toxins may be used to design an Ep-CAM-targeted immunotoxin according to the invention. In preferred embodiments, the toxin comprises a polypeptide having ribosome-inactivating activity including, without limitation, gelonin, bouganin, saporin, ricin A chain, bryodin, diphtheria toxin, restrictocin, and variants thereof. When the protein is a ribosome-inactivating protein, the immunotoxin must be internalized upon binding to the cancer cell in order for the toxin to be cytotoxic to the cells.

In a particular preferred embodiment, the toxin portion comprises at least a toxic portion of *Pseudomonas* exotoxin A ("ETA"), or a variant thereof. In a specific embodiment, the cytotoxic portion comprises an ETA variant that, when administered alone, is substantially unable to bind to cells. In a further, specific embodiment, the cytotoxic portion comprises ETA$^{252-608}$. The cytotoxic portion may comprises one or more *Pseudomonas* exotoxins known in the art (see, e.g., Kreitman, 1995, "Targeting *pseudomonas* exotoxin to hematologic malignancies," Seminars in Cancer Biology 6: 297-306; Pastan, 2003, "Immunotoxins containing *pseudomonas* exotoxin A: a short history," Cancer Immunol. Immunother. 52: 338-341), or variants thereof.

Several variants of *Pseudomonas* exotoxin, as well as methods of making and using constructs comprising *Pseudomonas* exotoxin variants, are known in the art (see, e.g., U.S. Patent Application No. US2003054012; U.S. Pat. No. 6,531,133; U.S. Pat. No. 6,426,075; U.S. Pat. No. 6,423,513; U.S. Pat. No. 6,074,644; U.S. Pat. No. 5,980,895; U.S. Pat. No. 5,912,322; U.S. Pat. No. 5,854,044; U.S. Pat. No. 5,821,238; U.S. Pat. No. 5,705,163; U.S. Pat. No. 5,705,156; U.S. Pat. No. 5,621,078; U.S. Pat. No. 5,602,095; U.S. Pat. No. 5,512,658; U.S. Pat. No. 5,458,878; U.S. Pat. No. 5,082,927; U.S. Pat. No. 4,933,288; U.S. Pat. No. 4,892,827; U.S. Pat. No. 4,677,070; U.S. Pat. No. 4,545,985; International Publication Nos. WO98/20135, WO93/25690; WO91/18100; WO91/18099; WO91/09949; and WO88/02401; Kondo et al, 19888, "Activity of immunotoxins constructed with modified *pseudomonas* exotoxin a lacking the cell recognition domain." J Biol. Chem. 263:9470-9475; Batra et al., 1989, "Antitumor activity in mice of an immunotoxin made with anti-transferring receptor and a recombinant form of *pseudomonas* exotoxin." Proc Natl. Acad. Sci. USA 86:8545-8549; Puri et al., 1991, "Expression of high-affinity interleukin 4 receptors on murine sarcoma cells and receptor-mediated cytotoxicity of tumor cells to chimeric protein between interleukin 4 and *Pseudomonas* exotoxin." Cancer Res 51:3011-3017; Siegall et al., 1992, "Cytotoxicity of chimeric (human murine) monoclonal antibody BR96 IgG, F(ab')2, and Fab' conjugated to *Pseudomonas* exotoxin." Bioconjug-Chem 3:302-307; Hall et al., 1994, "In vivo efficacy of intrathecal transferrin-*Pseudomonas* exotoxin A immunotoxin against LOX melanoma." Neurosurgery 34:649-655; Kuan and Pai, 1995, "Immunotoxins containing *pseudomonas* exotoxin that target Le y damage human endothelial cells in an antibody-specific mode: relevance to vascular leak syndrome." Clin Cancer Res 1:1589-1594; Kreitman, 1995, "Targeting *pseudomonas* exotoxin to hematologic malignancies." Sem Cancer Biol 6:297-306; Kawooya et al, "The expression, affinity purification and characterization of recombinant *pseudomonas* exotoxin 40 (PE40) secreted from *Escherichia coli*." J Biotechnol 42:9-22; Kaun and Pai, 1995, "Immunotoxins containing *pseudomonas* exotoxin that target LeY damage human endothelial cells in an antibody-specific mode: Relevance to vascular leak syndrome." Clin Cancer Res 1:1589-1594; Puri et al., 1996, "Preclinical development of a recombinant toxin containing circularly permuted interleukin 4 and truncated *Pseudomonas* exotoxin for therapy of malignant astrocytoma." Cancer Res 56:5631-5637; Pai et al., 1996, "Treatment of advanced solid tumors with immunotoxin LMB-1: An antibody linked to *Pseudomonas* exotoxin." Nature Med. 3:350-353; Pai et al., 1998, "Clinical Trials with *pseudomonas* exotoxin immunotoxins." Curr Top. Microbiol. Immunol. 234: 83-96; Klimka et al., 1999, "An anti-CD30 single chain Fv selected by phage display and fused to *pseudomonas* exotoxin A (Ki-4(scFv)-ETA') is a potent immunotoxin against a Hodgkin-derived cell line." British J Cancer 80:1214-1222; Rand et al., 2000, "Intratumoral administration of recombinant circularly permuted interleukin-4-*Pseudomonas* exotoxin in patients with high-grade glioma." Clin Cancer Res 6:2157-2165; Leland et al., 2000, "Human breast carcinoma cells express type II IL-4 receptors and are sensitive to antitumor activity of chimeric IL-4-*pseudomonas* exotoxin fusion protein in vitro and in vivo." Molecular Medicine Today 6:165-178; Tur et al., 2001, "An anti-GD2 single chain Fv selected by phage display and fused to *Pseudomonas* exotoxin A develops specific cytotoxic activity against neuroblastoma derived cell lines." Int J. Mol. Med 8:579-584; Onda et al., 2001, "Cytotoxicity of anti-osteosarcoma recombinant immunotoxins composed of TP-3 Fv fragments and a truncated *pseudomonas* exotoxin A." J Immunother 24:144-150; 18. "Synergistic interaction between an anti-p185her-2 *pseudomonas* exotoxin fusion protein [scfv(frp5)-eta] and ionizing radiation for inhibiting growth of ovarian cancer cells that overexpress HER-2." Schmidt et al., 2001, "Synergistic interaction between an anti-p185HER-2 *pseudomonas* exotoxin fusion protein [scFv (FRP5)-ETA| and ionizing radiation for inhibiting growth of ovarian cancer cells that overexpress HER-2." Gynecol Oncol 80:145-155; Pastan, 2003, "Immunotoxins containing *pseudomonas* exotoxin A; a short history," Cancer Immunol Immunother 52:338-341; Li et al, 1996, "Crystal structure of the catalytic domain of *Pseudomonas* exotoxin A complexed with a nicotinamide adenine dinucleotide analog: implications for the activation process and for ADP ribosylation." Proc Natl Acad Sci USA. 9:6902-6906; Kreitman and Pastan, 2003, "Immunobiological treatments of hairy-cell leukaemia." Best Pract Res Clin Haematol. 16:117-33.

In other nonlimiting embodiments, the toxin comprises an agent that acts to disrupt DNA. Thus, toxins may comprise, without limitation, enediynes (e.g., calicheamicin and esperamicin) and non-enediyne small molecule agents (e.g., bleomycin, methidiumpropyl-EDTA-Fe(II)). Other toxins useful in accordance with the invention include, without limitation, daunorubicin, doxorubicin, distamycin A, cisplatin, mitomycin C, ecteinascidins, duocarmycin/CC-1065, and bleomycin/peplomycin.

In other nonlimiting embodiments, the toxin comprises an agent that acts to disrupt tubulin. Such toxins may comprise, without limitation, rhizoxin/maytansine, paclitaxel, vincristine and vinblastine, colchicine, auristatin dolastatin 10 MMAE, and peloruside A.

In other nonlimiting embodiments, the toxin portion of an immunotoxin of the invention may comprise an alkylating agent including, without limitation, Asaley NSC 167780, AZQ NSC 182986, BCNU NSC 409962, Busulfan NSC 750, carboxyphthalatoplatinum NSC 271674, CBDCA NSC 241240, CCNU NSC 79037, CHIP NSC 256927, chlorambucil NSC 3088, chlorozotocin NSC 178248, cis-platinum NSC 119875, clomesone NSC 338947, cyanomorpholino-doxorubicin NSC 357704, cyclodisone NSC 348948, dianhydrogalactitol NSC 132313, fluorodopan NSC 73754, hepsulfam NSC 329680, hycanthone NSC 142982, melphalan NSC 8806, methyl CCNU NSC 95441, mitomycin C NSC 26980, mitozolamide NSC 353451, nitrogen mustard NSC 762, PCNU NSC 95466, piperazine NSC 344007, piperazinedione NSC 135758, pipobroman NSC 25154, porfiromycin NSC 56410, spirohydantoin mustard NSC 172112, teroxirone NSC 296934, tetraplatin NSC 363812, thio-tepa NSC 6396, triethylenemelamine NSC 9706, uracil nitrogen mustard NSC 34462, and Yoshi-864 NSC 102627.

In other nonlimiting embodiments, the toxin portion of an immunotoxin of the invention may comprise an antimitotic agent including, without limitation, allocolchicine NSC 406042, Halichondrin B NSC 609395, colchicine NSC 757, colchicine derivative NSC 33410, dolastatin 10 NSC 376128 (NG—auristatin derived), maytansine NSC 153858, rhizoxin NSC 332598, taxol NSC 125973, taxol derivative NSC 608832, thiocolchicine NSC 361792, trityl cysteine NSC 83265, vinblastine sulfate NSC 49842, and vincristine sulfate NSC 67574.

In other nonlimiting embodiments, the toxin portion of an immunotoxin of the invention may comprise an topoisomerase I inhibitor including, without limitation, camptothecin NSC 94600, camptothecin, Na salt NSC 100880, aminocamptothecin NSC 603071, camptothecin derivative NSC 95382, camptothecin derivative NSC 107124, camptothecin derivative NSC 643833, camptothecin derivative NSC 629971, camptothecin derivative NSC 295500, camptothecin derivative NSC 249910, camptothecin derivative NSC 606985, camptothecin derivative NSC 374028, camptothecin derivative NSC 176323, camptothecin derivative NSC 295501, camptothecin derivative NSC 606172, camptothecin derivative NSC 606173, camptothecin derivative NSC 610458, camptothecin derivative NSC 618939, camptothecin derivative NSC 610457, camptothecin derivative NSC 610459, camptothecin derivative NSC 606499, camptothecin 20 derivative NSC 610456, camptothecin derivative NSC 364830, camptothecin derivative NSC 606497, and morpholinodoxorubicin NSC 354646.

In other nonlimiting embodiments, the toxin portion of an immunotoxin of the invention may comprise an topoisomerase II inhibitor including, without limitation, doxorubicin NSC 123127, amonafide NSC 308847, m-AMSA NSC 249992, anthrapyrazole derivative NSC 355644, pyrazoloacridine NSC 366140, bisantrene HCL NSC 337766, daunorubicin NSC 82151, deoxydoxorubicin NSC 267469, mitoxantrone NSC 301739, menogaril NSC 269148, N,N-dibenzyl daunomycin NSC 268242, oxanthrazole NSC 349174, rubidazone NSC 164011, VM-26 NSC 122819, and VP-16 NSC 141540.

In other nonlimiting embodiments, the toxin portion of an immunotoxin of the invention may comprise an RNA or DNA antimetabolite including, without limitation, L-alanosine NSC 153353, 5-azacytidine NSC 102816, 5-fluorouracil NSC 19893, acivicin NSC 163501, aminopterin derivative NSC 132483, aminopterin derivative NSC 184692, aminopterin derivative NSC 134033, an antifol NSC 633713, an antifol NSC 623017, Baker's soluble antifol NSC 139105, dichlorallyl lawsone NSC 126771, brequinar NSC 368390, ftorafur (pro-drag) NSC 148958, 5,6-dihydro-5-azacytidine NSC 264880, methotrexate NSC 740, methotrexate derivative NSC 174121, N-(phosphonoacetyl)-L-aspartate (PALA) NSC 224131, pyrazofurin NSC 143095, trimetrexate NSC 352122, 3-HP NSC 95678, 2'-deoxy-5-fluorouridine NSC 27640, 5-HP NSC 107392, alpha-TGDR NSC 71851, aphidicolin glycinate NSC 303812, ara-C NSC 63878, 5-aza-2'-deoxycytidine NSC 127716, beta-TGDR NSC 71261, cyclocytidine NSC 145668, guanazole NSC 1895, hydroxyurea NSC 32065, inosine glycodialdehyde NSC 118994, macbecin II NSC 330500, pyrazoloimidazole NSC 51143, thioguanine NSC 752, and thiopurine NSC 755.

Furthermore, a cytotoxin may be altered to decrease or inhibit binding outside of the context of the immunotoxin, or to reduce specific types of toxicity. For example, the cytotoxin may be altered to adjust the isoelectric point to approximately 7.0 such that liver toxicity is reduced.

Clinical outcomes of cancer treatments using an immunotoxin of the invention are readily discernible by one of skill in the relevant art, such as a physician. For example, standard medical tests to measure clinical markers of cancer may be strong indicators of the treatment's efficacy. Such tests may include, without limitation, physical examination, performance scales, disease markers, 12-lead ECG, tumor measurements, tissue biopsy, cytoscopy, cytology, longest diameter of tumor calculations, radiography, digital imaging of the tumor, vital signs, weight, recordation of adverse events, assessment of infectious episodes, assessment of concomitant medications, pain assessment, blood or serum chemistry, urinalysis, CT scan, and pharmacokinetic analysis. Furthermore, synergistic effects of a combination therapy comprising the immunotoxin and another cancer therapeutic may be determined by comparative studies with patients undergoing monotherapy.

Particularly in the case of HNSCC, improvements in breathing, swallowing, speech, and certain quality of life measurements are readily ascertainable. Additionally, remission of HNSCC may be evaluated using criteria accepted by the skilled artisan. See, e.g., Therasse et al, 2000, "New guidelines to evaluate the response to treatment in solid tumors. European Organization for Research and Treatment of Cancer, National Cancer Institute of the United States, National Cancer Institute of Canada," J Natl Cancer Inst. February 2; 92(3):205-16.

The effective dose of immunotoxin to be administered during a cycle varies according to the mode of administration. Direct administration (e.g., intratumoral injection) requires much smaller total body doses of immunotoxin as compared to systemic, intravenous administration of the immunotoxin. It will be evident to the skilled artisan that local administration can result in lower body doses, and in those circumstances, and resulting low circulating plasma level of immunotoxin would be expected and desired.

Moreover, the effective dose of a specific immunotoxin construct may depend on additional factors, including the type of cancer, the size of the tumour in the case of HNSCC, the stage of the cancer, the immunotoxin's toxicity to the patient, the specificity of targeting to cancer cells, as well as the age, weight, and health of the patient.

In one embodiment, the effective dose by direct administration of immunotoxin may range from about 10 to 3000, 20 to 900, 30 to 800, 40 to 700, 50 to 600, 60 to 500, 70 to 400, 80 to 300, 90 to 200, or 100 to 150 micrograms/tumor/day. In other embodiments, the dose may range from approximately 10 to 20, 21 to 40, 41 to 80, 81 to 100, 101 to 130, 131 to 150, 151 to 200, 201 to 280, 281 to 350, 351 to 500, 501 to 1000, 1001 to 2000, or 2001 to 3000 micrograms/tumor/day. In specific embodiments, the dose may be at least approximately 20, 40, 80, 130, 200, 280, 400, 500, 750, 1000, 2000, or 3000 micrograms/tumor/day.

In another embodiment, the effective dose of immunotoxin may range from about 100 to 5000, 200 to 4000, 300 to 3000, 400 to 2000, 500 to 1000, 600 to 900, or 700 to 1500 micrograms/tumor/month. In other embodiments, the dose may range from approximately 100 to 199, 200 to 399, 400 to 649, 650 to 999, 1000 to 1799, 1800 to 2499, 2500 to 3499, 3500 to 4999, 5000 to 7499, 7500 to 10000, or 10001 to 20000 micrograms/tumor/month. In specific embodiments, the dose may be at least approximately 100, 200, 400, 650, 1000, 1400, 2000, 2500, 3000, 3500, 4000, 4500, 5000, 7500, 0000, or 20000 micrograms/tumor/month.

In another embodiment, the effective dose of immunotoxin results in an intratumoral concentration of at least approximately 5, 10, 20, 30, 40, 50, 60, 75, 100, 125, 150, 100, 200, 300, 400, or 500 micrograms/cm$^3$ of the immunotoxin. In other embodiments, the resulting intratumoral concentration of immunotoxin is approximately 5 to 500, 10 to 400, 15 to 300, 20 to 200, 25 to 100, 30 to 90, 35 to 80, 40 to 70, 45 to 60, or 50 to 55 micrograms/cm$^3$. In other embodiments, the resulting intratumoral concentration of immunotoxin is approximately 10 to 15, 16 to 20, 21 to 25, 26 to 30, 31 to 35, 36 to 40, 41 to 45, 46 to 50, 51 to 55, 56 to 60, 61 to 65, 66 to 70, 71 to 75, 76 to 80, 81 to 85, 86 to 90, 91 to 95, 96 to 100, or 100 to 200 micrograms/cm$^3$.

In another embodiment, the effective dose of immunotoxin results in a plasma concentration of less than approximately 0.1, 1, 2.5, 5, 7.5, 10, 15, 20, 30, 40, or 50 micrograms/liter. In other embodiments, the resulting circulating concentration of immunotoxin is approximately 0.1 to 50, 1 to 40, 2.5 to 30, 5 to 20, or 7.5 to 10 micrograms/liter. In other embodiments, the resulting circulating concentration of immunotoxin is approximately 0.1 to 1, 1.1 to 2.4, 2.5 to 5, 5.1 to 7.4, 7.5 to 10, 11 to 15, 16 to 20, 21 to 30, 31 to 40, or 41 to 50 micrograms/liter.

In a particular non-limiting embodiment, the effective dose of the immunotoxin is between about 100 and 3000 micrograms/tumor/month, for example approximately 100, 200, 300, 400, 750, or 1000 micrograms/tumor/month, wherein the patient is administered a single dose per day. The single dose is administered approximately every month for approximately 1, 2, 3, 4, 5, or 6 consecutive months. After this cycle, a subsequent cycle may begin approximately 1, 2, 4, 6, or 12 months later. The treatment regime may include 1, 2, 3, 4, 5, or 6 cycles, each cycle being spaced apart by approximately 1, 2, 4, 6, or 12 months.

In a particular non-limiting embodiment, the effective dose of the immunotoxin is between about 20 and 1240 micrograms/tumor/day, for example approximately 20, 40, 80, 130, 200, or 280 micrograms/tumor/day or approximately 100, 200, 330, 500, 700, 930, 1240 micrograms/tumor/day, wherein the patient is administered a single dose per day. The single dose is administered approximately every day (one or more days may optionally be skipped) for approximately 1, 2, 3, 4, 5, 6 or 7 consecutive days. After this cycle, a subsequent cycle may begin approximately 1, 2, 3, 4, 5, or 6 weeks later. The treatment regime may include 1, 2, 3, 4, 5, or 6 cycles, each cycle being spaced apart by approximately 1, 2, 3, 4, 5, or 6 weeks.

The injection volume preferably is at least an effective amount, which is appropriate to the type and/or location of the tumor. The maximum injection volume in a single dose may be between about 25% and 75% of tumor volume, for example approximately one-quarter, one-third, or three-quarters of the estimated target tumor volume. In a specific, non-limiting embodiment, the maximum injection volume in a single dose is approximately 30% of the tumor volume.

In another embodiment, the immunotoxin is administered intratumourally at a total dose per cycle equivalent to, or below the maximum tolerated dose established in a safety trial but the dosage is standardized in relation to the tumour volume. For example, subjects will receive between 1 microgram per cm$^3$ and 500 microgram per cm$^3$ tumour or a dose sufficient to reach about between 14 picomole and 7 nanomole per cm$^3$ tumour tissue. The dose will be administered in a volume not exceeding about 20-50% of the tumour volume. The immunotoxin will be diluted in a suitable salt solution. For example, for a tumour of estimated volume of 3 cm$^3$, a target dose of 14 picomoles (1 microgram per cm$^3$), and a maximum injection relative volume of about ⅓ of the tumour, 3 microgram of immunotoxin will be diluted into about 1 ml of diluent.

In another particular embodiment, the effective dose of the immunotoxin is between about 20 and 300 micrograms/tumor/day, for example approximately 20, 40, 80, 130, 200, or 280 micrograms/tumor/day, wherein the patient is administered a single dose per day. The maximum injection volume in a single dose may be between about 25% and 75% of tumor volume, for example approximately one-quarter, one-third, or three-quarters of the estimated target tumor volume. The single dose is administered every other day for approximately 5, 7, 9, 11, 13, 15, 17, 19, 21, 23, 25, 27, 29, or 31 consecutive days. After this cycle, a subsequent cycle may begin approximately 1, 2, 3, 4, 5, 6, 7, 8, 9, 10, 11, or 12 weeks later. The treatment regime may include 1, 2, 3, 4, 5, or 6 cycles, each cycle being spaced apart by approximately 1, 2, 3, 4, 5, 6, 7, 8, 9, 10, 11, or 12 weeks.

In one specific non-limiting embodiment, VB4-845 is administered at a dose of approximately 280 micrograms/tumor/day, wherein the patient is administered a single dose per day. The maximum injection volume in a single dose is approximately one-third of the estimated target tumor volume. The single dose is administered every day for approximately five consecutive days. After this cycle, a subsequent cycle may begin approximately one month later, preferably one month from the first day of the first cycle. The treatment regime may include three cycles, each cycle being spaced apart by approximately one treatment-free week.

In another specific non-limiting embodiment, VB4-845 is administered at a dose of approximately 280 micrograms/tumor/day, wherein the patient is administered a single dose per day. The maximum injection volume in a single dose is approximately one-third of the estimated target tumor volume. The single dose is administered every other day for approximately one week. After this cycle, a subsequent cycle may begin approximately one week later. The treatment regime may include three cycles, each cycle being spaced apart by approximately one week.

In yet another specific embodiment, VB4-845 is administered at a dose of approximately 280 micrograms/tumor/day, wherein the patient is administered a single dose per day. The maximum injection volume in a single dose is approximately one-third of the estimated target tumor volume. The single dose is administered every other day for approximately three weeks. After this cycle, a subsequent cycle may begin approximately one week later. The treatment regime may include three cycles, each cycle being spaced apart by approximately one week.

For administration to a cavity such as the urinary bladder, the effective dose of the immunotoxin is between about 100 and 2000 micrograms in 50 ml/week (equivalent to a concentration of between about 29 nanomolar to 580 nanomolar), for example approximately 100, 200, 335, 500, 700, 930, 1240 micrograms in 50 ml/week, wherein the patient is administered a single dose per week and the tumour tissue is exposed to the immunotoxin for at least about 30 minutes. For example, the solution is retained into the cavity for about 30 minutes to about 3 hours. In a specific non-limiting embodiment, the tumour tissue is exposed to the immunotoxin for about 1 hours or more preferably for about 2 hours. After this cycle, a subsequent cycle may begin approximately 1, 2, 4, 6, or 12 weeks after the previous dose. The treatment regime may include 1, 2, 3, 4, 5, or 6 cycles, each cycle being spaced apart by approximately 1, 2, 4, 6, or 12 months.

For smaller or larger cavities such as cysts or bladder substantially smaller or larger than average, the volume can be adjusted to ensure adequate exposure of the tissue without overextending the cavity. Where the volume needs to be adjusted, the effective dose of the immunotoxin should be between about 20 and 600 nanomolar in concentration for a toxin with one binding site per molecule.

Dosage for the immunotoxin can also be expressed as molarity of the binding site for the protein on the cancer cells. For example, the immunotoxin VB4-845 has a molecular weight of about 69.7 kDa and one binding site for Ep-Cam. It is known that other immunotoxin formats such as divalent formats, Fab' or (Fab')$_2$ fragment could have a different molecular weight by virtue of the number of amino acids in the polypeptide chain or chains. It is also known that for a similar format one could alter the molecular weight by attaching additional groups to the polypeptide such sugar moiety or polyethylene glycol. The use of a different toxin or a different variant of the toxin could also result in an immunotoxin with a different molecular weight than VB4-845 used in the examples. Furthermore, changes to the polypeptide chain that result in a longer or a shorter fragment could also be made and yet without losing the binding of the immunotoxin to the chosen protein on the cancer cell. All those variations are contemplated in this application. As a result it may be helpful to express the dosage of the immunotoxin in terms of the number of moles of the binding sites for the protein on the cancer cells. In the examples and the various embodiments, the dosages are expressed in micrograms and are based on the molecular weight of VB4-845. The following formula provides a simple way to transform micrograms into mole equivalent of binding sites; $(1\times10^{-6}$ g/number of g per mole immunotoxin)$\times$number of binding site per immunotoxin molecule=Conversion Factor to go from microgram $(1\times10^{-6}$ g) of a given IT to moles of binding sites. For VB4-845, an immunotoxin with only one binding site per molecule, the conversion would be done as follows: Number of micrograms$\times14.3\times10^{-12}$ moles/microgram=number of moles.

For example, where 3000 micrograms are to be injected in a tumour on a given day, 3000 micrograms$\times14.3\times10^{-12}$ moles/microgram=42.9$\times10^{-9}$ moles binding sites (or 42.9 nanomoles or 42,900 picomoles). Where the dose is expressed in terms of a concentration in a diluent or by tumour tissue volume, one can transform the weight of the immunotoxin into moles and then divide this number of moles by the volume of diluent where the result can be expressed in terms of molarity or by the volume tumour tissue where the result can be expressed as moles per cm$^3$ (or other units of volume) of tissue.

For example, where 1240 microgram are to be administered into the bladder in a volume of 50 ml: 1240 microgram$\times14.3\times10^{-12}$ moles/microgram=about $18\times10^{-2}$ moles binding sites and $18\times10^{-12}$ moles/50 ml (or 0.05 liter)=about $355\times10^{-9}$M (or 355 nanomolar).

The effective dose of another cancer therapeutic to be administered together with an immunotoxin during a cycle also varies according to the mode of administration. The one or more cancer therapeutics may be delivered intratumorally, or by other modes of administration. Typically, chemotherapeutic agents are administered systemically. Standard dosage and treatment regimens are known in the art (see, e.g., the latest editions of the Merck Index and the Physician's Desk Reference).

For example, in one embodiment, the additional cancer therapeutic comprises dacarbazine at a dose ranging from approximately 200 to 4000 mg/m$^2$/cycle. In a preferred embodiment, the dose ranges from 700 to 1000 mg/m$^2$/cycle.

In another embodiment, the additional cancer therapeutic comprises fludarabine at a dose ranging from approximately 25 to 50 mg/m$^2$ cycle.

In another embodiment, the additional cancer therapeutic comprises cytosine arabinoside (Ara-C) at a dose ranging from approximately 200 to 2000 mg/m$^2$/cycle.

In another embodiment, the additional cancer therapeutic comprises docetaxel at a dose ranging from approximately 1.5 to 7.5 mg/kg/cycle.

In another embodiment, the additional cancer therapeutic comprises paclitaxel at a dose ranging from approximately 5 to 15 mg/kg/cycle.

In yet another embodiment the additional cancer therapeutic comprises cisplatin at a dose ranging from approximately 5 to 20 mg/kg/cycle.

In yet another embodiment, the additional cancer therapeutic comprises 5-fluorouracil at a dose ranging from approximately 5 to 20 mg/kg/cycle.

In yet another embodiment, the additional cancer therapeutic comprises doxorubicin at a dose ranging from approximately 2 to 8 mg/kg/cycle.

In yet another embodiment, the additional cancer therapeutic comprises epipodophyllotoxin at a dose ranging from approximately 40 to 160 mg/kg/cycle.

In yet another embodiment, the additional cancer therapeutic comprises cyclophosphamide at a dose ranging from approximately 50 to 200 mg/kg/cycle.

In yet another embodiment, the additional cancer therapeutic comprises irinotecan at a dose ranging from approximately 50 to 75, 75 to 100, 100 to 125, or 125 to 150 mg/m2/cycle.

In yet another embodiment, the cancer therapeutic comprises vinblastine at a dose ranging from approximately 3.7 to 5.4, 5.5 to 7.4, 7.5 to 11, or 11 to 18.5 mg/m/cycle.

In yet another embodiment, the additional cancer therapeutic comprises vincristine at a dose ranging from approximately 0.7 to 1.4, or 1.5 to 2 mg/m$^2$/cycle.

In yet another embodiment, the additional cancer therapeutic comprises methotrexate at a dose ranging from approximately 3.3 to 5, 5 to 10, 10 to 100, or 100 to 1000 mg/m2/cycle.

Combination therapy with an immunotoxin may sensitize the cancer or tumor to administration of an additional cancer therapeutic. Accordingly, the present invention contemplates combination therapies for preventing, treating, and/or preventing recurrence of cancer comprising administering an effective amount of an immunotoxin prior to, subsequently, or concurrently with a reduced dose of a cancer therapeutic. For example, initial treatment with an immunotoxin may increase the sensitivity of a cancer or tumor to subsequent challenge with a dose of cancer therapeutic. This dose is near, or below, the low range of standard dosages when the cancer therapeutic is administered alone, or in the absence of an immunotoxin. When concurrently administered, the immunotoxin may be administered separately from the cancer therapeutic, and optionally, via a different mode of administration.

Accordingly, in one embodiment, the additional cancer therapeutic comprises eisplatin, e.g., PLATINOL or PLATINOL-AQ (Bristol Myers), at a dose ranging from approximately 5 to 10, 11 to 20, 21 to 40, or 41 to 75 mg/m$^2$/cycle.

In another embodiment, the additional cancer therapeutic comprises carboplatin, e.g., PARAPLATIN (Bristol Myers), at a dose ranging from approximately 2 to 3, 4 to 8, 9 to 16, 17 to 35, or 36 to 75 mg/m$^2$/cycle.

In another embodiment, the additional cancer therapeutic comprises cyclophosphamide, e.g. CYTOXAN (Bristol Myers Squibb), at a dose ranging from approximately 0.25 to 0.5, 0.6 to 0.9, 1 to 2, 3 to 5, 6 to 10, 11 to 20, or 21 to 40 mg/kg/cycle.

In another embodiment, the additional cancer therapeutic comprises cytarabine, e.g., CYTOSAR-U (Pharmacia & Upjohn), at a dose ranging from approximately 0.5 to 1, 2 to 4, 5 to 10, 11 to 25, 26 to 50, or 51 to 100 mg/m$^2$/cycle. In another embodiment, the additional cancer therapeutic comprises cytarabine liposome, e.g., DEPOCYT (Chiron Corp.), at a dose ranging from approximately 5 to 50 mg/m$^2$/cycle.

In another embodiment, the additional cancer therapeutic comprises dacarbazine, e.g., DTIC or DTICDOME (Bayer Corp.), at a dose ranging from approximately 15 to 250 mg/m$^2$/cycle or ranging from approximately 0.2 to 2 mg/kg/cycle.

In another embodiment, the additional cancer therapeutic comprises topotecan, e.g., HYCAMTIN (SmithKline Beecham), at a dose ranging from approximately 0.1 to 0.2, 0.3 to 0.4, 0.5 to 0.8, or 0.9 to 1.5 mg/m$^2$/Cycle.

In another embodiment, the additional cancer therapeutic comprises irinotecan, e.g., 25 CAMPTOSAR (Pharmacia & Upjohn), at a dose ranging from approximately 5 to 9, 10 to 25, or 26 to 50 mg/m2/cycle.

In another embodiment, the additional cancer therapeutic comprises fludarabine, e.g., FLUDARA (Berlex Laboratories), at a dose ranging from approximately 2.5 to 5, 6 to 10, 11 to 15, or 16 to 25 mg/m$^2$/cycle.

In another embodiment, the additional cancer therapeutic comprises cytosine arabinoside (Ara-C) at a dose ranging from approximately 200 to 2000 mg/m$^2$/cycle, 300 to 1000 mg/m$^2$/cycle, 400 to 800 mg/m$^2$/cycle, or 500 to 700 mg/m$^2$/cycle.

In another embodiment, the additional cancer therapeutic comprises docetaxel, e.g., TAXOTERE (Rhone Poulenc Rorer) at a dose ranging from approximately 6 to 10, 11 to 30, or 31 to 60 mg/m$^2$/cycle.

In another embodiment, the additional cancer therapeutic comprises paclitaxel, e.g., TAXOL (Bristol Myers Squibb), at a dose ranging from approximately 10 to 20, 21 to 40, 41 to 70, or 71 to 135 mg/kg/cycle.

In another embodiment, the additional cancer therapeutic comprises 5-fluorouracil at a dose ranging from approximately 0.5 to 5 mg/kg/cycle, 1 to 4 mg/kg/cycle, or 2-3 mg/kg/cycle.

In another embodiment, the additional cancer therapeutic comprises doxorubicin, e.g., ADRIAMYCIN (Pharmacia & Upjohn), DOXIL (Alza), RUBEX (Bristol Myers Squibb), at a dose ranging from approximately 2 to 4, 5 to 8, 9 to 15, 16 to 30, or 31 to 60 mg/kg/cycle.

In another embodiment, the additional cancer therapeutic comprises etoposide, e.g., VEPESID (Pharmacia & Upjohn), at a dose ranging from approximately 3.5 to 7, 8 to 15, 16 to 25, or 26 to 50 mg/m$^2$/cycle.

In another embodiment, the additional cancer therapeutic comprises vinblastine, e.g., VELBAN (Eli Lilly), at a dose ranging from approximately 0.3 to 0.5, 0.6 to 0.9, 1 to 2, or 3 to 3.6 mg/m$^2$/cycle.

In another embodiment, the additional cancer therapeutic comprises vincristine, e.g., ONCOVIN (Eli Lilly), at a dose ranging from approximately 0.1, 0.2, 0.3, 0.4, 0.5, 0.6 or 0.7 mg/m$^2$/cycle.

In another embodiment, the additional cancer therapeutic comprises methotrexate at a dose ranging from approximately 0.2 to 0.9, 1 to 5, 6 to 10, or 11 to 20 mg/m$^2$/cycle.

In another embodiment, an immunotoxin is administered in combination with at least one other immunotherapeutic which includes, without limitation, rituxan, rituximab, campath-1, gemtuzumab, and trastuzutmab.

In another embodiment, an immunotoxin is administered in combination with one or more anti-angiogenic agents which include, without limitation, angiostatin, thalidomide, kringle 5, endostatin, Serpin (Serine Protease Inhibitor), antithrombin, 29 kDa N-terminal and a 40 kDa C-terminal proteolytic fragments of fibronectin, 16 kDa proteolytic fragment of prolactin, 7.8 kDa proteolytic fragment of platelet factor-4, a 13 amino acid peptide corresponding to a fragment of platelet factor-4 (Maione et al., 1990, Cancer Res, 51:2077-2083), a 14-amino acid peptide corresponding to a fragment of collagen I (Tolma et al., 1993, J. Cell Biol. 122: 497-511), a 19 amino acid peptide corresponding to a fragment of Thrombospondin I (Tolsma et al., 1993, J, Cell Biol. 122:497-511), a 20-amino acid peptide corresponding to a fragment of SPARC (Sage et al., 1995, J. Cell Biochem. 57:1329-1334), and a variant thereof, including a pharmaceutically acceptable salt thereof.

In another embodiment, an immunotoxin is administered in combination with a regimen of radiation therapy. The therapy may also comprise surgery and/or chemotherapy. For example, the immunotoxin may be administered in combination with radiation therapy and cisplatin (Platinol), fluorouracil (5-FU, Adrucil), carboplatin (Paraplatin), and/or paclitaxel (Taxol). Treatment with the immunotoxin may allow use of lower doses of radiation and/or less frequent radiation treatments, which may for example, reduce the incidence of severe sore throat that impedes swallowing function potentially resulting in undesired weight loss or dehydration.

In another embodiment, an immunotoxin is administered in combination with one or more cytokines which include, without limitation, a lymphokine, tumor necrosis factors, tumor necrosis factor-like cytokine, lymphotoxin, interferon, macrophage inflammatory protein, granulocyte monocyte colony stimulating factor, interleukin (including, without limitation, interleukin-1, interleukin-2, interleukin-6, interleukin-12, interleukin-15, interleukin-18), and a variant thereof, including a pharmaceutically acceptable salt thereof.

In yet another embodiment, an immunotoxin is administered in combination with a cancer vaccine including, without limitation, autologous cells or tissues, non-autologous cells or tissues, carcinoembryonic antigen, alpha-fetoprotein, human chorionic gonadotropin, BCG live vaccine, melanocyte lineage proteins, and mutated, tumor-specific antigens.

In yet another embodiment, an immunotoxin is administered in association with hormonal therapy. Hormonal therapeutics include, without limitation, a hormonal agonist, hormonal antagonist (e.g., flutamide, tamoxifen, leuprolide acetate (LUPRON)), and steroid (e.g., dexamethasone, retinoid, betamethasone, cortisol, cortisone, prednisone, dehydrotestosterone, glucocorticoid, mineralocorticoid, estrogen, testosterone, progestin).

In yet another embodiment, an immunotoxin is administered in association with a gene therapy program to treat or prevent cancer.

In yet another embodiment, an Ep-CAM-targeted immunotoxin is administered in combination with one or more agents that increase expression of Ep-CAM in the tumor cells of interest. Ep-CAM expression preferably is increased so that a greater number of Ep-CAM molecules are expressed on the tumor cell surface. For example, the agent may inhibit the normal cycles of Ep-CAM antigen endocytosis. Such combination treatment may improve the clinical efficacy of the Ep-CAM-targeted immunotoxin alone, or with other cancer therapeutics or radiation therapy. In specific, nonlimiting embodiments, the agent which increases Ep-CAM expression in the tumor cells is vinorelbine tartrate (Navelbine) and/or paclitax (Taxol). See, e.g., Thurmond et al., 2003, "Adenocarcinoma cells exposed in vitro to Navelbine or Taxol increase Ep-CAM expression through a novel mechanism." Cancer Immunol Immunother. July; 52(7):429-37.

Combination therapy may thus increase the sensitivity of the cancer or tumor to the administered immunotoxin and/or additional cancer therapeutic. In this manner, shorter treatment cycles may be possible thereby reducing toxic events. Accordingly, the invention provides a method for treating or preventing cancer comprising administering to a patient in need thereof an effective amount of an immunotoxin and at least one other cancer therapeutic for a short treatment cycle. The cycle duration may range from approximately 1 to 30, 2 to 27, 3 to 15, 4 to 12, 5 to 9, or 6-8 days. The cycle duration may vary according to the specific cancer therapeutic in use. The invention also contemplates continuous or discontinuous administration, or daily doses divided into several partial administrations. An appropriate cycle duration for a specific cancer therapeutic will be appreciated by the skilled artisan, and the invention contemplates the continued assessment of optimal treatment schedules for each cancer therapeutic. Specific guidelines for the skilled artisan are known in the art. See, e.g., Therasse et al., 2000, "New guidelines to evaluate the response to treatment in solid tumors. European Organization for Research and Treatment of Cancer, National Cancer Institute of the United States, National Cancer Institute of Canada," J Natl Cancer Inst. February 2; 92(3):205-16.

Alternatively, longer treatment cycles may be desired. Accordingly, the cycle duration may range from approximately 10 to 56, 12 to 48, 14 to 28, 16 to 24, or 18 to 20 days. The cycle duration may vary according to the specific cancertherapeutic in use.

The present invention contemplates at least one cycle, preferably more than one cycle during which a single cancer therapeutic or series of therapeutics is administered. An appropriate total number of cycles, and the interval between cycles, will be appreciated by the skilled artisan. The number of cycles may be 1, 2, 3, 4, 5, 6, 7, 8, 9, 10, 11, 12, 13, 14, 15, 16, 17, 18, 19, 20, or 21 cycles. The interval between cycles may be 1, 2, 3, 4, 5, 6, 7, 8, 9, 10, 11, 12, 13, 14, 15, 16, 17, 18, 19, 20, or 21 days. The invention contemplates the continued assessment of optimal treatment schedules for each immunotoxin and additional cancer therapeutic.

In one nonlimiting embodiment of the invention, the immunotoxin is directly administered at high doses (e.g., a dose resulting in greater than approximately 100, 200, 300, 400, 500, or 1000 micrograms/cm$^3$) for shorter periods. Accordingly, in one nonlimiting, specific embodiment, the immunotoxin is administered intratumorally at a dose that results in an intratumoral concentration of immunotoxin of at least approximately 200, 300, 400, or 500 micrograms/cm$^3$ once a week for two weeks.

An immunotoxin according to the invention may be comprised in a pharmaceutical composition or medicament. Pharmaceutical compositions adapted for direct administration include, without limitation, lyophilized powders or aqueous or non-aqueous sterile injectable solutions or suspensions, which may further contain antioxidants, buffers, bacteriostats and solutes that render the compositions substantially isotonic with the blood of an intended recipient. Other components that may be present in such compositions include water, alcohols, polyols, glycerin and vegetable oils, for example. Extemporaneous injection solutions and suspensions may be prepared from sterile powders, granules and tablets. Immunotoxin may be supplied, for example but not by way of limitation, as a lyophilized powder which is reconstituted with sterile water or saline prior to administration to the patient.

Pharmaceutical compositions of the invention may comprise a pharmaceutically acceptable carrier. Suitable pharmaceutically acceptable carriers include essentially chemically inert and nontoxic compositions that do not interfere with the effectiveness of the biological activity of the pharmaceutical composition. Examples of suitable pharmaceutical carriers include, but are not limited to, water, saline solutions, glycerol solutions, ethanol, N-(1(2,3-dioleyloxy)propyl)N,N,N-trimethylammonium chloride (DOTMA), diolesylphosphotidyl-ethanolamine (DOPE), and liposomes. Such compositions should contain a therapeutically effective amount of the compound, together with a suitable amount of carrier so as to provide the form for direct administration to the patient.

In another embodiment, a pharmaceutical composition comprises an immunotoxin and one or more additional cancer therapeutics, optionally in a pharmaceutically acceptable carrier.

The composition may be in the form of a pharmaceutically acceptable salt which includes, without limitation, those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc. In various embodiments of the invention, the pharmaceutical composition is directly administered to the area of the tumor(s) by, for example, local infusion during surgery, topical application (e.g., in conjunction with a wound dressing after surgery), injection, means of a catheter, means of a suppository, or means of an implant. An implant can be of a porous, non-porous, or gelatinous material, including membranes, such as sialastic membranes, or fibers. Suppositories generally contain active ingredients in the range of 0.5% to 10% by weight.

In other embodiments, a controlled release system can be placed in proximity of the target tumor. For example, a micropump may deliver controlled doses directly into the area of the tumor, thereby finely regulating the timing and concentration of the pharmaceutical composition (see, e.g., Goodson, 1984, in Medical Applications of Controlled Release, vol. 2, pp. 115-138).

The present invention also provides a kit comprising an effective amount of an immunotoxin, optionally, in combination with one or more other cancer therapeutics, together with instructions for the use thereof to treat HNSCC or bladder cancer.

In accordance with one aspect of the present invention, the immunotoxin and/or other cancer therapeutic is delivered to the patient by direct administration. Accordingly, the immunotoxin and/or other cancer therapeutic may be administered, without limitation, by one or more direct injections into the tumor, by continuous or discontinuous perfusion into the tumor, by introduction of a reservoir of the immunotoxin, by introduction of a slow-release apparatus into the tumor, by introduction of a slow-release formulation into the tumor, and/or by direct application onto the tumor. By the mode of administration "into the tumor," introduction of the immunotoxin and/or other cancer therapeutic to the area of the tumor, or into a blood vessel or lymphatic vessel that substantially directly flows into the area of the tumor, is also contemplated. In each case, the pharmaceutical composition is administered in at least an amount sufficient to achieve the endpoint, and if necessary, comprises a pharmaceutically acceptable carrier.

It is contemplated that the immunotoxin may be administered intratumorally, whereas any other cancer therapeutic may be delivered to the patient by other modes of administration (e.g., intravenously). Additionally, where multiple cancer therapeutics are intended to be delivered to a patient, the immunotoxin and one or more of the other cancer therapeutics may be delivered intratumorally, whereas other cancer therapeutics may be delivered by other modes of administration (e.g., intravenously and orally).

In a particular, non-limiting embodiment, the immunotoxin and/or other cancer therapeutic may be administered by intratumoral injection, for example, following the template shown in FIG. 1 (see Khuri et al, 2000, "A controlled trial of intratumoral ONYX-015, a selectively-replicating adenovirus, in combination with cisplatin and 5-fluorouracil in patients with recurrent head and neck cancer," Nature Med. 6:879-885). The immunotoxin and/or other cancer therapeutic may be suspended comprising a buffered aqueous solution, e.g., phosphate-buffered saline ("PBS"). The volume of the suspension comprising the immunotoxin may be less than approximately 5, 15, 25, 35, 45, 55, 65, 75, 85, or 95% of the estimated volume of the tumor mass to be injected. In specific embodiments, the volume of the suspension comprising the immunotoxin is less than approximately 30, 40, or 50% of the estimated volume of the target tumor mass, With each administration of the immunotoxin and/or other cancer therapeutic, at least one puncture of the skin or oral mucosa is made at a site approximately 10, 20, 30, 40, 50, 60, 70, 80, 90, or 100% of the distance from the estimated tumor center to the tumor periphery. Administration of the immunotoxin by direct injection may result in one or more needle tracks emanating radially from the center of the tumor mass. In a particular, non-limiting embodiment, needle tracks may be oriented substantially as depicted in FIG. 1.

For bladder carcinoma, the immunotoxin can be introduced by catheter as described in Example 15.

In a nonlimiting embodiment of the invention, medical imaging techniques are used to guide the administration of the immunotoxin directly to the tumour. This is particularly useful in some tumour of the head and neck and in other types of tumour that are difficult to access. In these cases, image guidance of the administration tool (needle, catheter, slow release apparatus, etc) are used to prevent damage to, or administration into critical anatomical structures such as blood vessels, nerve tract, etc. and to ensure that the immunotoxin is adequately distributed throughout a three dimensional tumour. Medical imaging-guidance techniques are well known to the medical art and comprise ultrasound, CT scans, X-ray and PET scan guidance.

The present invention will be better understood by the following exemplary teachings. The examples set forth herein are not intended to limit the invention.

EXAMPLES

Example 1

VB4-845 Immunotoxin

VB4-845 is an immunotoxin comprised of a single-chain Fv recombinant human antibody fragment that is fused to a truncated form of *Pseudomonas* exotoxin A (ETA 252-608). The antibody fragment is derived from the humanized MOC31 single-chain antibody fragment, 4D5MOCB, which specifically binds to Ep-CAM[16-18].

Exotoxin A is one of the toxic proteins released by pathogenic strains of *Pseudomonas aeruginosa*[19], It is secreted as a proenzyme with a molecular weight of 66,000 daltons[20]. Exotoxin A is translocated into susceptible mammalian cells, where covalent alteration of the molecule renders it enzymatically active. *Pseudomonas* exotoxin A irreversibly blocks protein synthesis in cells by adenositie diphosphate-ribosylating a post-translationally modified histidine residue of elongation factor-2, called diphthamide, and induces apoptosis[4]. The truncated version of ETA used in this construct, while still containing the domains for inducing cell death, lacks the cell-binding domain, thereby preventing the ETA portion from entering cells absent targeting by the antibody portion of the immunotoxin.

Figure 2A:
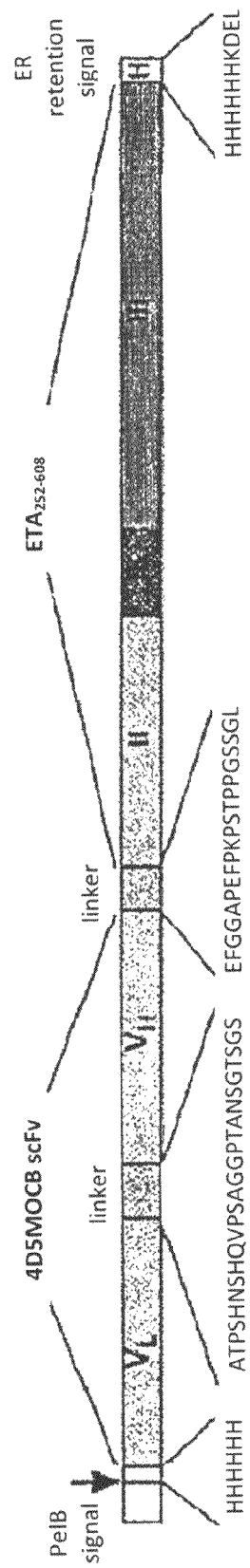
Figure 2B:
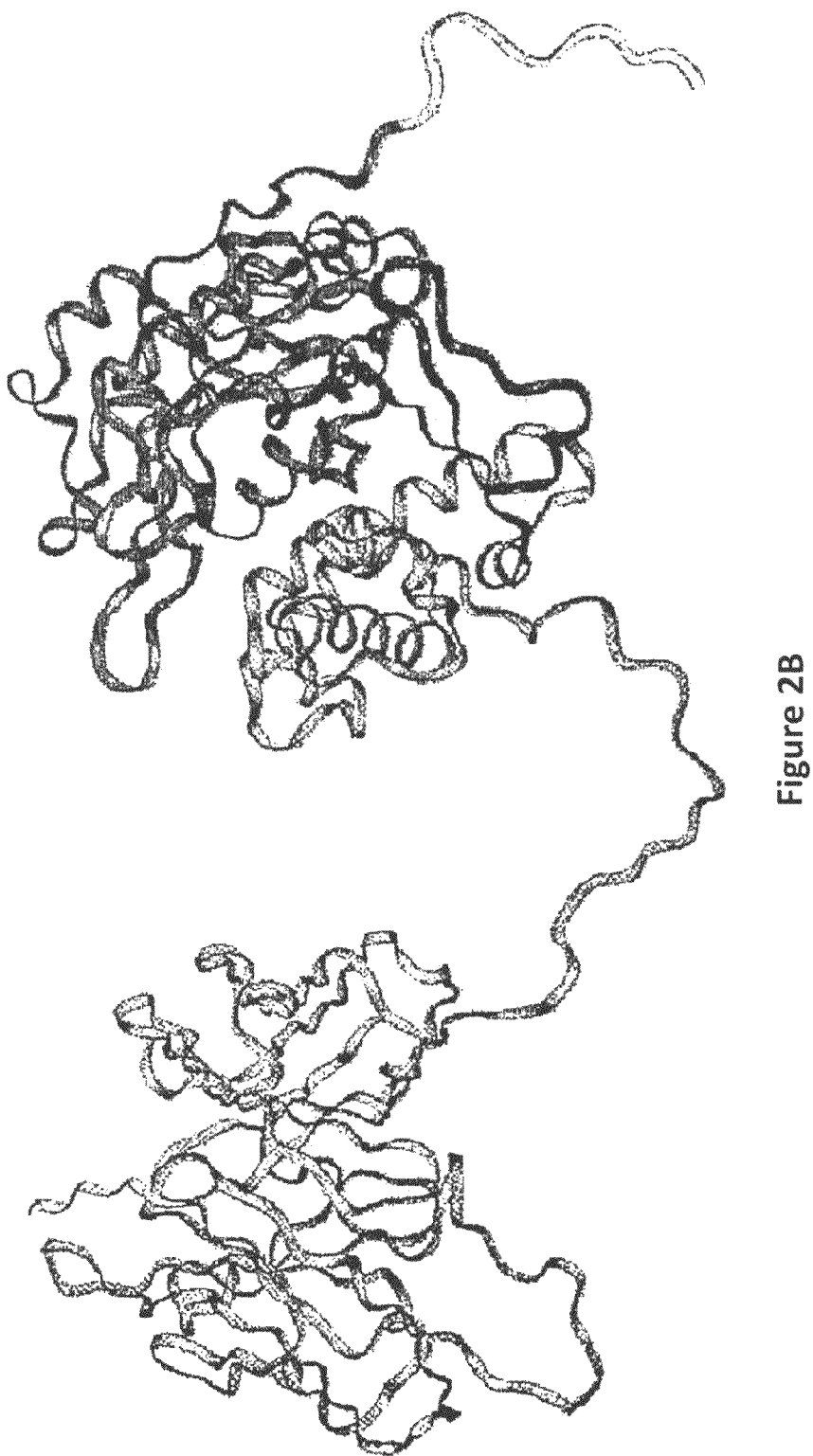

The gene sequence encoding a truncated form of the ETA ($ETA_{252-608}$), and the Ep-CAM-binding 4D5MOCB scFv sequence were used to construct VB4-845. The molecule contains both N- and C-terminal $His_5$ tails for purification, as depicted in FIG. 2. The DNA and ammo acid sequence of VB4-845 is depicted in FIGS. 3A-D and SEQ ID NOS:1 and 2. The Ep-CAM binding portion is shown in SEQ ID NO:3. The CDR sequences are shown in SEQ ID NOS:4-9.

The resulting protein retains the specificity of the parent 4D5MOCB for Ep-CAM. The expression vector for the protein, pING3302 (Plasmid pING3302 from Xoma Ireland Ltd was used for the construction of the expression vector.) is carried and expressed by the E104 *E. coli* host strain. The protein is 648 amino acids in length and has a predicted molecular weight of 69.7 kilodalton (kDa). In SDS-PAGE (sodium dodesyl sulfate-polyacrylamide gel electrophoresis) analysis, VB4-845 is observed as a single protein band of approximately 70 kDa. The protein has an isoelectric point (pI) of approximately 5.9, and is water-soluble forming a clear solution. Additional details regarding the preparation of VB4-845 are provided in Example 9, infra.

VB4-845 has been shown to specifically inhibit protein synthesis and reduce the viability of Ep-CAM-positive carcinoma cells in vitro. As demonstrated in Example 5, below, upon systemic administration to mice, VB4-845 inhibited growth and induced regression of tumor xenografts derived from lung, colon, or squamous cell carcinomas. VB4-845 showed similar organ distribution as the parental single chain fragment (scFv) and preferentially localized to Ep-CAM-positive tumor xenografts with a tumor:blood ratio of 5.4.

As demonstrated in Example 6, a peritumoral model in mice showed significant inhibition of tumor growth in VB4-845-treated animals. In fact, in this model, two mice with smaller tumor volumes (90 mm³) at the start of treatment showed complete tumor regression and remained tumor free during the experiment (see below). In all the efficacy studies, the mice tolerated the treatments well, with no drug related mortality and no significant clinical observations suggestive of toxicity. These data support the direct administration of VB4-845 for targeted therapy of solid tumors.

The dose range per cycle of VB4-845 in humans may be 4 micrograms/kilogram, i.e., 113 fold lower than the doses given to mice in the efficacy studies, both in the intravenous and peritumoral models (see footnote 1 of Table 7): The monthly exposure in humans may be administered as a microdose over the course of 5 days, with a cumulative effect of 1 dose per week throughout the total tumor area.

Example 2

Dosage Forms and Compositions

VB4-845 has been studied as a nascent drug and has been found to be effective in binding to tumor cell lines and in some model systems, preventing tumor growth. VB4-845 is formulated at 1 mg/ml in 20 mM sodium phosphate, 500 mM NaCl, pH 7.2, and can be administered by an intratumoral route with a 22-gauge needle. It is packaged in 1 ml borosilicate glass vials, closed with a gray butyl stopper and an aluminum overseal. Two fill sizes are currently available; 0.1 and 0.2 mL (0.1 mg and 0.2 mg VB4-845, respectively). Drug is stored at −70° C. The final product is not preserved and is for single use only.

The sample product is labeled, stored, and shipped according to written and approved standard operating procedures. The product may be shipped under frozen conditions (e.g., on dry ice), and may be maintained, for example, at the study site in a limited access, controlled −70° C. freezer that is monitored regularly for temperature.

The product may be maintained at this condition until time of use.

Example 3

Stability of VB4-845

The shelf-life of the product when stored at −70° C. is at least six months. At physiological conditions (e.g., incubation of the drug product for four hours at 37° C. in PBS), the majority. of the immunotoxin molecules (at least 91%) are still eluted as monomers of the appropriate molecular weight (approximately 70 kDa). The amount of VB4-845 slowly decreases with time with no less than approximately 47% of the initial protein being present in monomeric form after twenty hours at 37° C. Similar results were obtained upon incubation of $^{99m}$Tc-labeled VB4-845 in human serum, further corroborating the suitability of the immunotoxin for in vivo application.

Short term stability studies have been conducted to evaluate the inherent stability of the investigational product under routine handling at the clinical site. VB4-845 was evaluated in its standard formulation at room temperature and at 2-8° C. In addition, VB4-845 was prepared in injection buffer of phosphate-buffered saline with and without 800 mM urea and tested up to six hours at room temperature. The short term stability studies also evaluated the impact of repeated freeze-thaw cycles on VB4-845.

VB4-845 was found to retain its biological activity over the course of all the short-term stability studies. VB4-845 may be withdrawn from the −70° C. freezer the day of dosing and allowed to thaw at room temperature. VB4-845 may be prepared into the injection buffer in 4-6 hours of its removal from the −70° C. storage condition. Once the product is formulated into the injection buffer of phosphate-buffered saline, the product may be injected into the patient within six hours of preparation. If the product cannot be used within a suitable time course, a new vial may be obtained from the inventory for dosing.

VB4-845 is stable in its original packaging for at least 20 hours at room temperature, and if kept refrigerated (e.g., at 2-8° C.), for at least 24 hours. If the product is unused, it can be refrozen for later use, particularly if the original container/closure system remains intact.

Short term stability studies (up to 16 hrs incubation time) in biological fluid including human plasma, serum and urine demonstrated that VB4-845 retains it binding property and cell toxicity at least 16 hrs.

Example 4

In Vitro Pharmacology

Studies have been conducted to determine the in vitro cytotoxicity of VB4-845 to tumor cell cultures and in vivo efficacy models in animals.

To determine the ability of VB4-845 to specifically inhibit the growth of Ep-CAM-positive tumor cells, MTT (3-[4,5-dimethylthiazol-2-yl]-2,5-disphenyltetrazolium bromide) assays were performed[53]. The MTT assay measures the viability of cells by monitoring the reduction of the tetrazolium salt to formazan by enzymes contained only in live cells. Varying concentrations of VB4-845 were added to cell cultures and cell growth monitored over 72 hours.

VB4-845 is specifically cytotoxic against Ep-CAM-positive cell lines (e.g., HT29-colorectal carcinoma, MCF7-breast adenocarcinoma, CAL27-squamous cell carcinoma, SW2-small cell lung carcinoma) and does not affect the growth of the Ep-CAM-negative cell lines RL (e.g., non-Hodgkin's lymphoma) and COLO320 (colorectal carcinoma). SW2, CAL27 and MCF7 cells were found to be equally sensitive to the cytotoxic effect of VB4-845 and their proliferation was inhibited with an $IC_{50}$ of only 0.005 pM. HT29 cells were found to be the least sensitive ($IC_{50}$ of 0.2 pM).

*Pseudomonas* exotoxin irreversibly inhibits protein synthesis in mammalian cells by ADP-ribosylation of elongation factor 2[21-22]. To demonstrate that the cytotoxic activity of VB4-845 correlates with its ability to inhibit protein synthesis in Ep-CAM positive tumor cell lines, the uptake of a radioactively labeled metabolite, [³H]leucine, into Ep-CAM positive SW2 cells was monitored[53].

Upon treatment of SW2 cells with VB4-845 for a total of thirty hours, protein synthesis was inhibited with an $IC_{50}$ of 0.01 pM. This effect showed a similar dose response relationship to that previously measured in the cytotoxicity assay. 25 Protein synthesis in the Ep-CAM-negative control cell line, RL, was not affected.

Example 5

In Vivo Studies of Systemic Administration of VB4-845

Mice bearing large established Ep-CAM-positive SW2 (small cell lung cancer), HT29 (colorectal carcinoma) or CAL27 (HNSCC) tumor xenografts were treated intravenously (i.v.) with VB4-845 using 1 of 2 different dose regimens: 5 µg given every second day for 3 weeks (45 µg total); or 10 µg given every second day for 1 week (30 µg total). Mice bearing Ep-CAM-negative COLO320 tumor xenografts were used as controls. Tumor size was monitored over the course of the study (33-51 days post initiation of treatment)[53].

Figure 4:
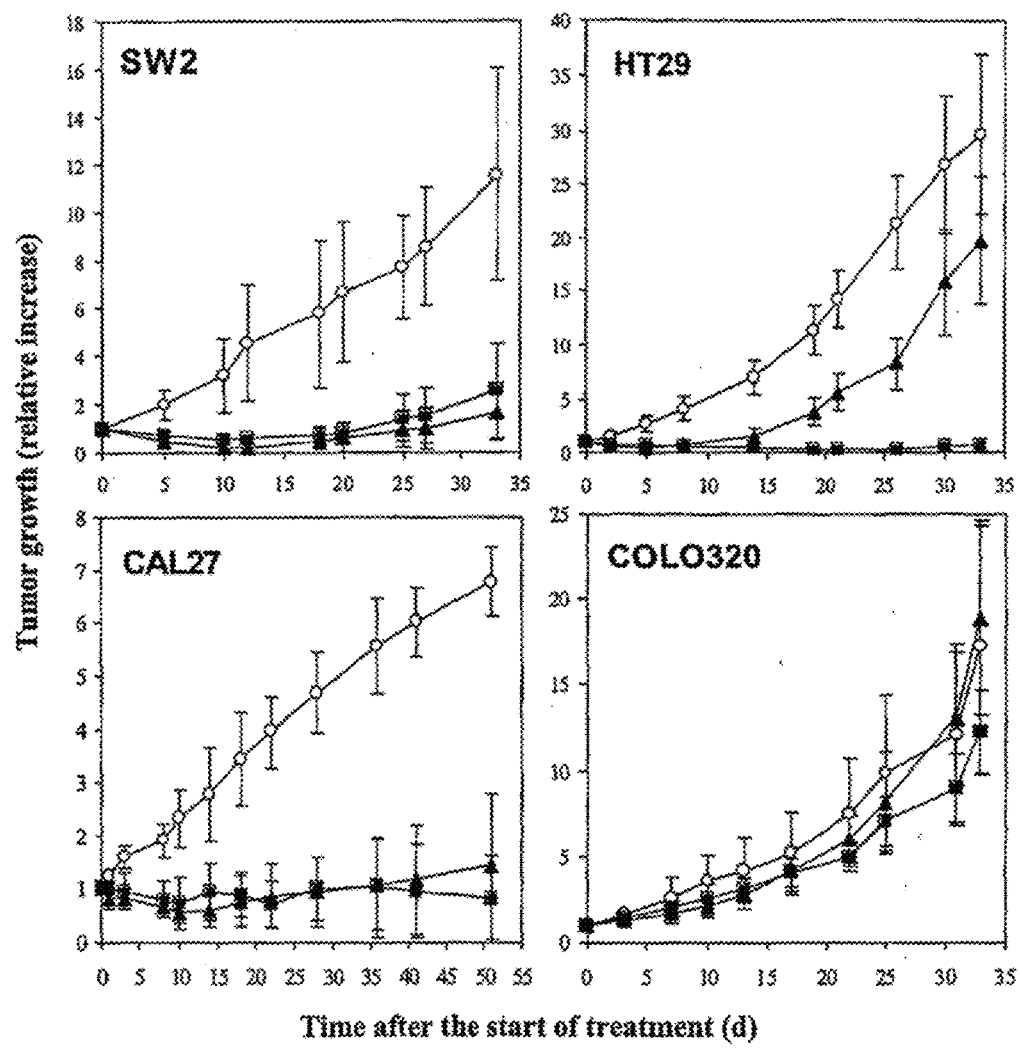
FIG. 4. Antitumor Effect of VB4-845 on Human Tumor Xenografts53. Athymic mice bearing Ep-CAM positive tumor xenografts (HT29, SW2, CAL27), or a negative control (COLO320 (o)) were treated i.v. every second day with VB4-845 at 5 µg (9 doses (■)) or 10 µg (3 doses (▲)). Tumor size is given relative to the initial median tumor size of 160 mm3.

The results are summarized in Table 4. The mice tolerated the treatments well, with no drug related mortalities and no significant clinical observations suggestive of toxicity. As shown in FIG. 4, significant inhibition of the growth of all Ep-CAM-positive tumors was achieved by treating mice with either dose schedule. Treatment of mice bearing SW2 xenografts resulted in shrinkage of the tumor volume to maximal 20% of the initial size and a slight resumption of growth to a final 2.6-fold size increase at the end of the monitored period. A similar effect was achieved upon treatment of CAL27 tumors, which were reduced to maximal 60% of the initial volume. Fifty days after start of the treatment, the median tumor volume did not exceed 1.4-fold the initial size. Two of seven mice treated with the 5 µg dose schedule showed complete tumor regression and remained tumor free. Neither CAL27 nor SW2 tumors showed a significant difference in their tumor response to the two treatment schedules.

For HT29 tumors, strong growth inhibition (0.7-fold of the initial volume) was achieved with the 5 µg dose schedule. As already observed for CAL27 tumors, 3 of 7 mice showed complete regression of their HT29 tumors. The efficacy of the 10 µg schedule was comparatively lower, indicating that for these tumors a long-term treatment is more effective. No antitumor effect of VB4-845 was seen in mice bearing Ep-CAM-negative COLO320 control tumors.

Example 6

In Vivo Studies of Direct Administration of VB4-845

Athymic mice were injected subcutaneously (s.c.) into the lateral flank with $10^7$ CAL27 HNSCC squamous cell carcinoma cells[54]. After four weeks when tumors had established, the mice were randomized into two groups with an average tumor volume of 150 mm³ each. Eight mice were treated by peritumoral injection of VB4-845 at a dose of 5 µg given every second day (Mon/Wed/Fri) for 3 weeks (total dose 45 µg). With each injection the 5 µg of immunotoxin were distributed into 2 to 3 injection spots. Control mice (n=5) remained untreated.

Figure 5:
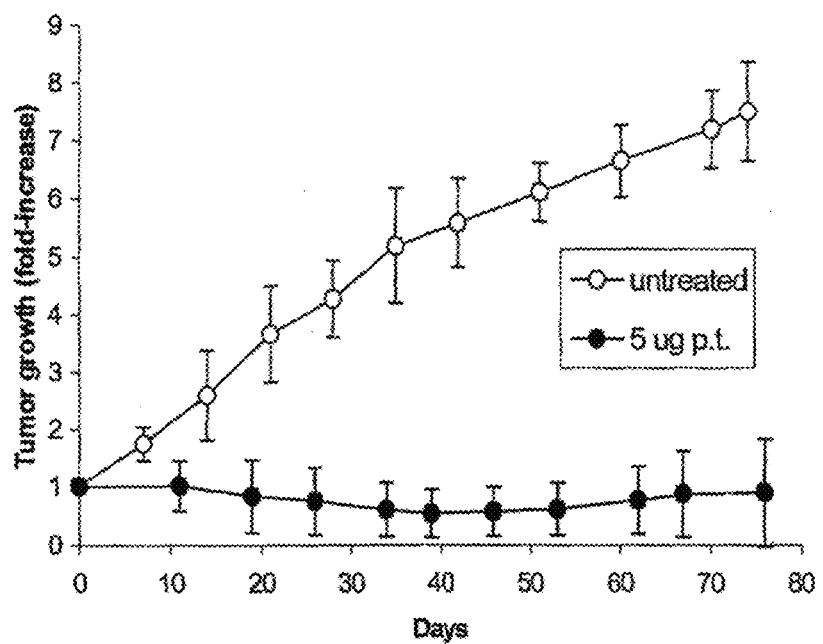
FIG. 5. Peritumoral Treatment of Athymic Mice Bearing CAL27 Tumor Xenografts. Athymic mice bearing Ep-CAM-positive CAL27 tumor xenografts were treated peritamorally every second day (Mon/Wed/Fri) with VB4-845 at 5 µg (9 doses). Tumor size is given relative to the initial median tumor size.

As summarized in Table 5, significant inhibition of tumor growth was observed in treated animals (FIG. 5). Two mice with smaller tumor volumes (90 mm³) at the start of treatment showed complete tumor regression and remained tumor free during the experiment. No toxicity could be observed during and after immunotoxin treatment.

Example 7

Biodistribution

In general, the literature indicates that scFv are cleared rapidly from the circulation, and give high tumor-to-background ratios (specific retention in tumor mass) at early time points in animal models[23-25]. $T_{1/2}$ on average are 2-4 hours[26-27], but can be longer (>8 hours) depending upon the construction of the molecule[28] and the route of administration. The highest uptake, depending on the molecule, tends to occur in the kidneys and liver after systemic infusion.

The biodistribution of VB4-845 has been assessed in mice bearing established Ep-CAM-positive SW2 and Ep-CAM-negative COLO320 xenografts at the contralateral flanks[53]. The maximum dose of radiolabeled VB4-845 detected in SW2 tumors was 2.93% ID/g after four hours, which then gradually decreased to 1.95% ID/g and 1.13% ID/g after at 24 and 48 hours, respectively. In contrast, VB4-15 845 in COLO320 control tumors localized with a maximum dose of 1.65% ID/g after thirty minutes, which then rapidly declined to 1.06% ID/g after four hours and showed only background levels after 48 hours.

VB4-845 showed a, slower blood clearance than the parental scFv. After 24 hours, the total dose of VB4-845 in the blood was 0.42% ID/g, which was 1.5-fold more than the parent scFv (0.28% ID/g). Moreover, localization of the immunotoxin in SW2 tumors was also delayed compared to the parent scFv, and the distribution of VB4-845 revealed a tumor:blood ratio of 5.38 after 48 hours, which was comparable to the ratio obtained with the scFv after 24 hours. At each time point, VB4-845 preferentially accumulated in Ep-CAM-positive SW2 tumors compared to COLO320 control tumor with a SW2:COLO320 ratio varying between 1.28 and 2.95. This indicates that VB4-845 was retained in Ep-CAM-positive tumors by specific antibody-antigen interactions and cellular uptake. The marginal accumulation in COLO320 control tumors may be due to the increase in vascular permeability often found in tumors. Analysis of normal tissues in these animals revealed that VB4-845 also localized in the kidney, spleen, liver and to a lower extent in the bone.

Clinical observations made during the conduct of the pharmacokinetic and efficacy models in mice indicate that the product was well tolerated without any clinical signs indicative of toxicity. All animals lived throughout the course of the studies and there was no drug related mortality.

Example 8

Toxicity Studies

A non-GLP study was performed to access the potential toxicity of escalating doses of VB4-845 on the 3 tissues, liver, spleen and bone, seen to have the highest level of localization of radiolabeled VB4-845 during the pharmacokinetic study.

Results are shown in Table 6.

Figure 6:
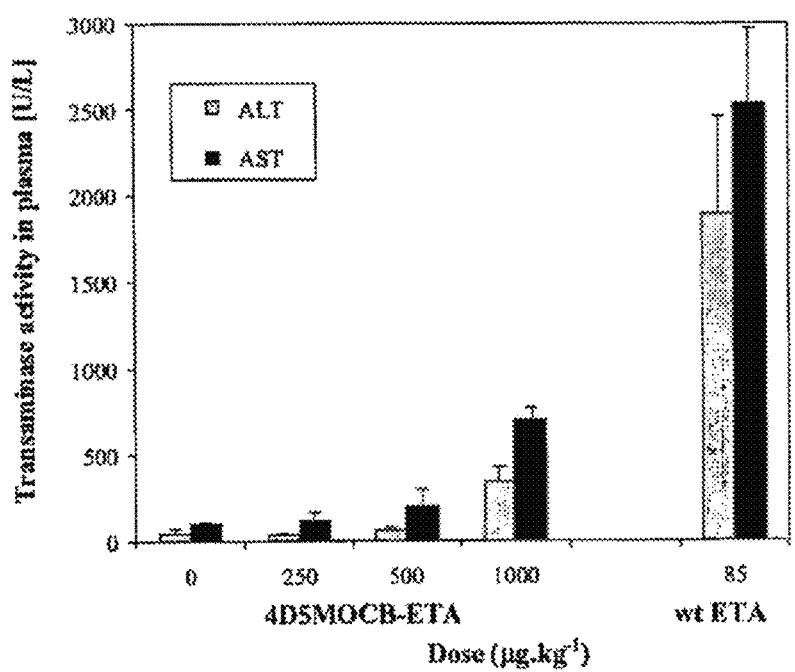
FIG. 6. Liver Function Upon Treatment With VB4-845 (4D5MOCB-ETA). For comparison, the transaminase activity of mice treated with a single lethal dose of wild-type ETA (85 µg/kg), as described by Schümann et al.[55-56], is also shown. Data are expressed as the mean±SD (n=3).

VB4-845 was administered to immunocompetent C57BL/6 mice, which are more sensitive to wild type ETA-mediated liver damage than the athymic mice used in the previous efficacy models, VB4-845 was administered to the mice i.v. at either 5 µg (250 µg/kg) or 10 µg (500 µg/kg) every other day for three doses, or 20 µg (1000 µg/kg) every other day for two doses. Twenty-four hours after the last dose, the activity of plasma transaminase was determined and compared to mice treated with PBS (thus 0 µg/kg VB4-845). No elevation of ALT/AST levels were observed in the plasma of mice 24 hours after completion of the 5 µg and 10 µg dose regimens (FIG. 6). Elevated transaminase activity was only observed upon administration of the 20 µg dose. At the 24 hour post-dose timepoint, the animals were sacrificed and tissue specimens from the livers and spleens were stained by hematoxylin/eosin and analyzed by light microscopy.

Figure 7:
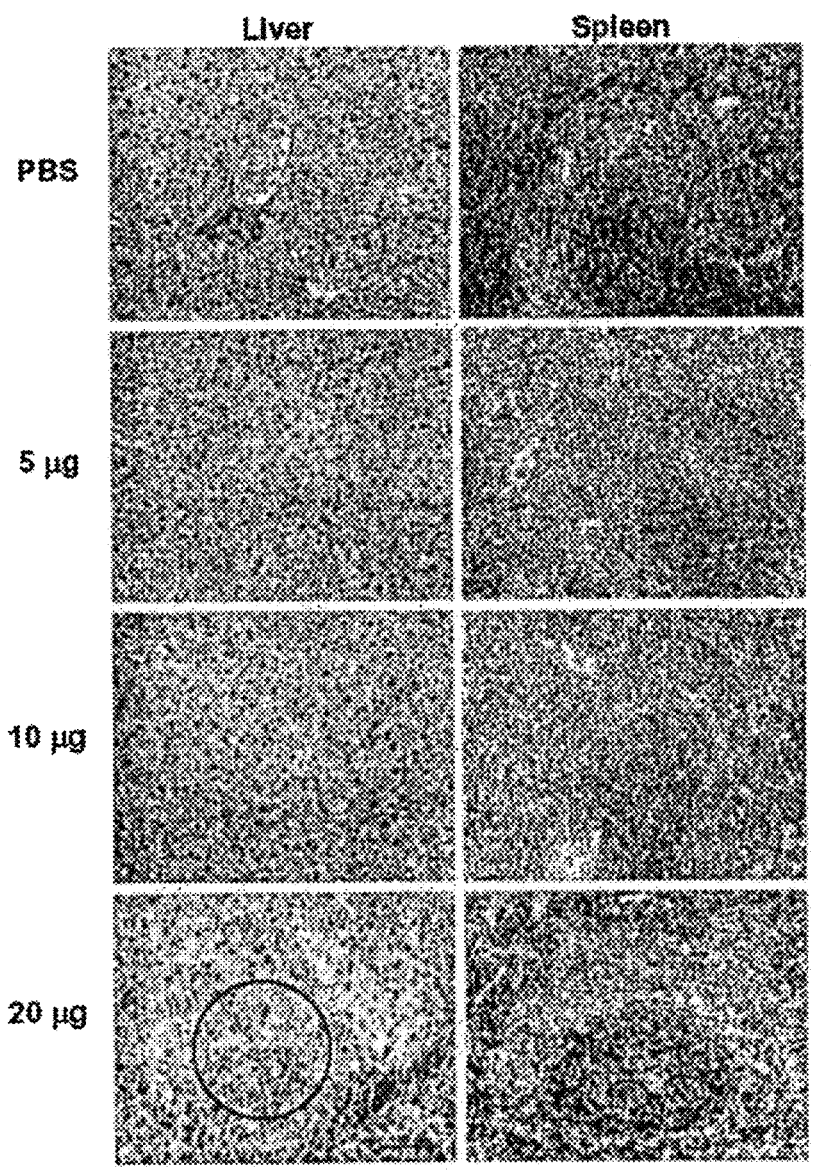
FIG. 7. Histopathological Results in Liver and Spleen Induced by VB4-845. Circle indicates area of necrotic hepatocytes in the 20 µg dose group.

Consistent with the transaminase activity seen, only a few sites with necrotic hepatocytes were found upon treatment with the 20 µg (1000 µg/kg) immunotoxin dosing regimen, total exposure 40 µg (2000 µg/kg) (FIG. 7). No signs of histopathological changes or myelosuppression were observed at any dose in spleen and cellular components of whole blood samples.

A low starting dose of VB4-845 in humans may be 20 µg (0.29 µg/kg for a 70 kg adult) given daily by micro-dose administration to different sections of the tumor each day for five days, with a single cycle cumulative exposure of 100 µg/tumor (1.43 µg/kg for a 70 kg adult). A higher dose may be 280 µg (4.0 (µg/kg for a 70 kg adult) given in the same fashion for a single cycle cumulative exposure of 1400 µg/tumor (20 µg/kg for a 70 kg adult). On a body weight basis, the starting dose is approximately 1585-fold less and the higher dose being 113-fold less than the monthly exposure by intravenous administration used in the above-described mouse studies (Table 7). Based on this safety margin, such a dose range is considered to be safe with respect to the doses used in a repeated fashion in mice that resulted in no clinical observations indicative of toxicity and the starting dose is 1056-fold lower than the monthly exposure to VB4-845 that showed no elevation in transaminase levels or histopathological changes in mice.

Single chain Fvs in rodents are cleared rapidly from the circulation, and give high tumor-to-background ratios (specific retention in tumor mass) at early timepoints[23-25], with $t_{1/2}$ on average 2-4 hours although this time can be longer[26-27].

Similar to results obtained in animals, $^{123}$I-labeled anti-CEA scFv demonstrated a relatively short half-life, for example, 0.42($t_{1/2}$) and 5($t_{1/2}$) hours in human patients[29]. Tumor to blood ratios increased with time (5.6:1 at 24 hours, compared to 1-1.5:1 for whole IgG anti-CEA antibody). Approximately 15-41% of the administered radioactivity was excreted in the urine within the first 24 hours, suggesting that the kidneys are the primary organ of excretion. Activity was seen in the liver after one hour, which activity decreased rapidly over the next 21 hours, and was observed in the gall bladder, consistent with biliary excretion of radionucleotide after liver catabolism of antibody[29]. A second study demonstrated a similar half-life of 0.32 ($t_{1/2}$) and 10.59 ($t_{1/2}$) hours, respectively[30]. The mean half-life for LMB-2, which is a scFv-ETA immunotoxin, varied from 173-494 minutes (monoexponential decay); however, this was partially related to disease burden in the peripheral blood and spleen[31-32].

PK studies of VB4-845 administered to humans can be evaluated, and such studies may encompass not only unconjugated toxin levels, but also those of anti-VB4-845 antibodies (neutralizing antibodies), along with antibodies to the toxin (Pseudomonas exotoxin A) in plasma. The PK of the free circulating toxin may be assessed in every patient, preferably hi the first cycle of treatment and follow-up. The neutralizing antibodies, and the anti-toxin antibodies may be assessed within the first cycle of treatment and follow-up. The time required to achieve peak circulating concentration ($T_{max}$) may he delayed due, for example, to an intratumoral route of administration. Moreover, the peak circulating concentration ($C_{max}$) may be reduced.

Monoclonal antibodies ("MABs") directed against lumphoma-associated antigens have been developed and clinically investigated for diagnosis and therapy of a number of human cancers. Toxicity relating to the administration of MABs or antibody fragments to humans have been reported, though primarily infusion related. Such toxicity events may include fever, chills, nausea and headach[14], uticaria, anaphylaxis, aseptic meningitis, hemolysis, leukopaenia, thrombocytopaenia, and vascular leak syndrome[33-35]. In come cases, these reactions may be partly attributable to the patient's immune response to foreign protein, since most clinical trials have used murine, or murine/human chimeric antibodies[33-34].

In contrast, VB4-845 is a humanized protein. Furthermore, in a preferred route of administration, intra- or peritumoral application of VB4-845 may not result in as many toxicity events, or to be similar degree of toxicity, as previously observed for other cancer immunotherapies.

Example 9

Preparation of VB4-845

Construction of the VB4-845 (also referred to as 4D5MOCB-ETA) expression vector. The sequence encoding a truncated form of ETA (ETA252-608) was amplified by PCR from plasmid pSW200[60] and cloned as an 1164 bp EcoRI-HindIII fragment downstream of the Ep-CAM-binding 4D5MOCB scFv sequence present in the pIG6-based[61] 4D5MOCB scFv expression vector.[62] The primers(Tox1: CTCGGAATTCGGTGGCGCGCCGGAGTTC-CCGAAACCGTCCACCCCGCCGGGTTCTTCTGGTT TA (SEQ ID NO:10); Tox2: GTCAAGCTrCTACAGT-TCGTCTTTATGGTGATGGTGGTGATGCGGCGGTTT CCCGGGCTG (SEQ ID NO: 11)) introduced an EcoRI restriction site between scFv and toxin and a C-terminal hexahistidine tag followed by the endoplasmic reticulum (ER) retention signal KDEL, a stop codon and a HindIII restriction site. To improve purity and yield during IMAC, a second hexahistidine tag was added at the N-terminus between the periplasmic signal sequence and the 4D5MOCB coding region. To this end, two pairs of oligonucleotides (Xbal 5': CTAGATAACGAGGGCAAAAAATGAAAAA-GACAGCTATCGCGATTGCAGTGGCACTGGCTG GTTTCGCTACCGT (SEQ ID NO: 12); Xbal 3':GCCACT-GCAATCGCGATAGCTGTCTTTTTCATTTT TTGC-CCTCGTTAT (SEQ ID NO: 13); and EcoRV 5': AGCO-CAGOCCGACCACCATCATCACCATCACGAT (SEQ ID NO:14); EcoRV 3': ATCGTGATGGTGATGATGGTG-GTCGGCCTGCGCTACGGTAGCGAAACCAGCCAGT (SEQ ID NO: 15)) were heated to 8Q° C., allowed to anneal by gradually cooling to room temperature and then ligated between the XbaI and EcoRV sites of pIG6-4D5MOCBETAH6KDEL. The sequence was experimentally confirmed.

For periplasmic expression of VB4-845, the vector pIG6 was used, which places the gene under lac promoter control in SB536, an E. coli strain devoid of the periplasmic proteases HhoA and HhoB.63. Five ml 2YT medium containing ampicillin (100 mg/ml) were inoculated with a single bacterial colony containing the VB4-845 (4D5MOCB-ETA) expression plasmid and grown overnight at 25° C. The bacteria were diluted in one liter of 2YT medium supplemented with 0.5% glucose and ampicillin (100 mg/ml) to reach an A55O nm between 0.1 and 0.2 and transferred to 3-liter baffled shake flasks. The culture was further grown at 25° C. to an A550 nm of 0.5 and immunotoxin production was induced for 4 h by adding a final concentration of 1 mM isopropyl-b-D-thiogalaetopyranoside (IPTG, Sigma). The harvested pellet derived from a bacterial culture with a final A550 nm of 6 was stored at −80° C.

For purification, the pellet obtained from a one liter culture was resuspended in 25 ml lysis buffer, containing 50 mM Tris-HCl (pH 7.5), 300 mM NaCl, 2 mM $MgSO_4$ and supplemented with EDTA-free protease inhibitor cocktail (Roche Diagnostics, Mannheim, Germany) and DNase I. The bacterial suspension was lysed with two cycles in a French Pressure Cell press (SLS Instruments, Urbana, Ill.), centrifuged at 48,000 g in a SS-34 rotor for 30 min at 4° C. and subsequently filter-sterilized (0.22 mm). The immunotoxin present in the cleared supernatant was purified by chromatography using a BIOCAD-System (Perseptive BioSystems) with a Ni2+-iminodiacetic (IDA) column and a HQ/M-anion-exchange column coupled in-line as described in Plūckthun et al.[64] Before the lysate was loaded, the Ni2+-IDA column was equilibrated with 20 mM Tris (pH 7.5), 300 mM NaCl. After loading, the column was washed three times with different salt solutions, all buffered with 20 mM Tris (pH 7.5), in the order 300 mM, 510 mM and 90 mM NaCl. Subsequently, the column was washed with 20 mM Tris (pH 7.5), 10 mM imidazole, 90 mM NaCl, before lie bound immunotoxin was eluted with the same solution containing 200 mM imidazole (pH 7.5).

The eluate was directly loaded onto the HQ/M-anion-exchange column and the bound immunotoxin was eluted with a salt gradient of 90-1000 mM NaCl, buffered with 20 mM Tris (pH 7.5). The fractions containing 4D5MOCB-ETA were collected and concentrated using a 10 kDa cutoff filter by centrifugation at 2000 g and 4° C. (Ultrafree-MC low protein binding, Millipore). The quality of purified VB4-845 (4D5MOCB-ETA) was analyzed by a 10% SDS-polyacrylamide gel and Western blotting using a horseradish peroxidase (HRP)-conjugated anti-tetrahistidine antibody (QIAGEN, Hilden, Germany) diluted 1:5000 according to the manufacturer's recommendations.

Analytical Gel Filtration and Determination of Thermal Stability.

Ten micrograms of purified VB4-845 (4D5MOCB-ETA) were diluted in 50 ml PBS pH 7.4 containing 0.005% Tween-20 and subsequently incubated at 37° C. Samples were analyzed at different time points (after 0 h, 2 h, 4 h, 8 h, 10 h and 20 h) by gel filtration using the Smart system (Pharmacia, Uppsala) with a Superose-12 PC3.2/30 column. The column was calibrated in the same buffer with three protein standards: alcohol dehydrogenase (Mr 150,000), bovine serum albumin (Mr 66,000) and carbonic anhydrase (Mr 29,000). The same analytical setting was used to assess the thermal stability of the 99 mTc-labeled immunotoxin after a 20 h incubation at 37° C. in human serum. The amount of immunotoxin monomers was determined by g-scintillation counting of the eluted fractions.

Radiolabeling and Determination of Antigen-Binding Affinity.

VB4-845 (4D5MOCB-ETA) was radioactively labeled by stable site-specific coordination of 99 mTc-tricarbonyl trihydrate to the hexahistidine tags present in the protein sequence.[65] This spontaneous reaction was induced by mixing 30 ml of immunotoxin solution (1 mg/ml) with one third volume of 1 M 2-[N-morpholino]ethanesulfonic acid (MES) pH 6.8 and one third volume of freshly synthesized 99 mTc-tricarbonyl compound. The mixture was incubated for 1 h at 37° C. and the reaction was stopped by desalting over a Biospin-6 column (BioRad, Hercules, Calif.) equilibrated with PBS containing 0.005% Tween-20, according to the manufacturer's recommendation. The percentage of immunoreactive immunotoxin was assessed as described by Lindmo et al.[66] The binding affinity of the 99 mTc-labeled immunotoxin was determined on SW2 cells in a radio-immunoassay (RIA), essentially as described for the scFv 4D5MOCB.

Example 10

VB4-84S Manufacturing Process

VB4-845 E. coli Fermentation.

The production of VB4-845 is carried out in 2 L shake flasks using a rotary incubator shaker in a research laboratory. The rotary shaker resides within an environmental control room where temperature can be regulated to within one degree Celsius. Inoculation of seed medium, production medium and all aseptic manipulations take place under a biological safety cabinet type II/B with HEPA filtration and air classification of 100. Cell separation, concentration and diafiltration take place in a research laboratory.

VB4-845 is produced from the VB4-845 E104 host cell E. coli Master Cell Bank (MCB) (Plasmid pING3302 from Xoma Ireland Ltd was used for the construction of the expression vector.). Initial scale-up of cell (fermentation) propagation for the production of clinical grade VB4-845 has been to the level of 26×2 L shake flasks with a working volume of 1 L per flask, total volume is 26 L. The VB4-845 E. coli MCB is grown in a complex nitrogen media containing glycerol as the principal carbon sources for cell growth. The fermentation procedure is described below.

Inoculum Preparation.

For a 26 L shake flask run, one 500 mL culture of VB4-845 E. coli MCB is prepared as pre-inoculum. For each culture, a vial of MCB is withdrawn from the −18° C. storage tank and allowed to thaw at room temperature. The vial is wiped externally with 70% ethanol and allowed to air dry in a biological safety cabinet. The cell suspension of MCB (1.5 ml) is added to a 2 L Erlenmeyer flask containing 500 mL of sterile seed medium (modified 2YT medium and 25 mg/L tetracycline). The flask is transferred to a rotary shaker set at 200 rpm and grown at 25±1° C. until an optical density of 3.0±0.2 or greater is reached (10.5±1 hr, mid-log phase of growth). The inoculum is then used as a seed culture to inoculate the 26 production shake flasks.

Fermentation in 26×2 L Shake Flasks.

Fermentation is carried out in 2 L-unbaffled flasks each containing 1 L of production medium. A typical production run for clinical grade VB4-845 has been 26×2 L flasks containing 1 L of production media (modified Terrific Broth, TB) per flask. The fermentation media is seeded with a 1% inoculum from the above culture and incubated on a shaker (200 rpm) at 25±1° C. until an optical density of 1.2 is reached (approximately 6-7 hours) at the last shake flask inoculated. A typical OD600 range at induction is 1.2-1.5. The VB4-845 expression is induced by the addition of 0.1% L-arabinose. Cells are harvested approximately 6 hours post-induction.

Cell Separation.

At harvest, all shake flasks are removed from the shaker room in the order of inoculation, with the first inoculated flask removed first. The content of the first shake flask is added to the second shake flask under a biological hood. All subsequent shake flasks are removed likewise. The pooled shake flasks are placed in refrigeration at 2-8° C. The VB4-845 E104 E. coli cells are removed in groups of 6 from the above fermentation cultures by centrifugation at 6,800 g force for 15 minutes at 2-8° C. in a Sorvall and Beckman centrifuges. The cells are discarded while the cell free broth is retained for further processing. The concentrated cell suspension is collected, inactivated and disposed of by established methods. The resulting supernatant is pooled and a 5 ml sample is reserved for product quantification. The centrifuges, rotors and centrifuge bottles are thoroughly cleaned prior to processing the fermentation broth.

Concentration/Diafiltration.

Concentration and diafiltration of harvested culture supernatant is performed by using a tangential flow Pellicon system with a Sartorius membrane (Hydrosart) molecular cut-off of 10 kD NMW (nominal molecular weight), and having a surface area of 3 square feet. The Pellicon filtration system is thoroughly washed prior to usage. Concentration is performed at a feed rate of 4 L/min and a permeate rate of 500 mL/min. A 5 ml sample is taken at the final concentration step. Diafiltration is performed against 0.02 M sodium phosphate, pH 7.2±0.2. Five volume changes are required to achieve the desired conductivity of <10 mS. The diafiltered concentrated product is clarified in a Sorvall centrifuge at 6,800 g force for approximately 30 minutes at a set temperature of 2-8° C. The clear solution-containing product of interest is filtered prior to purification using a 0.22 µm dead-end filter. The clarification step comprises, after diafiltration, centrifugation, passage through 0.2 µm Filter, addition of Triton X-100, adjustment of conductivity, adjustment of pH, and then follows purification.

VB4-845 Purification Procedures,

Purification of VB4-845 is performed in Viventia Biotech's Pilot Plant, a cGMP controlled area with HEPA filtration and controlled environmental with air Classification of 10,000. The VB4-845 protein is isolated by metal-affinity chelating chromatography and is further purified by an anion exchange chromatography elution. The purification process is summarized in the flow diagram in FIG. 9, and is described below.

Chelating Sepharose Metal Interaction Chromatography.

The metal-affinity column is prepared by packing Chelating Sepharose HP resin in a XK26/20 glass column, with a column volume of approximately 17±1 mL. The packing is performed at a backpressure of 3 bar. The working linear flow rate (LFR) is 90 cm/h. Five column volumes (CV) of Water for Injection (WFI) are passed through the Chelating Sepharose column. To charge the Chelating Sepharose column with metal ions, 5 CV of 0.1M nickel chloride solution is passed through the column. The remainder of the unbound nickel chloride is washed away with 5 CV of WFI. The column is then equilibrated with 10 CV of 20 mM sodium phosphate containing 150 mM sodium chloride and 0.1% Triton X-100, pH 7.2±0.1 buffer (chelating sepharose equilibration buffer).

The conductivity of the concentrated/diafiltered solution containing VB4-845 has been adjusted to 15±1 mS with sodium chloride and the pH is adjusted to 7.2±0.1 with 1M sodium hydroxide (NaOH). The VB4-845 containing solution is applied to the Chelating Sepharose HP column at a LFR of 90 cm/Hr or 8 ml/min. The column then is washed with 20 CV of wash buffer, 20 mM sodium phosphate, 150 mM sodium chloride, pH 7.2±0.1 buffer containing 20 mM imidazole and 0.1% Triton X-100 (wash buffer). The VB4-845 is eluted from the column with six CV of 20 mM sodium phosphate, 150 mM sodium chloride, pH 7.2±0.1 buffer, containing 500 mM imidazole (Chelating Sepharose elution buffer). The product is collected in a 3 CV fraction starting from the beginning of the elution peak.

Q-Sepharose-Anion Exchange Chromatography.

The Q-Sepharose HP resin is packed in a XK16/20 glass column with a final column volume of 5.0±0.5 mL. The operating linear flow rate is 156 cm/h. The column is washed with 10 CV of WFI, then washed with 5 CV of 1M sodium chloride in 20 mM sodium phosphate, pH 7.2±0.1 buffer and equilibrated with 10 CV 20 mM sodium phosphate, 90 mM sodium chloride, pH 7.2±0.1 buffer (2-sepharose equilibration buffer). The elution from the Chelating Sepharose column is diluted with 20 mM sodium phosphate, pH 7.2±0.1 buffer until a conductivity of 10±1 mS is achieved. The partially purified VB4-845 is loaded onto the Q-Sepharose column at a flow rate of 5.2 ml/min to further reduce endotoxin levels and DNA. Once the product has been bound, the anion exchange column is washed with 15 CV of Q-Sepharose equilibration buffer. The contaminants are found in the flow-through and wash steps. The product is eluted with 20 mM sodium phosphate, 500 mM sodium chloride, pH 7.2±0.1 buffer as a 3 mL fraction.

Example 11

VB4-845 Competition Assay

The Ep-Cam-positive cell line CAL-27 ($0.9 \times 10^6$) is pre-incubated with a non-saturating amount of biotinylated-VB4-845 scFv (0.5-1.0 µg) for 10 min at 4° C. in ice-cold PBS-5% FCS. After which, the test antibody (competitor) is diluted in ice-cold PBS-5% FCS and added to the mixture at an amount equimolar to the amount non-biotinylated VB4-845 scFv capable of completely inhibiting the binding of the biotinylated-VB4-845 scFv. Following the incubation for 1 hr at 4° C., the cells are washed with ice-cold PBS-5% FCS and incubated for an additional 30 min at 4° C. in the presence of Cy Chrome-conjugated streptavidin (Pharmingen, 1:120) diluted in wash buffer. The cells are washed at the end of the incubation period and analyzed by flow cytometry. As a negative control, CAL-27 tumor cells are incubated with 4B5 scFv, an anti-idiotype-specific scFv that reacts with the GD2-specific antibody 14G2a but not with CAL-27, in place of VB4-845 scFv. Alternatively, a non-competitor (anti-HER-2/neu) that binds to CAL-27 is added in place of 4B5 scFv. In either case, none to minimal change in median fluorescence is detected from that measured for biotinylated-VB4-845 scFv alone. For each antibody, the percent inhibition is calculated according to the following equation:

$$PI = [(F_{Max} - F_{Bgd}) - (F_T - F_{Bgd})/(F_{Max} - F_{Bgd})] \times 100$$

wherein:

PI=percent inhibition; $F_{max}$=maximal median fluorescence with biotinylated-VB4-845 scFv; $F_T$=median fluorescence of biotinylated-VB4-845 scFv in the presence of the test antibody; $F_{Bgd}$=background median fluorescence, the difference in median fluorescence between biotinylated-VB4-845 scFv alone and biotinylated-VB4-845 scFv in the presence of either of the negative control antibodies. Also see Willuda et al., 1998. "High thermal stability is essential for tumor targeting of antibody fragments: engineering of a humanized anti-epithelial glycoprotein-2 (epithelial cell adhesion molecule) single-chain Fv fragment," Cancer Res. 59:5758-5767.

Example 12

HNSCC Clinical Trials

In two clinical trials in HNSCC aimed primarily at determining the maximum tolerated dose and at evaluating different dosing protocols, subjects with advanced HNSCC will receive intratumoral injection of VB4-845 according to different dosing protocols. The starting dose (20 micrograms/tumour/day for 5 days) represent less than one-one-hundred-and-twentieth the highest single-dose intravenous exposure seen in 3-week mouse studies (on a body-surface-area basis) and less than one-seventieth the highest 5-day intravenous exposure in 3-week mouse studies (on a body-surface-area basis).

The first trial (an open-label, single arm, safety and tolerability study) is ongoing and has completed or initiated the treatment of at least 13 subjects. Two cycles of up to 130 microgram/tumour/day for 5 days (dose level 4; 650 microgram per tumour per cycle, total exposure of 1300 microgram per tumour) have been completed in most of these subjects. In this trial, the drug is injected directly at the site of the tumour or into one of the secondary growths (metastases) in the region of the head and the neck. The biggest or best accessible lesion is selected for injection (indicator or target lesion). The trial comprises a 2-cycle dose escalation scheme. Each cycle is of 4-weeks or 28-day duration. In the first 5 consecutive days of the cycle the subjects receive daily intratumoral injections of the drug with a starting dose of 20 microgram/tumour/day for 5 consecutive days, thus providing a 100 microgram per tumour per cycle (dose level 1). The 5-day period is followed by a 23-days rest period during which no drug will be administered. The subject will, however, undergo weekly follow-ups that include clinical examinations and testing of blood and urine samples. A second 28-days cycle is then repeated before final evaluation. A minimum of 1 and up to 3 subjects are dosed in each dose level. The 6 dose levels are 100, 200, 400, 650, 1000, and 1400 microgram/tumour/cycle (or 20, 40, 80, 130, 200 and 280 microgram/tumour/day for 5 consecutive days). On the morning of dosing, each vial is be diluted with up to 9000 µL of phosphate-buffered saline (PBS), and the required amount of VB4-845 is drawn into the syringe. The dilution rate is adjusted to achieve a volume to be injected not exceeding about 30% of the estimated volume of the tumour mass to be injected. In the 5-day period and the 24 hours following their last dose, the subjects are treated in an intensive care unit. Daily urine and blood 5 samples are taken to monitor liver and kidney functions and determine drug concentration in blood. On each dosing event, a single puncture of the skin or oral mucosa is made at a site approximately 80% of the distance from the tumour center out to the tumour periphery, ensuring that the puncture is at a different site from previous punctures. Six (6) to 8 needle tracks emanating out radially from the puncture site are made and equal volumes of solution are injected into each area. Adequate analgesics will be administered during treatment. Topical or systemic use of corticosteroids will be restricted to symptomatic skin or mucosal toxicity of grade 3 or 4.

In a second trial the drug is also injected directly at the site of the tumour or into one of the secondary growths (metastases) in the region of the head and the neck. If the subject has more than one lesion, the most accessible lesion approaching 5 cm in any greatest dimension will be injected. If only small lesions are available, multiple lesions can be treated for a combined greatest dimension of 5 cm. The subjects are dosed once a week, for four consecutive weeks. This 4-week period will be followed by a 4-week rest period during which the condition of the subject will be monitored. The initial dose level of VB4-845 is 100 µg/tumour/week and the other dose levels are 200, 330, 500, 700, 930 and 1240 microgram/tumour/week. On the morning of dosing, the vial(s) is(are) diluted with up to 800 µL of PBS, and then the required amount of VB4-845 is drawn into the syringe. The final volume to be injected is adjusted using a suspension volume of phosphate-buffered saline (PBS) so as not to exceed 30% of the estimated volume of the tumour mass to be injected. The drug is to be administered so as to attempt to include the entire volume of the tumour on each dosing day. To administer, small (25 to 27 gauge) needles attached to 1 cc Luer-lock syringes is inserted into the base of the tumour at an approximately 45-degree angle. Depending on the size and location of the tumour, the injection may be done by tracking the product through the tumour from a single puncture site or by injecting the tumour from multiple sites, in 1 cm increments, in parallel rows approximately 0.5 to 1.0 cm apart and disbursing throughout the tumour. Tumour response will be assessed before treatment at the baseline visit and pre-dose at each subsequent dose, at week 4 and at the end of the study. Where possible, a CT-scan will be performed at Screening, Week 4 and Week 8 (or final visit). In the event that a complete or partial response is observed, a CT scan will be performed 4 weeks later to confirm the result. Other assessments will be by direct measurement of the tumour by clinical observation and manipulation. A Complete response (CR) would indicate the complete disappearance of the injected tumour (confirmed at 4 weeks); Partial response (PR) a reduction by at least 30% in the largest diameter of the treated tumour (confirmed at 4 weeks); Stable disease by a regression of the treated tumour of less than 30% or progression less than 20% and Tumour progression (TP) an increase by 20% in the largest diameter of the treated tumour, where CR, PR or SD have not been previously documented. Pain will be assessed using an analog pain scale before treatment and prior to each dose and at Week 4 and Week 8 (or final visit). Random fine needle aspirate biopsies of the target tumour will be taken to explore the effects of VB4-845 at a cellular level. Systemic and local toxicity will be assessed using standard procedures and ongoing evaluations for adverse events, laboratory toxicities and subject pain status will occur throughout the treatment.

Example 13

Biological Activity of VB4-845 Against Bladder Tumor Cell Lines

Summary

VB4-845 [anti-Ep-CAM scFv and *Pseudomonas* exotoxin A lacking the cell binding domain (ETA252-608) fusion protein] was assessed by flow cytometry for cell-surface reactivity against a panel of human tumor cell lines including 14 bladder cancer cell lines to determine the degree and broadness of Ep-CAM expression in this potential clinical indications. VB4-845 demonstrated strong reactivity against 10 of 14 bladder cancer cell lines and weak reactivity against one other. VB4-845 demonstrated strong cytotoxicity on eleven VB4-845-positive bladder cancer cell lines; the IC50 values varied from 0.001-320 µM for a 72 hour exposure. In contrast, no cytotoxicity was detected against the three VB4-845-negative cell lines. Four bladder cancer cell lines (T-24, SW-870 UM-UC-10 and 1A6) were determined to be the most sensitive to VB4-845 treatment. In another experiment on a subset of cell lines where the exposure time was limited to 2 hours, VB4-845 exerted effective cytotoxicity (>93%) against the squamous bladder cancer cell line, SCaBER and the transitional bladder carcinoma cell line, 5637. In contrast, for a 2 hour exposure of 5637 to the control immunotoxin, 4B5-PE, non-specific cytotoxicity was shown to be minimal (<10%) at 500 pM and remained at the same level even after increasing the dose 100-fold (50000 pM). In summary, the potent in vitro antitumor activity of VB4-845 on bladder cancer cell lines suggests that VB4-845 has utility for pre-clinical and clinical development of anti-cancer therapy against bladder cancers.

Experimental Design

The experimental design for testing the reactivity of VB4-845 to tumor cell lines by flow cytometry and cytotoxicity have been described 3,4. Purified scFv-ETA fusion proteins, VB4-845 (Lot #02203, 1 mg/mL) and the negative control 4B5scFv-ETA (Lot #032403, 1.5 mg/mL) were generated as described and stored in aliquots at −80° C. The panel of tumor cell lines used in the study and their characteristics are in Table 9. All tumor cells were propagated in culture medium containing 10-20% FCS and appropriate supplements, following ATCC or ECACC protocols. Tumor cells were harvested when the cultures were 50-70% confluent with viability greater than 90%. The cell line CAL-27 expresses a high level of Ep-CAM antigen and was used as the positive control, while the low Ep-CAM expressing cell line COLO 320 was used as the negative control.

Testing Reactivity of VB4-845 Against Tumor Cell Lines by Flow Cytometry

Purified VB4-845 was tested against the panel of tumor cell lines to determine the cell-surface reactivity by flow cytometry. Briefly, tumor cells (0.9×106/300 µL) were incubated with purified VB4-845 or 4B5 scFv as a negative control, at 10 µg/mL for 2 hours on ice. Anti-EGFR mouse monoclonal antibody (Oncogene Research, Cat # OP15, at 1 µg/mL) was used as a positive control. After incubation, the cells were washed with PBS-5% FBS and incubated with either anti-HIS-Tag antibody (Amersham Pharmacia Cat #27-4710-01, diluted 1:800) for VB4-845 or biotin-conjugated anti-mouse IgG for anti-EGFR (Pierce cat #31174, diluted 1:200) for 1 hour on ice. The cells were washed with PBS-5% FBS, followed by incubation with either FITC-conjugated goat anti-mouse IgG (The binding Site Cat # AF271, diluted 1:100, for anti-HIS treated cells), or Streptavidin-Cy-Chrome (Pharmingen cat#13038A, diluted 1:120) for 30 minutes on ice. Finally, the cells were washed and resuspended in 0.5 mL of buffer containing propidium iodide (Molecular Probes cat# P-1304) at 0.6 µg/mL. Tumor cell binding was determined using a FACSCalibur. Antibodies were considered positive if antibody-treated tumor cells exhibited a positive shift in fluorescence resulting in >30% positive cells (1.3 times control) over the negative control.

Assessment of VB4-845-Mediated Cytotoxicity by Cell Proliferation Assay

VB4-845 cytotoxicity was measured by determining inhibition of cell proliferation by an MTS assay. Briefly, 96-well microtitre plates were prepared by seeding tumor cells at 5000 cells/50 µL/well in culture medium containing 10% FCS. The plates were incubated for 3 hours at 37° C. in the presence of 5% CO2. Ten-fold serial dilutions of VB4-845 were made at this time and varying amounts of VB4-845 (0.00005 to 500 µM) were added to each well in a 50 µL, volume, to bring the final volume to 100 µL. As a negative control, 4B5 scFv-ETA was used at the same concentrations. The control cells and the control (empty) wells were incubated with 100 µL of medium only, in quadruplets. The plates were incubated for 72 hours at 37° C. in the presence of 5% CO2. Each assay was repeated twice to demonstrate reproducibility and consistency in results. After incubation, an MTS assay was performed to measure cell viability. Briefly, 75 µL of phenazine methosulfate, PMS (0.92 mg/mL in PBS) was added to 1.5 mL of a tetrazolium compound, MTS (Promega, Cat # G111A and G109C, 2 mg/mL in PBS) and 20 µL of the PMS/MTS mixture was added to each well. The plates were incubated for 2 hours at 37° C. in the presence of 5% CO2. Subsequently, the plates were read at 490 nm using an ELISA plate reader.

Determination of the Minimal Immunotoxin Exposure Time Required for VB4-845-Mediated Cytotoxicity The IC50 (the VB4-845 concentration that kills fifty percent of cells compared to cells treated with medium only) was determined by exposing VB4-845 to each bladder cancer cell line for 72 hours. Five-sensitive cell lines of varying sensitivity to killing (SW-780, UC-MC-10, 1A6, UC-MC-14 and 5637) were selected to establish the minimal exposure time required for killing of 50% tumor cells using a fixed concentration that approximated the IC50. Tumor cells were exposed to VB4-845 at a fixed concentration (0.01, 0.6 or 6 µM) for 2, 4, 24, 48 and 72 hours. Except for 72 hours, at each time point, the medium containing VB4-845 was replaced with a fresh culture medium to minimize the immunotoxin (VB4-845) exposure time. MTS assay was performed after 72 hours of incubation to determine the cytotoxicity (50% tumor cell killing) compared to the control (cells with medium only). To further evaluate the effect of VB4-845 on a less sensitive squamous cell carcinoma cell line (SCaBER) and a sensitive a bladder transitional carcinoma cell line (5637) and two other bladder cancer cell lines (UM-UC-10 and UM-UC-14), cells were exposed to 2 hours with either fixed concentration or varying doses of VB4-845. After 2 hours of incubation, cells were washed to remove VB4-845, incubated with fresh medium and MTS assay was performed after 72 hours. Furthermore, to establish the specific cytotoxic effect of VB4-845, 5637 cells were exposed to varying doses (500, 5000, 50000 pM) of VB4-845 and the negative control immunotoxin, 4B5-PE to determine the effect of killing at higher concentrations. After incubation at each time points, 2, 6, 12, 24 and 48 hours, cells were washed with medium to remove VB4-845, incubated with fresh 1 medium and MTS assay was performed after 72 hours to determine cytotoxicity. The dose range was selected on the basis of initial IC50 results with the expectations that the minimal dose of VB4-845 being used to give maximal killing of this cell line.

Results

VB4-845 Tumor Cell Reactivity

The cell-surface reactivity of VB4-845 was assessed against a panel of bladder tumor cell lines. VB4-845 demonstrated positive reactivity against 11 of the 14 bladder cancer cell lines cell lines. The data are summarized in Table 10.

Cytotoxic Effect of VB4-845 Against Bladder Cancer Cell Lines In Vitro

Tumor cells were incubated with VB4-845 for 72 hours at concentrations ranging from 0.00005 to 500 pM and inhibition of cell proliferation was assessed by MTS assay. Results are summarized in Table 10. VB4-845 did not inhibition of cell proliferation in the three EGP-2-negative cell lines (J-82, UM-UC-3 and UM-UC-13) but showed strong inhibition (IC50 from 0.001-0.033 µM) in the four cell lines with very high expression of Ep-CAM antigen (T-24, SW-780, UM-UC-10 and 1A6 and intermediate inhibition in the other cell lines.

Minimal Exposure Time Required to Achieve VB4-845-Mediated Cytotoxicity Against Bladder Cancer Cell Lines In Vitro In the standard cell proliferation assay, bladder carcinoma cells were exposed to VB4-845 for 72 hours, after which the inhibition of cell proliferation was assessed. For bladder cancer, intravesical therapy dwell times are seldom longer than two hours. Therefore, a cell proliferation assay was performed to determine the minimal exposure time required to kill 50% tumor cells upon exposure to VB4-845 at a fixed concentration at or near IC50 (0.01 or 0.6 pM). In the first experiment, two VB4-845-sensitive bladder cancer cell lines (SW-780 and 1A6) were exposed to VB4-845 at 0.01 pM concentration for 2, 4, 6, 24, 48 or 72 hours. VB4-845 demonstrated strong cytotoxicity on the SW-780 and 1A6 bladder cancer cell lines even after short exposure time. For the highly sensitive bladder cancer cell line SW-780, (with an IC50 0.002 pM), 50% tumor cells were killed after 3 hours of exposure, whereas for a less sensitive cell line, 1A6, (IC50 0.033 pM), the same was achieved after 37 hours of exposure. A similar set of data was obtained in the second experiment, after exposure of three different bladder cancer cell lines to VB4-845 at 0.6 pM concentration. The results indicated that 50% of UM-UC-10, 5637 or UM-UC-14 cells were killed after 4, 16 and 20 hours of exposure, respectively. The rank order of sensitivity of these three lines was the same as for their IC50.

In a separate experiment, upon exposure to VB4-845 at a higher concentration (6.0 pM) for 2 hours, 96, 89 and 93% of UM-UC-10, 5637 and UM-UC-14 cells were killed, respectively. On further evaluation, after exposing a less-sensitive cell line (SCaBER) and a sensitive cell line (5637) for 2 hours with a varying dose of VB4-845, a strong cytotoxic effect with >93% killing of SCaBER cells was achieved with a 3900 pM dose, when the same degree of cytotoxicity was achieved with a much lesser dose (<498 pM) for 5637 cells. Thus, it was confirmed that the minimal dose of VB4-845 required for achieving maximal cytotoxic effect is dependent on the sensitivity of the cell line. Furthermore, in a separate experiment, exposure of 5637 to VB4-845 for 2 hours at 500 pM concentration demonstrated effective killing (>93%) of the cells with a minimal non-specific cytotoxicity (<10%) being demonstrated by the control immunotoxin (4B5-PE). In fact, for a 2 hour exposure, nonspecific killing was kept to a minimal level even after increasing the 4B5-PE concentration 100-fold.

Example 14

Human Clinical Bladder Binding

Surgical and necropsy human bladder tissue specimens were obtained and tested for Ep-CAM binding using VB4-845. The specimens were formalin-fixed and paraffin-imbedded. Method validation was conducted on both fresh-frozen and on fixed samples to confirm the adequacy of fixed specimen for this assay and to determine the optimal antibody (VB4-845) concentration to use (minimizing non-specific staining).

Seventeen bladder transitional cell carcinomas of Grade III and Stages II or III and 12 normal bladder control samples were stained with antibody VB4-845 at 4 micrograms/ml (~57 nM). Slide preparation and blocking were done according to well known immunohistochemistry procedures. The detection of VB4-845 bound to tissue was done using a rabbit anti-*Pseudomonas* exotoxin antibody (Sigma P2318), followed by a biotinylated anti-rabbit secondary antibody (Vector anti-rabbit BA-1000) and the Vector ABC-AP detection system using Vector red as substrate.

Carcinomas showed increased staining relative to normal transitional epithelium, and the strongest staining observed in the positive cases was membrane associated. Within carcinomas, the staining was variable in intensity and patchy in distribution. There was also an increased staining within areas exhibiting fair to moderate degrees of differentiation (i.e. transitional or columnar differentiation) compared to areas within the same tumor or tumors which showed less differentiation or high degrees of nuclear anaplasia and pleomorphism.

Of the 17 transitional carcinomas stained, eight samples showed areas of faint to moderate membrane staining (2-3 on a 0-4 staining intensity scale (Samples 2, 6, 8, 11, 13, 15, and 16), one showed areas of faint staining (Samples 9), and the other samples were negative for membrane staining. The staining was variable within the tumors, and appeared associated with the degree of differentiation within the sample. Within the 12 normal bladder samples, two samples showed faint and low frequency membrane staining (Samples 2 and 11). No staining was seen with a negative control immunotoxin (scFv-PE from an antibody to an irrelevant antigen).

Cytoplasmic and, more rarely, nuclear staining was seen in some normal and carcinoma specimens. In a validation study, higher concentration of VB4-845 resulted in more "blush" or cytoplasmic staining but in a more intense membrane staining on a higher percentage of carcinoma cells. In a clinical setting (in vivo) since the cytoplasm and nucleus are not exposed to the product a higher concentration of VB4-845 could be used to increase the binding to cells with lower number of receptors.

Example 15

Bladder Clinical Trial

In a clinical trial to evaluate the maximum tolerated dose of VB4-845, subjects with BCG-refractory transitional cell carcinoma (TCC) of the bladder, the drug is administered intravesically. The treatment cycle includes 6 weeks of therapy and 4 to 6 weeks of follow-up. The appropriate dose of VB4-845 will be administered via catheterization directly into the bladder (tumor) once per week for 6 consecutive weeks. The 7 dose levels of VB4-845 are 100, 200, 335, 500, 700, 930, and 1240 microgram in 50 ml at each of the 6 dosing day.

Immediately prior to drug administration, the bladder must be emptied after which a catheter will be inserted. For a male subject, a 16 French Coude catheter with a Urojet will be used and for a female subject, a 14 French red rubber catheter with sterile lubricant will be used. Reconstituted VB4-845 solution will be diluted in 50 ml of normal saline, instilled into an empty bladder via catheterization, and retained in the bladder for 2 hours with the catheter clamped in place. At the end of 2 hours, the bladder will be emptied by unclamping the catheter.

The safety, i.e. laboratory and adverse experience (AE) data at each dose level will be evaluated after 3 weeks of treatment prior to dose escalation. The subject will continue weekly therapy at the determined dose level for a period of 6 weeks or until there is a dose limiting toxicity (DLT) associated with the drug. Follow-up visits will be conducted within 4 to 6 weeks after the last week of drug administration. A subject who experiences a DLT, but shows clinical evidence of benefit to therapy will receive additional cycles of treatment at the next lowest dose level once all toxicities have resolved. Treatment will however be terminated for a subject who experiences a second DLT at the reduced dose. The response of the tumour will be evaluated by cytology, cytoscopy and biopsy.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

TABLE 1

Sample VB4-845 Product Specifications

| Test | Criteria |
| --- | --- |
| Appearance | Clear Solution at 2-8° C. |
| Protein (BCA) | 1.0 ± 0.2 mg/ml |
| $p$H | 7.2 ± 0.2 |
| SDS-PAGE (Non-Reducing: Coomassie Blue) | Major Band ~70 kDa (Area ≥90%) |
| Biological Activity (FACS) | ≥50 fold increase in fluorescence over the control antibody |
| Cytotoxicity ($IC_{50}$) | ≤0.50 pM |
| Total DNA | ≤1.0 ng/mg |
| Endotoxin (LAL) | ≤2000 EU/mg |
| Sterility | No Growth |

TABLE 2

Summary of Effect of VB4-845 against Tumor Cells In Vitro

| | |
|---|---|
| Test system Information: | University Hospital of Zürich, Department of Internal Medicine, Division of Medical Oncology, Zürich, Switzerland<br>Cell lines:<br>SW2 small cell lung carcinoma<br>CAL27 squamous cell carcinoma<br>HT29 colorectal carcinoma<br>COLO320 colorectal carcinoma<br>MCF7 breast adenocarcinoma<br>RL non-Hodgkin's lymphoma |
| Dosage Form: | VB4-845: 0.0001-100 pM |

TABLE 2-continued

Summary of Effect of VB4-845 against Tumor Cells In Vitro

| | |
|---|---|
| Assay: | MTT (3-[4,5-dimethylthiazol-2-yl]-2,5-disphenyltetrazolium bromide) assay |
| Duration of Study: | 72 hours |
| Parameters Evaluated: | Inhibition of cell growth by VB4-845 |
| Observed Effects and Conclusions: | SW2, CAL27 and MCF7 cells were found to be equally sensitive to the cytotoxic effect of VB4-845 ($IC_{50}$ = 0.005 pM). HT29 cells were found to be the least sensitive ($IC_{50}$ of 0.2 pM). |

TABLE 3

Summary Of Effect Of VB4-845 Agakst Protein Synthesis In Tumor Cells In Vitro

| | |
|---|---|
| Test system Information: | University Hospital of Zürich, Department of Internal Medicine, Division of Medical Oncology, Zürich, Switzerland<br>Cell lines:<br>SW2 small cell lung carcinoma<br>RL non-Hodgkin's lymphoma |

TABLE 3-continued

Summary Of Effect Of VB4-845 Agakst Protein Synthesis In Tumor Cells In Vitro

| | |
|---|---|
| Dosage Form: | VB4-845 - varying amounts |
| Assay: | Absorption of [4,5-$^3$H]leucine |
| Duration of Study: | 30 hours |
| Parameters Evaluated: | Uptake of [$^3$H]leucine (measure of protein synthesis) |
| Observed Effects and Conclusions: | Protein synthesis was inhibited by VB4-845 in Ep-CAM positive SW2 with an $IC_{50}$ of 0.01 pM. Protein synthesis in the Ep-CAM negative control cell line RL was not affected |

TABLE 4

Summary of Effect of VB4-845 on Solid Tumors in Mouse Xenograft Models of Cancer

| | |
|---|---|
| Test Animal Information: | Mouse, athymic nude<br>University Hospital of Zürich, Department of Internal Medicine, Division of Medical Oncology, Zürich, Switzerland<br>Animals implanted s.c. with one of:<br>SW2 small cell lung carcinoma<br>CAL27 squamous cell carcinoma<br>HT29 colorectal carcinoma<br>COLO320 colorectal carcinoma |
| Dosage Form: | VB4-845: 5 and 10 μg (see below) |
| Route of Administration: | Intravenous |
| Treatment Regimen: | i) 5 μg every second day for 3 weeks (45 μg total)<br>ii) 10 μg every second day for 1 week (30 μg total) |
| Duration of Study: | 50 days |
| Parameters Evaluated: | Primary tumor size |
| Observed Effects and Conclusions: | SW2: shrinkage of the tumor volume to maximal 20% of the initial size and a slight resumption of growth to a final 2.6-fold size increase at the end of the monitored period.<br>CAL27: tumors reduced to maximal 60% of the initial volume. The median tumor volume did not exceed 1.4-fold the initial size 50 days post treatment initiation. Two mice out of 7 treated with the 5 μg dose showed complete tumor regression and remained tumor free. Neither CAL27 nor SW2 tumors showed a significant difference in their tumor response to the 2 treatment schedules.<br>HT29: tumors size decreased 0.7-fold with 5 μg dose regimen. Three (3) out of 7 mice showed complete regression of their HT29 tumors. The efficacy of the 10 μg schedule was comparatively lower, indicating that for these tumors a long-term treatment is more effective.<br>No antitumor effect of VB4-845 was seen in mice bearing Ep-CAM-negative COLO320 control tumors. |

TABLE 5

Summary Of Effect Of Peritumoral Injection of VB4-845 On CAL27 Squamous Cell Carcinoma Tumors In Mouse Xenograft Models Of Cancer

| | |
|---|---|
| Test Animal Information: | Mouse, athymic nude<br>University Hospital of Zürich, Department of Internal Medicine, Division of Medical Oncology, Zürich, Switzerland<br>Animals implanted s.c. with CAL27 squamous cell carcinoma |
| Dosage Form: | VB4-845: 5 μg (see below) |
| Route of Administration: | Peritumoral |
| Treatment Regimen: | 5 μg every second day (Mon/Wed/Fri) for 3 weeks (45 μg total) |
| Duration of Study: | 80 days |
| Parameters Evaluated: | Primary tumor size |
| Observed Effects and Conclusions: | Significant inhibition of tumor growth was observed in treated animals. Two mice showed complete tumor regression and remained tumor free for the duration of the experiment. |

TABLE 6

Summary of Effect of Escalating Repeat Doses of VB4-845 on The Liver, Spleen and Bone of Immunocompetent Mice

| | |
|---|---|
| Test Animal Information: | Mouse, Immunocompetent C57BL/6 University Hospital of Zürich, Department of Internal Medicine, Division of Medical Oncology, Zürich, Switzerland |
| Dosage Form: | VB4-845: 5 µg (see below) <br> 10 µg <br> 20 µg |
| Route of Administration: | i.v |
| Treatment Regimen: | 5 or 10 µg every second day for 3 doses (15 or 30 µg total, respectively) <br> 20 µg every second day for 2 doses (40 µg total) |
| Study Groups: | 3 animals/group <br> 5 groups |
| Duration of Study: | 7 days |
| Parameters Evaluated: | Plasma ALT/AST <br> Histopathological findings, liver, spleen and bone |
| Observed Effects and Conclusions: | No elevation in liver enzymes 24 hours post final dose in the 5 or 10 µg dosing regimen mice. <br> Elevated ALT/AST levels observed 24 hours post final dose in the 20 µg dose animals. <br> No histopathological findings in the 5 and 10 µg dose groups. <br> A few sites with necrotic hepatocytes were found in the 20 µg treatment group. <br> No histopathological changes or myelosuppresion observed in any dose group in the spleen or cellular components of whole blood samples. |

TABLE 7

Relationship Between Doses Used in Mouse Studies and The Proposed Low and Higher Dose of VB4-845 in Humans.

| Species | Single Dose Exposure (µg/kg) Mouse | Multiple of Human Dose (Low/High Dose)[1] | Monthly Overall Exposure (µg * kg) Mouse | Multiple of Human Monthly Dose (Low/High Dose)[2] | Total Exposure (µg/kg) Mouse | Multiple of Total Human Dose (Low/High Dose)[3] |
|---|---|---|---|---|---|---|
| Athymic Mouse | 250 | 862/63 | 2250 | 1585/113 | 2250 | 523/38 |
| Athymic Mouse | 500 | 1724/125 | 1500 | 1056/75 | 1500 | 349/25 |
| Athymic Mouse | 250 | 862/63 | 2250 | 1585/113 | 2250 | 523/38 |
| C57BL/6 Mouse | 250 | 862/63 | 750 | 528/38 | 750 | 174/13 |
| C57BL/6 Mouse | 500 | 1724/125 | 1500 | 1056/75 | 1500 | 349/25 |
| C57BL/6 Mouse | 1000 | 3448/250 | 2000 | 1408/100 | 2000 | 465/33 |

[1] 0.29 and 4 µg/kg is the proposed low and higher single dose, respectively, for human administration (i.e., 20 µg and 280 µg administered to a 70 kg individual).
[2] 1.4 and 20 µg/kg is the proposed low and higher monthly dose, respectively, for human administration (i.e., 20 µg and 280 µg administered to a 70 kg individual each day for five consecutive days with a three-week washout period).
[3] 4.3 and 60 µg/kg is the proposed low and higher total dose, respectively, for human administration (i.e., 20 µg and 280 µg administered to a 70 kg individual each day for five consecutive days with a three-week washout period for 3 cycles).

TABLE 8

| Sample number | Carcinoma Grade | Carcinoma Stage | Positive Membrane Staining | % Cells Positive |
|---|---|---|---|---|
| 1 | III | II | — | — |
| 2 | III | II | Yes | 40% |
| 3 | III | II | — | — |
| 4 | III | II | — | — |
| 5 | III | II | — | — |
| 6 | III | II | Yes | 10% |
| 7 | III | II | — | — |
| 8 | III | II | Yes | 40% |
| 9 | III | III | Yes | 70% |
| 10 | III | III | — | — |
| 11 | III | III | Yes | 25% |
| 12 | III | III | — | — |
| 13 | III | III | Yes | 30-40% |
| 14 | III | III | — | — |
| 15 | III | III | Yes | 10% |
| 16 | III | III | Yes | 30% |
| 17 | III | III | — | — |

TABLE 9

Characteristics of Bladder Cancer Cell Lines

| Ref. no. | Bladder Cancer Cell Lines | Primary Tumour Tissue of Origin | Tumour Grade | Tumour Stage | Differentiation |
|---|---|---|---|---|---|
| 1 | 1A6 | Bladder TCC | High | Invasive | Well |
| 2 | T-24 | Bladder TCC | High | Invasive | Poor |
| 3 | SW-780 | Bladder TCC | Low | Invasive | No data |
| 4 | HT-1197 | Bladder TCC | High | Invasive | Poor |
| 5 | RT-4 | Bladder TCC | Low | Superficial (non-invas.) | Well |
| 6 | SCaBER | Bladder SqCC | No data | Invasive | Moderately |
| 7 | HT-1376 | Bladder TCC | High | Invasive | Poor |
| 8 | TCCSUP | Bladder TCC | High | Invasive | Poor |
| 9 | J-82 | Bladder SqCC | High | Invasive | Poor |
| 10 | UM-UC-3 | Bladder TCC | High | Invasive | Poor |
| 10 | UM-UC-13 | Bladder TCC | High | Invasive | No data |
| 11 | UM-UC-10 | No data | No data | No data | No data |
| 11 | UM-UC-14 | No data | No data | No data | No data |
| 1 | 5636 | Bladder TCC | High | Invasive | No data |

References:
1: A clone of the parent cell line, 5637, Immunobiol. 172: 175-184 (1986), Urol. Res. 21: 27-32 (1993);
2: Int. J. Cancer 11: 765-773 (1973), J. Urol. 149: 1626-1632 (1993);
3: Cancer Res. 44: 3997-4005 (1984);
4: J. Natl. Cancer Inst. 58: 881-890 (1977);
5: J. Urol. 161: 692-698 (1999);
6: Int. J. Cancer 17: 707-714 (1976);
7: J. Natl. Cancer Inst. 58: 881-890 (1977);
8: Br. J. Cancer 35: 142-151 (1977);
9: Br. J. Cancer 38: 64-76 (1978);
10: J. Urol. 146: 227-231 (1991);
11: AntiCancer Inc., Cell lines.
TCC: Transitional cell carcinoma.
SqCC: Squamous cell carcinoma.

TABLE 10

Tumor Cell-Surface Reactivity of VB4-845

| Bladder Cancer Cell Lines | Reactivity[1]: Fold-Increase in Fluorescence | Cytotoxicity $IC_{50}$ (pM) | Cytotoxicity: Relative Sensitivity vs. CAL27[2] |
|---|---|---|---|
| 1A6 | 154.7 ± 15.2 | 0.033 ± 0.01 | 8.8 |
| T-24 | 134.1 ± 35.9 | 0.001 ± 0.0 | 290 |
| UM-UC-10 | 124.6 ± 5.3 | 0.024 ± 0.00 | 12.1 |
| 5637 | 97.0 ± 11.2 | 0.38 ± 0.13 | 0.8 |
| SW-780 | 86.7 ± 3.1 | 0.002 ± 0.00 | 145 |
| HT-1197 | 56.5 ± 2.3 | 0.23 ± 0.05 | 1.3 |
| RT-4 | 55.3 ± 16.4 | 0.20 ± 0.10 | 1.4 |
| SCaBER | 54.0 ± 2.1 | 10.1 ± 6.1 | 0.03 |
| HT-1376 | 40.7 ± 0.3 | 3.3 ± 1.2 | 0.1 |
| UM-UC-14 | 25.7 ± 1.2 | 0.17 ± 0.2 | 1.6 |
| TCCSUP | 2.0 ± 0.1 | 320.0 ± 102.0 | 0.0009 |
| J-82 | 1.2 ± 0.1[2] | >500 | n/a |
| UM-UC-3 | 1.2 ± 0.1[2] | >500 | n/a |
| UM-UC-13 | 1.3 ± 0.1[2] | >500 | n/a |
| CAL-27 (Positive control) | 87.0 ± 3.0 | 0.29 ± 0.1 | 1.0 |
| COLO-320 (Negative control) | 1.1 ± 0.1[2] | >500 | n/a |

[1] Fold-increase in median fluorescence above the control. The values are expressed as mean ± SEM. The reactivity of the antibody for a given indication was determined by averaging mean-fold increase in median fluorescence calculated for each cell line in that indication.
[2] Cell lines showing a positive shift in fluorescence of <30% (1.3-fold increase) were considered negative.

REFERENCES

1. Chaubai S, Wollenberg B, Kastenbauer E, Zeidler R (1999) Ep-CAM—a marker for the detection of disseminated tumor cells in patients suffering from SCCHN. Anticancer Res JID—8102988 19:2237-2242
2. Salter E R, Tichansky D, Furth E E, Herlyn A M (2001) Tumor-associated antigen expression and growth requirements predict tumorigenesis in squamous cell carcinoma. In Vitro Cell Dev Biol Anim JID—9418515 37:530-535
3. Takes R P, Baatenburg dJ R, Schuuring E, Litvinov S V, Hermans J, van Krieken J H (1998) Differences in expression of oncogenes and tumor suppressor genes in different sites of head and neck squamous cell. Anticancer Res JID—8102988 18:4793-4800
4. Oppenheimer N J, Bodley J W (1981) Diphtheria toxin. Site and configuration of ADP-ribosylation of diphthamide in elongation factor 2. J Biol Chem JID—2985121R 256: 8579-8581
5. Kreitman R J (1999) Immunotoxins in cancer therapy. Curr Opin Immunol 11:570-578

6. Kreitman R J (2000) Immunotoxins. Expert Opin Pharmacother 1:1117-1129
7. Grossbard M L, Nadler L M (1993) Monoclonal antibody therapy for indolent lymphomas. Semin Oncol 20:118-135
8. Wahl R L (1994) Experimental radioimmunotherapy. A brief overview. Cancer 73:989-992
9. Grossbard M L, Fidias P (1995) Prospects for immunotoxin therapy of non-Hodgkin's lymphoma. Clin Immunol Immunopathol 76:107-114
10. Jurcic J G, Caron P C, Scheinberg D A (1995) Monoclonal antibody therapy of leukemia and lymphoma. Adv Pharmacol 33:287-314
11. Lewis J P, DeNardo G L, DeNardo S J (1995) Radioimmunotherapy of lymphoma: a UC Davis experience. Hybridoma 14:115-120
12. Uckun F M, Reaman G H (1995) Immunotoxins for treatment of leukemia and lymphoma. Leuk Lymphoma 18:195-201
13. Kreitman R J, Wilson W H, Bergeron K, Raggio M, Stetler-Stevenson M, FitzGerald D J, Pastan I (2001) Efficacy of the anti-CD22 recombinant immunotoxin BL22 in chemotherapy-resistant hairy-cell leukemia. N Engl J Med 345:241-247
14. Schwartzberg L S (2001) Clinical experience with edrecolomab: a monoclonal antibody therapy for colorectal carcinoma. Crit. Rev Oncol Hematol JID—8916049 40:17-24
15. Adkins J C, Spencer C M (1998) Edrecolomab (monoclonal antibody 17-1 A). Drugs JID—7600076 56:619-626
16. Litvinov S V, Velders M P, Bakker H A, Fleuren G J, Warnaar S O (1994) Ep-CAM: a human epithelial antigen is a homophilic cell-cell adhesion molecule. J Cell Biol JID—0375356 125:437-446
17. Willuda J, Honegger A, Waibel R, Schubiger P A, Stahel R, Zangemeister-Wittke U, Pluckthun A (1999) High thermal stability is essential for tumor targeting of antibody fragments: engineering of a humanized anti-epithelial glycoprotein-2 (epithelial cell adhesion molecule) single-chain Fv fragment. Cancer Res JID—2984705R 59:5758-5767
18. Proca D M, Niemann T H, Porcell A I, DeYoung B R (2000) MOC31 immunoreactivity in primary and metastatic carcinoma of the liver. Report of findings and review of other utilized markers. Appl Immunohistochem Mol Morphol JID—100888796 8:120-125
19. Pavlovskis O R, Gordon F B (1972) *Pseudomonas aeruginosa* exotoxin: effect on cell cultures. J Infect Dis JID—0413675 125:631-636
20. Leppla S H (1976) Large-scale purification and characterization of the exotoxin of *Pseudomonas aeruginosa*. Infect Immun JID—0246127 14:1077-1086
21. Kreitman R J, Pastan I (1998) Accumulation of a recombinant immunotoxin in a tumor in vivo: fewer than 1000 molecules per cell are sufficient for complete responses. Cancer Res JID—2984705R 58:968-975
22. Perentesis J P, Miller S P, Bodley J W (1992) Protein toxin inhibitors of protein synthesis. Biofactors JID—8807441 3:173-184
23. Milenic D E, Yokota T, Filpula D R, Finkelman M A, Dodd S W, Wood J F, Whitlow M, Snoy P, Schlom J (1991) Construction, binding properties, metabolism, and tumor targeting of a single-chain Fv derived from the pancarcinoma monoclonal antibody CC49. Cancer Res. 51:6363-6371
24. Yokota T, Milenic D E, Whitlow M, Schlom J (1992) Rapid tumor penetration of a single-chain Fv and comparison with other immunoglobulin forms. Cancer Res. 52:3402-3408
25. Verhaar M J, Keep P A, Hawkins R E, Robson L, Casey J L, Pedley B, Boden J A, Begent R H, Chester K A (1996) Technetium-99m radiolabeling using a phage-derived single-chain Fv with a C-terminal cysteine. J. Nucl. Med. 37:868-872
26. Adams G P, McCartney J E, Tai M S, Oppermann H, Huston J S, Stafford W F, Bookman M A, Fand I, Houston L L, Weiner L M (1993) Highly specific in vivo tumor targeting by monovalent and divalent forms of 741F8 anti-c-erbB-2 single-chain Fv. Cancer Res. 53:4026-4034
27. Deonarain M P, Rowlinson-Busza G, George A J, Epenetos A A (1997) Redesigned anti-human, placental alkaline phosphatase single-chain Fv: soluble expression, characterization and in vivo tumour targeting. Protein Eng. 10:89-98
28. Friedman P N, McAndrew S J, Gawlak S L, Chace D, Trail P A, Brown J P, Siegall C B (1992) BR96 sFv-PE40, a potent single-chain immunotoxin that selectively kills carcinoma cells. Cancer Res. 53:334-339
29. Begent R H, Verhaar M J, Chester K A, Casey J L, Green A J, Napier M P, Hope-Stone L D, Cushen N, Keep P A, Johnson C J, Hawkins R E, Hilson A J, Robson L (1996) Clinical evidence of efficient tumor targeting based on single-chain Fv antibody selected from a combinatorial library. NatMed. 2:979-984
30. Mayer A, Tsiompanou E, O'Malley D, Boxer G M, Bhatia J, Flynn A A. Chester K A, Davidson B R, Lewis A A, Winslet M C, Dhillon A P, Hilson A J, Begent R H (2000) Radioimmunoguided surgery in colorectal cancer using a genetically engineered anti-CEA single-chain Fv antibody. Clin Cancer Res 6:1711-1719
31. Kreitman R J, Wilson W H, Robbins D, Margulies I, Stetler-Stevenson M, Waldmann T A, Pastan I (1999) Responses in refractory harry cell leukemia to a recombinant immunotoxin. Blood 94:3340-3348
32. Kreitman R J, Wilson W H, White J D, Stetler-Stevenson M, Jaffe E S, Giardina S, Waldmann T A, Pastan I (2000) Phase I trial of recombinant immunotoxin anti-Tac(Fv)-PE38 (LMB-2) in patients with hematologic malignancies. J Clin Oncol 18:1622-1636
33, Bodey B, Siegel S E, Kaiser H E (1996) Human cancer detection and immunotherapy with conjugated and non-conjugated monoclonal antibodies. Anticancer Res. 16:661-674
34. Multani P S, Grossbard M L (1998) Monoclonal antibody-based therapies for hematologic malignancies. J. Clin. Oncol. 16:3691-3710
35. White C A, Larocca A, Grillo-Lopez A J (1999) Anti-CD20 monoclonal antibodies as novel treatments for non-Hodgkin's lymphoma. PSTT 2:95-101
36. Saleh M N, Posey J A, Khazaeli M B, Thurmond L M, Khor S P, Lampkin T A, Wissel P S, LoBuglio A F (1998) Phase I trial testing multiple doses of humanized monoclonal antibody (MAb) 3622W94. ASCO 1998 meeting #1680 (Abstract)
37. Raum T, Gruber R, RiethmuUer G, Kufer P (2001) Anti-self antibodies selected from a human IgD heavy chain repertoire: a novel approach, to generate therapeutic human antibodies against tumor-associated differentiation antigens. Cancer Immunol Immunother JED—8605732 50:141-150
38. Kroesen B J, Nieken J, Sleijfer D T, Molema G, de Vries E G, Grcen H J, Helfrich W, The T H, Mulder N H, de Leij L (1997) Approaches to lung cancer treatment using the CD3×EGP-2-directed bispecific monoclonal antibody BIS-1. Cancer Immunol Immunother JID—8605732 45:203-206
39. Haller D G (2001) Update of clinical trials with edrecolomab: a monoclonal antibody therapy for colorectal cancer. Semin Oncol 28:25-30
40. Riethmuller G, Holz E, Schlimok G, Schmiegel W, Raab R, Hoffken K, Gruber R, Funke I, Pichlmaier H, Hirche H, Buggisch P, Witte J, Pichlmayr R (1998) Monoclonal antibody therapy for resected Dukes' C colorectal cancer: seven-year outcome of a multicenter randomized trial, J Clin Oncol JID—8309333 16:1788-1794
41. Dencausse Y, Hartung G, Franz A, Strum J, Edler L, Bornbusch D, Gonnermann M, Post S, Hehlmann R, Queisser W (2000) Prospective randomized study of adjuvant therapy with edrecolomab (PANOREX) of stage II colon cancer: Interum analysis. Ann. Oncol. 11:47(Abstract)
42. de Boer C J, van Krieken J H, Janssen-van Rhijn C M, Litvinov S V (1999) Expression of Ep-CAM in normal, regenerating, metaplastic, and neoplastic liver. J Pathol JID—0204634 188:201-206
43. Balzar M, Winter M J, de Boer C J, Litvinov S V (1999) The biology of the 17-1A antigen (Ep-CAM). J Mol Med JID—9504370 77:699-712
44. Herlyn D, Sears H F, Ernst C S, Iliopoulos D, Steplewski Z, Koprowski H (1991) Initial clinical evaluation of two murine IgG2a monoclonal antibodies for immunotherapy of gastrointestinal carcinoma. Am J Clin Oncol JID—8207754 14:371-378
45. Begent R H, Chester K A (1997) Single-chain Fv antibodies for targeting cancer therapy. Biochem. Soc. Trans. 25:715-717
46. Chester K A, Mayer A, Bhatia J, Robson L, Spencer D I, Cooke S P, Flynn A A, Sharma S K, Boxer G, Pedley R B, Begent R H (2000) Recombinant anti-carcinoembryonic antigen antibodies for targeting cancer. Cancer Chemother Pharmacol 46 Suppl:S8-12
47. Chester K A, Bhatia J, Boxer G, Cooke S P, Flynn A A, Huhalov A, Mayer A, Pedley R B, Robson L, Sharma S K, Spencer D I, Begent R H (2000) Clinical applications of phage-derived sFvs and sFv fusion proteins. Dis Markers 16:53-62
48. Grossbard M L, Freedman A S, Ritz J, Coral F, Goldmacher V S, Eliseo L, Spector N, Dear K, Lambert J M, Blattler W A (1992) Serotherapy of B-cell neoplasms with anti-B4-blocked ricin: a phase I trial of daily bolus infusion. Blood 79:576-585
49. Amlot P L, Stone M J, Cunningham D, Fay J, Newman J, Collins R, May R, McCarthy M, Richardson J, Ghetie V (1993) A phase I study of an anti-CD22-deglycosylated ricin A chain immunotoxin in the treatment of B-cell lymphomas resistant to conventional therapy. Blood 82:2624-2633
50. Vitetta E S, Stone M, Amlot P, Fay J, May R, Till M, Newman J, Clark P, Collins R, Cunningham D (1991) Phase I immunotoxin trial in patients with B-cell lymphoma. Cancer Res 51:4052-4058
51. Stone M J, Sausville E A, Fay J W, Headlee D, Collins R H, Figg W D, Stetler-Stevenson M, Jain V, Jaffe E S, Solomon D, Lush R M, Senderowicz A, Ghetie V, Schindler J, Uhr J W, Vitetta E S (1996) A phase I study of bolus versus continuous infusion of the anti-CD19 immunotoxin, IgG-HD37-dgA, in patients with B-cell lymphoma. Blood JID—7603509 88:1188-1197
52. Messmann R A, Vitetta E S, Headlee D, Senderowicz A M, Figg W D, Schindler J, Michiel D F, Creekmore S, Steinberg S M, Kohler D, Jaffe E S, Stetler-Stevenson M, Chen H, Ghetie V, Sausville E A (2000) A phase I study of combination therapy with immunotoxins IgG-HD37-deglycosylated ricin A chain (dgA) and IgG-RFB4-dgA (Combotox) in patients with refractory CD19(+), CD22(+) B cell lymphoma. Clin Cancer Res JID—9502500 6:1302-1313
53. Di Paolo, C, Willuda, J., Kubetzko, S., Lauffer, I., Tschudi, D., Waibel, R., Pluckthun, A., Stahel, R. A., and Zangemeister-Witte, U. A recombinant immunotoxin derived from a humanized Ep-CAM-specific single-chain antibody fragment has potent and selective antitumor activity, (submitted)
54. Di Paolo, C. and Zangemeister-Witte, U., Personal communication, Zurich.
55. Schumann, J., Angermuller, S., Bang, R., Lohoff, M., and Tiegs, G. Acute hepatotoxiciry of *Pseudomonas aeruginosa* exotoxin A in mice depends on T cells and TNF. J. Immunol, 161: 5745-5754, 1998.
56. Schümann, J., Wolf, D., Pahl, A., Brune, K., Papadopoulos, T., van Rooijen, N., and Tiegs, G. Importance of Kupffer cells for T-cell-dependent liver injury in mice. Am. J. Pathol, 157: 1671-1683, 2000.
57. Sizmann N and Korting H C, Prolonged Urticaria with 17-1A Antibody. BMJ 317:1631. F Fichtner I, Kufer P, Raum T, Riethmuller G, Baeuerle P A, Dreier T. In vitro and in vivo activity of MT201, a fully human monoclonal antibody for pancarcinoma treatment. Int J Cancer 100(i): 101-10, 2002.
59. Willuda J, Honegger A, Waibel R, Schubiger P A, Stahel R, Zangemeister-Wittke U, Pluekthun A. High thermal stability is essential for tumor targeting of antibody fragments: engineering of a humanized anti-epithelial glycoprotein-2 (epithelial cell adhesion molecule) single-chain Fv fragment. Cancer Res 59(22):5758-67, 1999
60. Wels, W., Beerli, R., Hellmann, P., Schmidt, M., Marte, B. M., Kornilova, E. S., Hekele, A., Mendelsohn, J., Groner, B., and Hynes, N. E. EGF receptor and p185erbB-2-specific single-chain antibody toxins differ in their cell killing activity on tumor cells expressing both receptor proteins. Int. J. Cancer, 60: 137-144, 1995.
61. Ge, L., Plückthun, A., Pack, P., Freund, C, and Pluckthun, A. Expressing antibodies in *Escherichia coli*. In C. A. K. Borrebaeck (ed.), Antibody engineering, pp. 229-261. Oxford: Oxford University Press, 1995.
62. Willuda, J., Honegger, A., Waibel, R., Schubiger, P. A., Stahel, R., Zangemeister-Wittke, U., and Pliickthun, A. High thermal stability is essential for tumor targeting of antibody fragments: engineering of a humanized anti-epithelial glycoprotein-2 (epithelial cell adhesion molecule) single-chain Fv fragment. Cancer Res., 59: 5758-5767, 1999.
63. Bass, S., Gu, Q., and Christen, A. Multicopy suppressors of prc mutant *Escherichia coli* include two HtrA (DegP) protease homologs (HhoAB), DksA, and a truncated RlpA. J. Bacteriol, 178: 1154-1161, 1996.
64. Pluckthun, A., Krebber, A., Krebber, C, Horn, U., Kntipfer, U., Wenderoth, R., Nieba, L., Proba, K., and Riesenberg, D. Producing antibodies in *Escherichia Coli*: from PCR to fermentation. In J. McCafferty, H. R. Hoogenboom, and D. J. Chiswell (eds.), Antibody engineering, pp. 203-252. Oxford: IRL Press, 1996.
65. Waibel, R., Alberto, R., Willuda, J., Finnern, R., Schibli, R., Stichelberger, A., Egli, A., Abram, U., Mach, J. P., Plückthun, A., and Schubiger, P. A. Stable one-step technetium-99m labeling of His-tagged recombinant proteins with a novel Tc(I)-carbonyl complex. Nat. Biotechnol., 17: 897-901, 1999.
66. Lindmo, T., Boven, E., Cuttitta, F., Fedorko, J., and Bunn, P. A., Jr. Determination of the immunoreactive fraction of radiolabeled monoclonal antibodies by linear extrapolation to binding at infinite antigen excess. J. Immunol. Methods, 72: 77-89, 1984.

ABBREVIATIONS

ADME: administration, distribution, metabolism and excretion
ADP: adenosine phosphate
ALT: alanine aminotransferase (SGPT)
AST: aspartate aminotransferase (SGOT)
BCA: bieinchoninic acid method
$C_{max}$: maximum concentration
DNA: deoxyribonucleic acid
Ep-CAM: epithelial cell adhesion molecule
ETA: *Pseudomonas* exotoxin A
EU: endotoxin units
FACS: fluorescence activated cell sorter method
GLP: good laboratory practices
HNSCC: squamous cell carcinoma of the head and neck
$IC_{50}$: inhibitory concentration 50%
i.t. intratumoral
i.v. intravenous
kDa: kilodalton
LAL: *Limulus amebocyte* lysate
MAbs: monoclonal antibodies
mg: milligram
mL: milliliter
mM: millimolar
MTD: maximum tolerated dose
MTT: 3-[4,5-dimethylthiazol-2-yl]-2,5-disphenyltetrazolium
NaCl: Sodium chloride
ng: nanogram
PBS: phosphate buffered saline
pi: isoelectric point
PK: pharmacokinetics
pM: picomolar
p.t: peritumoral
s.c: subcutaneous
scFv; single chain antibody fragment
SCLC: small cell lung cancer
SD: standard deviation
SDS PAGE: sodium dodesyl sulfate polyacrylamide gel electrophoresis
$t_{1/2}$ half-life
$T_{max}$ time to maximum
μg microgram
VLS: vascular leak syndrome
WHO: World Health Organization
wt: wild type The present invention is not to be limited in scope by the specific embodiments described above. Many modifications of the present invention, in addition to those specifically recited above would be apparent to those skilled in the art in light of the instant disclosure. These modifications are intended to fall within the scope of the appended claims. All publications and patents cited above are herein incorporated by reference in their entireties.

What is claimed is:

1. An immunotoxin comprising from amino acid 23 to amino acid 669 of SEQ ID NO:2.

2. The immunotoxin of claim 1, wherein the immunotoxin comprises the amino acid sequence of SEQ ID NO: 2.

3. A method of treating bladder cancer comprising administering, directly to the cancer site, an effective amount of an immunotoxin to an animal in need thereof, wherein said immunotoxin comprises the amino acid sequence from amino acid 23 to amino acid 669 of SEQ ID NO: 2.

4. The method of claim 3, wherein the immunotoxin is VB4-845 consisting of the amino acid sequence from amino acid 23 to amino acid 669 of SEQ ID NO: 2.

5. A method for treating bladder cancer comprising:
testing a tumor sample from a patient for the expression of a protein suspected of being associated with bladder cancer wherein the protein is Epithelial Cell Adhesion Molecule (Ep-CAM); and
if the protein is expressed at greater levels in the tumor sample as compared to a control, administering to the patient, directly to the cancer site, an effective amount of immunotoxin, comprising the amino acid sequence from amino acid 23 to amino acid 669 of SEQ ID NO: 2.

6. The method of claim 3 wherein the animal in need thereof is a human.

7. The method of claim 3 wherein the immunotoxin is administered to the animal before, during or after surgery.

8. The method of claim 3 wherein the immunotoxin is administered to the animal before, during or after radiation therapy.

9. The method of claim 3 wherein the immunotoxin is administered to the animal before, during or after one or more chemotherapeutic agents.

10. The method of claim 9 wherein the one or more chemotherapeutic agent is one or more of cisplatin, fluorouracil, carboplatin, mitomycin C, doxorubicin, gemcitabine, or paclitaxel.

11. The method of claim 10 wherein the one or more chemotherapeutic agent is flurouracil.

12. The method of claim 10 wherein the one or more chemotherapeutic agent is one or more of mitomycin C, doxorubicin, or gemcitabine.

13. The method of claim 3 wherein the immunotoxin is administered once per week for 6 weeks.

14. The method of claim 3 wherein the immunotoxin is administered to an animal in combination with one or more agents that increases expression of EpCAM in the tumor cells.

15. The method of claim 14 wherein the one or more agents that increases expression of EpCAM in the tumor cells is vinorelbine tartrate and/or paclitaxel.

16. The method of claim 3 wherein the immunotoxin is administered with a catheter directly into the bladder of said animal.

17. The method of claim 3 wherein the bladder cancer is BCG refractory transitional carcinoma.

18. The method of claim 3 wherein the treating comprises decreasing the size, growth rate, invasiveness, malignancy grade and/or risk of recurrence of a tumor associated with the bladder cancer.

* * * * *

SEQUENCE LISTING

```
<160> NUMBER OF SEQ ID NOS: 15

<210> SEQ ID NO 1
<211> LENGTH: 2084
<212> TYPE: DNA
<213> ORGANISM: Artificial Sequence
<220> FEATURE:
<223> OTHER INFORMATION: VB4-845
<220> FEATURE:
<221> NAME/KEY: CDS
<222> LOCATION: (66)..(2084)

<400> SEQUENCE: 1
gaattcctgc aggtctatgg aacgataaat gcccatgaaa attctatttc aaggagacag        60 tcata atg aaa tac cta ttg cct acg gca gcc gct gga ttg tta tta ctc      110
      Met Lys Tyr Leu Leu Pro Thr Ala Ala Ala Gly Leu Leu Leu Leu
      1               5                  10                  15 gct gcc caa cca gcg atg gcg cac cat cat cac cat cac gat atc cag        158
Ala Ala Gln Pro Ala Met Ala His His His His His His Asp Ile Gln
                 20                  25                  30 atg acc cag tcc ccg tcc tcc ctg agt gct tct gtt ggt gac cgt gtt        206
Met Thr Gln Ser Pro Ser Ser Leu Ser Ala Ser Val Gly Asp Arg Val
             35                  40                  45 acc atc acc tgc cgt tcc acc aaa tcc ctc ctg cac tcc aac ggt atc        254
Thr Ile Thr Cys Arg Ser Thr Lys Ser Leu Leu His Ser Asn Gly Ile
         50                  55                  60 acc tac ctt tat tgg tat caa cag aaa ccg ggt aaa gct ccg aaa ctt        302
Thr Tyr Leu Tyr Trp Tyr Gln Gln Lys Pro Gly Lys Ala Pro Lys Leu
     65                  70                  75 ctg atc tac cag atg tcc aac ctg gct tcc ggt gtt ccg tct cgt ttc        350
```

|  |  |  |  |  |  |  |  |  |  |  |  |  |  |  |  |
|---|---|---|---|---|---|---|---|---|---|---|---|---|---|---|---|
| Leu | Ile | Tyr | Gln | Met | Ser | Asn | Leu | Ala | Ser | Gly | Val | Pro | Ser | Arg | Phe |
| 80 |  |  |  |  | 85 |  |  |  |  | 90 |  |  |  |  | 95 |

| tcc | agt | tct | ggt | tct | ggt | acc | gac | ttc | acc | ctg | acc | atc | tct | tct | ctg | 398 |
|---|---|---|---|---|---|---|---|---|---|---|---|---|---|---|---|---|
| Ser | Ser | Ser | Gly | Ser | Gly | Thr | Asp | Phe | Thr | Leu | Thr | Ile | Ser | Ser | Leu |  |
|  |  |  |  |  | 100 |  |  |  |  | 105 |  |  |  |  | 110 |  |

| cag | ccg | gaa | gac | ttc | gct | acc | tac | tac | tgc | gct | cag | aac | ctg | gaa | atc | 446 |
|---|---|---|---|---|---|---|---|---|---|---|---|---|---|---|---|---|
| Gln | Pro | Glu | Asp | Phe | Ala | Thr | Tyr | Tyr | Cys | Ala | Gln | Asn | Leu | Glu | Ile |  |
|  |  |  | 115 |  |  |  |  | 120 |  |  |  |  | 125 |  |  |  |

| ccg | cgt | acc | ttc | ggt | cag | ggt | acc | aaa | gtt | gaa | ctt | aag | cgc | gct | acc | 494 |
|---|---|---|---|---|---|---|---|---|---|---|---|---|---|---|---|---|
| Pro | Arg | Thr | Phe | Gly | Gln | Gly | Thr | Lys | Val | Glu | Leu | Lys | Arg | Ala | Thr |  |
|  |  | 130 |  |  |  |  | 135 |  |  |  |  | 140 |  |  |  |  |

| ccg | tct | cac | aac | tcc | cac | cag | gtt | cca | tcc | gca | ggt | ggt | ccg | act | gct | 542 |
|---|---|---|---|---|---|---|---|---|---|---|---|---|---|---|---|---|
| Pro | Ser | His | Asn | Ser | His | Gln | Val | Pro | Ser | Ala | Gly | Gly | Pro | Thr | Ala |  |
|  | 145 |  |  |  |  | 150 |  |  |  |  | 155 |  |  |  |  |  |

| aac | tct | gga | act | agt | gga | tcc | gaa | gta | cag | ctg | gtt | cag | tcc | ggc | ccg | 590 |
|---|---|---|---|---|---|---|---|---|---|---|---|---|---|---|---|---|
| Asn | Ser | Gly | Thr | Ser | Gly | Ser | Glu | Val | Gln | Leu | Val | Gln | Ser | Gly | Pro |  |
| 160 |  |  |  |  | 165 |  |  |  |  | 170 |  |  |  |  | 175 |  |

| ggt | ctt | gtt | caa | ccg | ggt | ggt | tcc | gtt | cgt | atc | tct | tgc | gct | gct | tct | 638 |
|---|---|---|---|---|---|---|---|---|---|---|---|---|---|---|---|---|
| Gly | Leu | Val | Gln | Pro | Gly | Gly | Ser | Val | Arg | Ile | Ser | Cys | Ala | Ala | Ser |  |
|  |  |  | 180 |  |  |  |  | 185 |  |  |  |  | 190 |  |  |  |

| ggt | tac | acg | ttc | acc | aac | tac | ggc | atg | aac | tgg | gtc | aaa | cag | gct | ccg | 686 |
|---|---|---|---|---|---|---|---|---|---|---|---|---|---|---|---|---|
| Gly | Tyr | Thr | Phe | Thr | Asn | Tyr | Gly | Met | Asn | Trp | Val | Lys | Gln | Ala | Pro |  |
|  |  | 195 |  |  |  |  | 200 |  |  |  |  | 205 |  |  |  |  |

| ggt | aaa | ggc | ctg | gaa | tgg | atg | ggc | tgg | atc | aac | acc | tac | acc | ggt | gaa | 734 |
|---|---|---|---|---|---|---|---|---|---|---|---|---|---|---|---|---|
| Gly | Lys | Gly | Leu | Glu | Trp | Met | Gly | Trp | Ile | Asn | Thr | Tyr | Thr | Gly | Glu |  |
|  |  | 210 |  |  |  |  | 215 |  |  |  |  | 220 |  |  |  |  |

| tcc | acc | tac | gct | gac | tcc | ttc | aaa | ggt | cgc | ttc | act | ttc | tcc | ctc | gac | 782 |
|---|---|---|---|---|---|---|---|---|---|---|---|---|---|---|---|---|
| Ser | Thr | Tyr | Ala | Asp | Ser | Phe | Lys | Gly | Arg | Phe | Thr | Phe | Ser | Leu | Asp |  |
| 225 |  |  |  |  | 230 |  |  |  |  | 235 |  |  |  |  |  |  |

| aca | agt | gct | agt | gct | gca | tac | ctc | caa | atc | aac | tcg | ctg | cgt | gca | gag | 830 |
|---|---|---|---|---|---|---|---|---|---|---|---|---|---|---|---|---|
| Thr | Ser | Ala | Ser | Ala | Ala | Tyr | Leu | Gln | Ile | Asn | Ser | Leu | Arg | Ala | Glu |  |
| 240 |  |  |  |  | 245 |  |  |  |  | 250 |  |  |  |  | 255 |  |

| gat | aca | gca | gtc | tat | tac | tgc | gcc | cgt | ttc | gct | atc | aaa | ggt | gac | tac | 878 |
|---|---|---|---|---|---|---|---|---|---|---|---|---|---|---|---|---|
| Asp | Thr | Ala | Val | Tyr | Tyr | Cys | Ala | Arg | Phe | Ala | Ile | Lys | Gly | Asp | Tyr |  |
|  |  |  |  | 260 |  |  |  |  | 265 |  |  |  |  | 270 |  |  |

| tgg | ggt | caa | ggc | acg | ctg | ctg | acc | gtt | tcc | tcg | gaa | ttt | ggt | ggc | gcg | 926 |
|---|---|---|---|---|---|---|---|---|---|---|---|---|---|---|---|---|
| Trp | Gly | Gln | Gly | Thr | Leu | Leu | Thr | Val | Ser | Ser | Glu | Phe | Gly | Gly | Ala |  |
|  |  |  | 275 |  |  |  |  | 280 |  |  |  |  | 285 |  |  |  |

| ccg | gag | ttc | ccg | aaa | ccg | tcc | acc | ccg | ccg | ggt | tct | tct | ggt | tta | gag | 974 |
|---|---|---|---|---|---|---|---|---|---|---|---|---|---|---|---|---|
| Pro | Glu | Phe | Pro | Lys | Pro | Ser | Thr | Pro | Pro | Gly | Ser | Ser | Gly | Leu | Glu |  |
|  | 290 |  |  |  |  | 295 |  |  |  |  | 300 |  |  |  |  |  |

| ggc | ggc | agc | ctg | gcc | gcg | ctg | acc | gcg | cac | cag | gcc | tgc | cac | ctg | ccg | 1022 |
|---|---|---|---|---|---|---|---|---|---|---|---|---|---|---|---|---|
| Gly | Gly | Ser | Leu | Ala | Ala | Leu | Thr | Ala | His | Gln | Ala | Cys | His | Leu | Pro |  |
|  | 305 |  |  |  |  | 310 |  |  |  |  | 315 |  |  |  |  |  |

| ctg | gag | act | ttc | acc | cgt | cat | cgc | cag | ccg | cgc | ggc | tgg | gaa | caa | ctg | 1070 |
|---|---|---|---|---|---|---|---|---|---|---|---|---|---|---|---|---|
| Leu | Glu | Thr | Phe | Thr | Arg | His | Arg | Gln | Pro | Arg | Gly | Trp | Glu | Gln | Leu |  |
| 320 |  |  |  |  | 325 |  |  |  |  | 330 |  |  |  |  | 335 |  |

| gag | cag | tgc | ggc | tat | ccg | gtg | cag | cgg | ctg | gtc | gcc | ctc | tac | ctg | gcg | 1118 |
|---|---|---|---|---|---|---|---|---|---|---|---|---|---|---|---|---|
| Glu | Gln | Cys | Gly | Tyr | Pro | Val | Gln | Arg | Leu | Val | Ala | Leu | Tyr | Leu | Ala |  |
|  |  |  |  | 340 |  |  |  |  | 345 |  |  |  |  | 350 |  |  |

| gcg | cga | ctg | tca | tgg | aac | cag | gtc | gac | cag | gtg | atc | cgc | aac | gcc | ctg | 1166 |
|---|---|---|---|---|---|---|---|---|---|---|---|---|---|---|---|---|
| Ala | Arg | Leu | Ser | Trp | Asn | Gln | Val | Asp | Gln | Val | Ile | Arg | Asn | Ala | Leu |  |
|  |  |  | 355 |  |  |  |  | 360 |  |  |  |  | 365 |  |  |  |

| gcc | agc | ccc | ggc | agc | ggc | ggc | gac | ctg | ggc | gaa | gcg | atc | cgc | gag | cag | 1214 |
|---|---|---|---|---|---|---|---|---|---|---|---|---|---|---|---|---|
| Ala | Ser | Pro | Gly | Ser | Gly | Gly | Asp | Leu | Gly | Glu | Ala | Ile | Arg | Glu | Gln |  |
|  |  | 370 |  |  |  |  | 375 |  |  |  |  | 380 |  |  |  |  |

| ccg | gag | cag | gcc | cgt | ctg | gcc | ctg | acc | ctg | gcc | gcc | gcc | gag | agc | gag | 1262 |
|---|---|---|---|---|---|---|---|---|---|---|---|---|---|---|---|---|
| Pro | Glu | Gln | Ala | Arg | Leu | Ala | Leu | Thr | Leu | Ala | Ala | Ala | Glu | Ser | Glu |  |
| 385 |  |  |  |  | 390 |  |  |  |  | 395 |  |  |  |  |  |  |

| | | |
|---|---|---|
| cgc ttc gtc cgg cag ggc acc ggc aac gac gag gcc ggc gcg gcc agc<br>Arg Phe Val Arg Gln Gly Thr Gly Asn Asp Glu Ala Gly Ala Ala Ser<br>400                       405                 410                 415 | 1310 |
| gcc gac gtg gtg agc ctg acc tgc ccg gtc gcc gcc ggt gaa tgc gcg<br>Ala Asp Val Val Ser Leu Thr Cys Pro Val Ala Ala Gly Glu Cys Ala<br>                 420                 425                 430 | 1358 |
| ggc ccg gcg gac agc ggc gac gcc ctg ctg gag cgc aac tat ccc act<br>Gly Pro Ala Asp Ser Gly Asp Ala Leu Leu Glu Arg Asn Tyr Pro Thr<br>435                       440                 445 | 1406 |
| ggc gcg gag ttc ctc ggc gac ggt ggc gac gtc agc ttc agc acc cgc<br>Gly Ala Glu Phe Leu Gly Asp Gly Gly Asp Val Ser Phe Ser Thr Arg<br>                 450                 455                 460 | 1454 |
| ggc acg cag aac tgg acg gtg gag cgg ctg ctc cag gcg cac cgc caa<br>Gly Thr Gln Asn Trp Thr Val Glu Arg Leu Leu Gln Ala His Arg Gln<br>465                       470                 475 | 1502 |
| ctg gag gag cgc ggc tat gtg ttc gtc ggc tac cac ggc acc ttc ctc<br>Leu Glu Glu Arg Gly Tyr Val Phe Val Gly Tyr His Gly Thr Phe Leu<br>480                       485                 490                 495 | 1550 |
| gaa gcg gcg caa agc atc gtc ttc ggc ggg gtg cgc gcg cgc agc cag<br>Glu Ala Ala Gln Ser Ile Val Phe Gly Gly Val Arg Ala Arg Ser Gln<br>                 500                 505                 510 | 1598 |
| gat ctc gac gcg atc tgg cgc ggt ttc tat atc gcc ggc gat ccg gcg<br>Asp Leu Asp Ala Ile Trp Arg Gly Phe Tyr Ile Ala Gly Asp Pro Ala<br>515                       520                 525 | 1646 |
| ctg gcc tac ggc tac gcc cag gac cag gaa ccc gac gcg cgc ggc cgg<br>Leu Ala Tyr Gly Tyr Ala Gln Asp Gln Glu Pro Asp Ala Arg Gly Arg<br>                 530                 535                 540 | 1694 |
| atc cgc aac ggt gcc ctg ctg cgg gtc tat gtg ccg cgc tcc agc ctg<br>Ile Arg Asn Gly Ala Leu Leu Arg Val Tyr Val Pro Arg Ser Ser Leu<br>545                       550                 555 | 1742 |
| ccg ggc ttc tac cgc acc ggc ctg acc ctg gcc gcg ccg gag gcg gcg<br>Pro Gly Phe Tyr Arg Thr Gly Leu Thr Leu Ala Ala Pro Glu Ala Ala<br>560                       565                 570                 575 | 1790 |
| ggc gag gtc gaa cgg ctg atc ggc cat ccg ctg ccg ctg cgc ctg gac<br>Gly Glu Val Glu Arg Leu Ile Gly His Pro Leu Pro Leu Arg Leu Asp<br>                 580                 585                 590 | 1838 |
| gcc atc acc ggc ccc gag gag gaa ggg ggc cgc ctg gag acc att ctc<br>Ala Ile Thr Gly Pro Glu Glu Glu Gly Gly Arg Leu Glu Thr Ile Leu<br>595                       600                 605 | 1886 |
| ggc tgg ccg ctg gcc gag cgc acc gtg gtg att ccc tcg gcg atc ccc<br>Gly Trp Pro Leu Ala Glu Arg Thr Val Val Ile Pro Ser Ala Ile Pro<br>610                       615                 620 | 1934 |
| acc gac ccg cgc aac gtc ggt ggc gac ctc gac ccg tcc agc atc ccc<br>Thr Asp Pro Arg Asn Val Gly Gly Asp Leu Asp Pro Ser Ser Ile Pro<br>625                       630                 635 | 1982 |
| gac aag gaa cag gcg atc agc gcc ctg ccg gac tac gcc agc cag ccc<br>Asp Lys Glu Gln Ala Ile Ser Ala Leu Pro Asp Tyr Ala Ser Gln Pro<br>640                       645                 650                 655 | 2030 |
| ggc aaa ccg ccg cat cac cac cat cac cat aaa gac gaa ctg tag tga<br>Gly Lys Pro Pro His His His His His His Lys Asp Glu Leu<br>                 660                 665 | 2078 |
| ctc gag<br>Leu Glu<br>670 | 2084 |

```
<210> SEQ ID NO 2
<211> LENGTH: 669
<212> TYPE: PRT
<213> ORGANISM: Artificial Sequence
<220> FEATURE:
<223> OTHER INFORMATION: VB4-845
```

```
<400> SEQUENCE: 2

Met Lys Tyr Leu Leu Pro Thr Ala Ala Ala Gly Leu Leu Leu Leu Ala
1               5                   10                  15

Ala Gln Pro Ala Met Ala His His His His His His Asp Ile Gln Met
            20                  25                  30

Thr Gln Ser Pro Ser Ser Leu Ser Ala Ser Val Gly Asp Arg Val Thr
        35                  40                  45

Ile Thr Cys Arg Ser Thr Lys Ser Leu Leu His Ser Asn Gly Ile Thr
    50                  55                  60

Tyr Leu Tyr Trp Tyr Gln Gln Lys Pro Gly Lys Ala Pro Lys Leu Leu
65                  70                  75                  80

Ile Tyr Gln Met Ser Asn Leu Ala Ser Gly Val Pro Ser Arg Phe Ser
                85                  90                  95

Ser Ser Gly Ser Gly Thr Asp Phe Thr Leu Thr Ile Ser Ser Leu Gln
            100                 105                 110

Pro Glu Asp Phe Ala Thr Tyr Tyr Cys Ala Gln Asn Leu Glu Ile Pro
        115                 120                 125

Arg Thr Phe Gly Gln Gly Thr Lys Val Glu Leu Lys Arg Ala Thr Pro
130                 135                 140

Ser His Asn Ser His Gln Val Pro Ser Ala Gly Gly Pro Thr Ala Asn
145                 150                 155                 160

Ser Gly Thr Ser Gly Ser Glu Val Gln Leu Val Gln Ser Gly Pro Gly
                165                 170                 175

Leu Val Gln Pro Gly Gly Ser Val Arg Ile Ser Cys Ala Ala Ser Gly
            180                 185                 190

Tyr Thr Phe Thr Asn Tyr Gly Met Asn Trp Val Lys Gln Ala Pro Gly
        195                 200                 205

Lys Gly Leu Glu Trp Met Gly Trp Ile Asn Thr Tyr Thr Gly Glu Ser
    210                 215                 220

Thr Tyr Ala Asp Ser Phe Lys Gly Arg Phe Thr Phe Ser Leu Asp Thr
225                 230                 235                 240

Ser Ala Ser Ala Ala Tyr Leu Gln Ile Asn Ser Leu Arg Ala Glu Asp
                245                 250                 255

Thr Ala Val Tyr Tyr Cys Ala Arg Phe Ala Ile Lys Gly Asp Tyr Trp
            260                 265                 270

Gly Gln Gly Thr Leu Leu Thr Val Ser Ser Glu Phe Gly Gly Ala Pro
        275                 280                 285

Glu Phe Pro Lys Pro Ser Thr Pro Pro Gly Ser Ser Gly Leu Glu Gly
    290                 295                 300

Gly Ser Leu Ala Ala Leu Thr Ala His Gln Ala Cys His Leu Pro Leu
305                 310                 315                 320

Glu Thr Phe Thr Arg His Arg Gln Pro Arg Gly Trp Glu Gln Leu Glu
                325                 330                 335

Gln Cys Gly Tyr Pro Val Gln Arg Leu Val Ala Leu Tyr Leu Ala Ala
            340                 345                 350

Arg Leu Ser Trp Asn Gln Val Asp Gln Val Ile Arg Asn Ala Leu Ala
        355                 360                 365

Ser Pro Gly Ser Gly Gly Asp Leu Gly Glu Ala Ile Arg Glu Gln Pro
    370                 375                 380

Glu Gln Ala Arg Leu Ala Leu Thr Leu Ala Ala Glu Ser Glu Arg
385                 390                 395                 400

Phe Val Arg Gln Gly Thr Gly Asn Asp Glu Ala Gly Ala Ala Ser Ala
```

```
            405                 410                 415
Asp Val Val Ser Leu Thr Cys Pro Val Ala Gly Glu Cys Ala Gly
            420                 425                 430

Pro Ala Asp Ser Gly Asp Ala Leu Leu Glu Arg Asn Tyr Pro Thr Gly
            435                 440                 445

Ala Glu Phe Leu Gly Asp Gly Asp Val Ser Phe Ser Thr Arg Gly
            450                 455                 460

Thr Gln Asn Trp Thr Val Glu Arg Leu Gln Ala His Arg Gln Leu
465                 470                 475                 480

Glu Glu Arg Gly Tyr Val Phe Val Gly Tyr His Gly Thr Phe Leu Glu
                485                 490                 495

Ala Ala Gln Ser Ile Val Phe Gly Gly Val Arg Ala Arg Ser Gln Asp
            500                 505                 510

Leu Asp Ala Ile Trp Arg Gly Phe Tyr Ile Ala Gly Asp Pro Ala Leu
            515                 520                 525

Ala Tyr Gly Tyr Ala Gln Asp Gln Glu Pro Asp Ala Arg Gly Arg Ile
            530                 535                 540

Arg Asn Gly Ala Leu Leu Arg Val Tyr Val Pro Arg Ser Ser Leu Pro
545                 550                 555                 560

Gly Phe Tyr Arg Thr Gly Leu Thr Leu Ala Ala Pro Glu Ala Ala Gly
                565                 570                 575

Glu Val Glu Arg Leu Ile Gly His Pro Leu Pro Leu Arg Leu Asp Ala
            580                 585                 590

Ile Thr Gly Pro Glu Glu Gly Gly Arg Leu Glu Thr Ile Leu Gly
            595                 600                 605

Trp Pro Leu Ala Glu Arg Thr Val Val Ile Pro Ser Ala Ile Pro Thr
610                 615                 620

Asp Pro Arg Asn Val Gly Gly Asp Leu Asp Pro Ser Ser Ile Pro Asp
625                 630                 635                 640

Lys Glu Gln Ala Ile Ser Ala Leu Pro Asp Tyr Ala Ser Gln Pro Gly
                645                 650                 655

Lys Pro Pro His His His His His His Lys Asp Glu Leu
            660                 665

<210> SEQ ID NO 3
<211> LENGTH: 254
<212> TYPE: PRT
<213> ORGANISM: Artificial Sequence
<220> FEATURE:
<223> OTHER INFORMATION: Ep-CAM Binding Protein

<400> SEQUENCE: 3

Asp Ile Gln Met Thr Gln Ser Pro Ser Ser Leu Ser Ala Ser Val Gly
1               5                   10                  15

Asp Arg Val Thr Ile Thr Cys Arg Ser Thr Lys Ser Leu Leu His Ser
            20                  25                  30

Asn Gly Ile Thr Tyr Leu Tyr Trp Tyr Gln Gln Lys Pro Gly Lys Ala
        35                  40                  45

Pro Lys Leu Leu Ile Tyr Gln Met Ser Asn Leu Ala Ser Gly Val Pro
    50                  55                  60

Ser Arg Phe Ser Ser Gly Ser Gly Thr Asp Phe Thr Leu Thr Ile
65                  70                  75                  80

Ser Ser Leu Gln Pro Glu Asp Phe Ala Thr Tyr Tyr Cys Ala Gln Asn
                85                  90                  95

Leu Glu Ile Pro Arg Thr Phe Gly Gln Gly Thr Lys Val Glu Leu Lys
```

```
                    100                 105                 110
Arg Ala Thr Pro Ser His Asn Ser His Gln Val Pro Ser Ala Gly Gly
            115                 120                 125

Pro Thr Ala Asn Ser Gly Thr Ser Gly Ser Glu Val Gln Leu Val Gln
        130                 135                 140

Ser Gly Pro Gly Leu Val Gln Pro Gly Gly Ser Val Arg Ile Ser Cys
145                 150                 155                 160

Ala Ala Ser Gly Tyr Thr Phe Thr Asn Tyr Gly Met Asn Trp Val Lys
                165                 170                 175

Gln Ala Pro Gly Lys Gly Leu Glu Trp Met Gly Trp Ile Asn Thr Tyr
            180                 185                 190

Thr Gly Glu Ser Thr Tyr Ala Asp Ser Phe Lys Gly Arg Phe Thr Phe
        195                 200                 205

Ser Leu Asp Thr Ser Ala Ser Ala Ala Tyr Leu Gln Ile Asn Ser Leu
    210                 215                 220

Arg Ala Glu Asp Thr Ala Val Tyr Tyr Cys Ala Arg Phe Ala Ile Lys
225                 230                 235                 240

Gly Asp Tyr Trp Gly Gln Gly Thr Leu Leu Thr Val Ser Ser
                245                 250
```

<210> SEQ ID NO 4
<211> LENGTH: 16
<212> TYPE: PRT
<213> ORGANISM: Artificial Sequence
<220> FEATURE:
<223> OTHER INFORMATION: CDR1 (L)

<400> SEQUENCE: 4

```
Arg Ser Thr Lys Ser Leu Leu His Ser Asn Gly Ile Thr Tyr Leu Tyr
1               5                   10                  15
```

<210> SEQ ID NO 5
<211> LENGTH: 7
<212> TYPE: PRT
<213> ORGANISM: Artificial Sequence
<220> FEATURE:
<223> OTHER INFORMATION: CDR2 (L)

<400> SEQUENCE: 5

```
Gln Met Ser Asn Leu Ala Ser
1               5
```

<210> SEQ ID NO 6
<211> LENGTH: 9
<212> TYPE: PRT
<213> ORGANISM: Artificial Sequence
<220> FEATURE:
<223> OTHER INFORMATION: CDR3 (L)

<400> SEQUENCE: 6

```
Ala Gln Asn Leu Glu Ile Pro Arg Thr
1               5
```

<210> SEQ ID NO 7
<211> LENGTH: 5
<212> TYPE: PRT
<213> ORGANISM: Artificial Sequence
<220> FEATURE:
<223> OTHER INFORMATION: CDR1 (H)

<400> SEQUENCE: 7

Asn Tyr Gly Met Asn

```
<210> SEQ ID NO 8
<211> LENGTH: 17
<212> TYPE: PRT
<213> ORGANISM: Artificial Sequence
<220> FEATURE:
<223> OTHER INFORMATION: CDR2 (H)

<400> SEQUENCE: 8

Trp Ile Asn Thr Tyr Thr Gly Glu Ser Thr Tyr Ala Asp Ser Phe Lys
1               5                   10                  15
Gly

<210> SEQ ID NO 9
<211> LENGTH: 7
<212> TYPE: PRT
<213> ORGANISM: Artificial Sequence
<220> FEATURE:
<223> OTHER INFORMATION: CDR3 (H)

<400> SEQUENCE: 9

Phe Ala Ile Lys Gly Asp Tyr
1               5

<210> SEQ ID NO 10
<211> LENGTH: 64
<212> TYPE: DNA
<213> ORGANISM: Artificial Sequence
<220> FEATURE:
<223> OTHER INFORMATION: Tox1 primer

<400> SEQUENCE: 10
ctcggaattc ggtggcgcgc cggagttccc gaaaccgtcc accccgccgg gttcttctgg      60
ttta                                                                  64

<210> SEQ ID NO 11
<211> LENGTH: 60
<212> TYPE: DNA
<213> ORGANISM: Artificial Sequence
<220> FEATURE:
<223> OTHER INFORMATION: Tox2 primer

<400> SEQUENCE: 11
gtcaagcttc tacagttcgt ctttatggtg atggtggtga tgcggcggtt tcccgggctg      60

<210> SEQ ID NO 12
<211> LENGTH: 73
<212> TYPE: DNA
<213> ORGANISM: Artificial Sequence
<220> FEATURE:
<223> OTHER INFORMATION: Oligonucleotide

<400> SEQUENCE: 12
ctagataacg agggcaaaaa atgaaaaaga cagctatcgc gattgcagtg gcactggctg      60
gtttcgctac cgt                                                        73

<210> SEQ ID NO 13
<211> LENGTH: 48
<212> TYPE: DNA
<213> ORGANISM: Artificial Sequence
<220> FEATURE:
<223> OTHER INFORMATION: Oligonucleotide

<400> SEQUENCE: 13
```

```
gccactgcaa tcgcgatagc tgtcttttc attttttgcc ctcgttat            48

<210> SEQ ID NO 14
<211> LENGTH: 34
<212> TYPE: DNA
<213> ORGANISM: Artificial Sequence
<220> FEATURE:
<223> OTHER INFORMATION: Oligonucleotide

<400> SEQUENCE: 14
agcgcaggcc gaccaccatc atcaccatca cgat                          34

<210> SEQ ID NO 15
<211> LENGTH: 55
<212> TYPE: DNA
<213> ORGANISM: Artificial Sequence
<220> FEATURE:
<223> OTHER INFORMATION: Oligonucleotide

<400> SEQUENCE: 15
atcgtgatgg tgatgatggt ggtcggcctg cgctacggta gcgaaaccag ccagt   55
```